United States Patent [19]

Yoshioka et al.

[11] Patent Number: 4,572,912
[45] Date of Patent: Feb. 25, 1986

[54] THIAZOLIDINE DERIVATIVES, THEIR PREPARATION AND COMPOSITIONS CONTAINING THEM

[75] Inventors: Takao Yoshioka; Eiici Kitazawa; Tomoyuki Kurumada; Mitsuo Yamazaki; Kazou Hasegawa, all of Hiromachi, Japan

[73] Assignee: Sankyo Company Limited, Tokyo, Japan

[21] Appl. No.: 644,996

[22] Filed: Aug. 28, 1984

[30] Foreign Application Priority Data

Aug. 30, 1983 [JP] Japan .................. 58-158375

[51] Int. Cl.$^4$ ................ C07D 417/12; A61K 31/425
[52] U.S. Cl. ................... 514/369; 514/370; 548/183; 548/184; 548/191
[58] Field of Search ............ 548/183, 184, 191; 514/369, 370

[56] References Cited

U.S. PATENT DOCUMENTS 4,340,605 7/1982 Kawamatsu ............ 424/263
4,461,902 7/1984 Kuwomatsu ............ 548/183

Primary Examiner—Robert Gerstl
Attorney, Agent, or Firm—Frishauf, Holtz, Goodman & Woodward

[57] ABSTRACT

The compounds of formula (I):

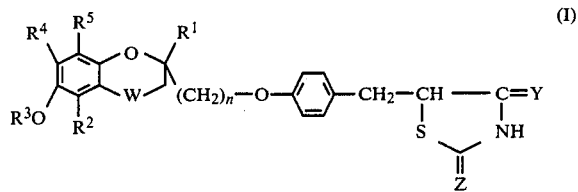

[in which:

$R^1$ and $R^2$ are the same or different and each represents hydrogen or $C_1-C_5$ alkyl;

$R^3$ represents hydrogen, an acyl group, a ($C_1-C_6$ alkoxy)carbonyl group or an aralkyloxycarbonyl group;

$R^4$ and $R^5$ are the same or different and each represents hydrogen, $C_1-C_5$ alkyl or $C_1-C_5$ alkoxy, or $R^4$ and $R^5$ together represent a $C_1$14 $C_4$ alkylenedioxy group;

n is 1, 2 or 3;

W represents the $-CH_2-$, $>CO$ or $>CH-OR^6$ group (in which $R^6$ represents any one of the atoms or groups defined for $R^3$ and may be the same as or different from $R^3$); and Y and Z are the same or different and each represents oxygen or imino]

and pharmaceutically acceptable salts thereof have various valuable therapeutic effects on the blood system and may be prepared by a process which includes reacting a corresponding halopropionic acid derivative with thiourea.

39 Claims, No Drawings

THIAZOLIDINE DERIVATIVES, THEIR PREPARATION AND COMPOSITIONS CONTAINING THEM

BACKGROUND OF THE INVENTION

The present invention relates to a series of new thiazolidine derivatives, which we have found to have a variety of valuable biological activities, coupled with an exceedingly low toxicity. The invention also provides processes for preparing the compounds and pharmaceutical compositions containing them.

A number of thiazolidine derivatives are disclosed in European Patent Publication No. 8203 which corresponds to U.S. Pat. No. 4,287,200 and in Chem. Pharm. Bull., 30, 3580 (1982). Certain of the thiazolidine derivatives disclosed in these documents have the ability to lower blood lipid and blood sugar levels, although these compounds are a little toxic.

We have now discovered a series of new thiazolidine derivatives which likewise have the ability to lower blood lipid and blood sugar levels and, in addition, have a number of other valuable activities, but which have very low toxicity. In general, the compounds of the invention show blood lipid metabolism ameliorating activity. Specifically, the compounds have the ability to decrease the levels of blood lipid peroxides, blood triglycerides and blood cholesterol.

BRIEF SUMMARY OF THE INVENTION

The compounds of the present invention are compounds of formula (I):

[Structure (I)]

[in which:
$R^1$ and $R^2$ are the same or different and each represents a hydrogen atom or a $C_1$–$C_5$ alkyl group;
$R^3$ represents a hydrogen atom, a $C_1$–$C_6$ aliphatic acyl group, an alicyclic acyl group, an aromatic acyl group, a heterocyclic acyl group, an araliphatic acyl group, a ($C_1$–$C_6$ alkoxy)carbonyl group or an aralkyloxycarbonyl group;
$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;
n is 1, 2 or 3;
W represents the —$CH_2$—, $>$CO or $>$CH—$OR^6$ group (in which $R^6$ represents any one of the atoms or groups defined for $R^3$ and may be the same as or different from $R^3$); and
Y and Z are the same or different and each represents an oxygen atom or an imino (=NH) group]
and pharmaceutically acceptable salts thereof.

The invention also provides a process for preparing the compounds of the invention by:
(a) reacting a halopropionic acid derivative of formula (II):

[Structure (II)]

[in which:
$R^1$, $R^2$, $R^3$, $R^4$, $R^5$, n and W are as defined above;
X represents a halogen atom; and
A represents a cyano group, a carboxy group, an alkoxycarbonyl group, a carbamoyl group or a group of formula —COO(M)$_m$, in which M represents a cation and m represents the reciprocal of the valency of the cation M] with thiourea, to give a compound of formula (III):

[Structure (III)]

(in which $R^1$, $R^2$, $R^3$, $R^4$, $R^5$, n, W and Y are as defined above) and then,
(b) if necessary, subjecting said compound to hydrolysis (which may be selective) to prepare said compound of formula (I),
(c) optionally, where W represents a $>$C=O group, reducing the compound produced in step (a) or step (b) to a compound where W represents a $>$CH—OH group,
(d) optionally, where W represents a $>$CH—OH group, acylating the compound to give a compound in which W represents a group of formula $>$CH—$OR^{6'}$ (in which $R^{6'}$ represents any of the groups defined for $R^6$ but not the hydrogen atom), and
(e) if necessary, salifying the product.

The invention also provides a pharmaceutical composition for the treatment of hyperlipaemia or hyperglycaemia, which comprises at least one compound of the invention in admixture with a pharmaceutically acceptable carrier or diluent.

DETAILED DESCRIPTION OF INVENTION

The compounds of the invention, which are 5-[4-(chromanalkoxy)benzyl]thiazolidine derivatives, may be represented by the formulae (Ia), (Ib) and (Ic):

[Structure (Ia)]

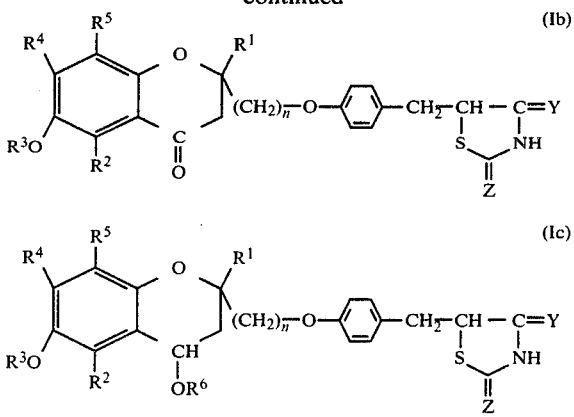

(in which $R^1$, $R^2$, $R^3$, $R^4$, $R^5$, $R^6$, n, Y and Z are as defined above) and include pharmaceutically acceptable salts thereof.

In the compounds of the invention, where $R^1$ or $R^2$ represents an alkyl group, this may be a straight or branched chain alkyl group having from 1 to 5 carbon atoms and is preferably a primary or secondary alkyl group, for example the methyl, ethyl, propyl, isopropyl, butyl, isobutyl, pentyl or isopentyl group.

Where $R^3$, $R^6$ or $R^{6'}$ represents an aliphatic acyl group, this preferably has from 1 to 6 carbon atoms and may include one or more carbon-carbon double or triple bonds. Examples of such groups include the formyl, acetyl, propionyl, butyryl, isobutyryl, pivaloyl, hexanoyl, acryloyl, methacryloyl and crotonoyl groups. Where $R^3$, $R^6$ or $R^{6'}$ represents an alicyclic acyl group, it is preferably a cyclopentanecarbonyl, cyclohexanecarbonyl or cycloheptanecarbonyl group. Where $R^3$, $R^6$ or $R^{6'}$ represents an aromatic acyl group, the aromatic moiety thereof may optionally have one or more substituents (for example nitro, amino, alkylamino, dialkylamino, alkoxy, halo, alkyl or hydroxy substituents); examples of such aromatic acyl groups include the benzoyl, p-nitrobenzoyl, m-fluorobenzoyl, o-chlorobenzoyl, p-aminobenzoyl, m-(dimethylamino)-benzoyl, o-methoxybenzoyl, 3,4-dichlorobenzoyl, 3,5-di-t-butyl-4-hydroxybenzoyl and 1-naphthoyl groups. Where $R^3$, $R^6$ or $R^{6'}$ represents a heterocyclic acyl group, the heterocyclic moiety thereof preferably has one or more, preferably one, oxygen, sulfur or nitrogen hetero atoms and has from 4 to 7 ring atoms; examples of such heterocyclic acyl groups include the 2-furoyl, 3-thenoyl, 3-pyridinecarbonyl (nicotinoyl) and 4-pyridinecarbonyl groups. Where $R^3$, $R^6$ or $R^{6'}$ represents an araliphatic acyl group, the aliphatic moiety thereof may optionally have one or more carbon-carbon double or triple bonds and the aryl moiety thereof may optionally have one or more substituents (for example nitro, amino, alkylamino, dialkylamino, alkoxy, halo, alkyl or hydroxy substituents); examples of such araliphatic acyl groups include the phenylacetyl, p-chlorophenylacetyl, phenylpropionyl and cinnamoyl groups. Where $R^3$, $R^6$ or $R^{6'}$ represents a ($C_1$–$C_6$ alkoxy)carbonyl group, the alkyl moiety thereof may be any one of those alkyl groups as defined for $R^1$ and $R^2$, but is preferably a methyl or ethyl group, and the alkoxycarbonyl group represented by $R^3$, $R^6$ or $R^{6'}$ is therefore preferably a methoxycarbonyl or ethoxycarbonyl group. Where $R^3$, $R^6$ or $R^{6'}$ represents an aralkyloxycarbonyl group, the aralkyl moiety thereof may be any one of those included within the araliphatic acyl group represented by $R^3$, $R^6$ or $R^{6'}$, but is preferably a benzoyloxycarbonyl group.

Where $R^4$ and $R^5$ represent alkyl groups, they may be the same or different and may be straight or branched chain alkyl groups. They preferably have from 1 to 5 carbon atoms and examples include the methyl, ethyl, propyl, isopropyl, butyl, isobutyl, t-butyl, pentyl and isopentyl groups.

Where $R^4$ and $R^5$ represent alkoxy groups, these may be the same or different and may be straight or branched chain groups, preferably having from 1 to 4 carbon atoms. Examples include the methoxy, ethoxy, propoxy, isopropoxy and butoxy groups. Alternatively, $R^4$ and $R^5$ may together represent a $C_1$–$C_4$ alkylenedioxy group, more preferably a methylenedioxy or ethylenedioxy group.

Preferred classes of compounds of the present invention are as follows:

(1) Compounds in which $R^3$ represents a hydrogen atom, a $C_1$–$C_6$ aliphatic acyl group, an aromatic acyl group or a heterocyclic acyl group.

(2) Compounds in which Y represents an oxygen atom; $R^1$ and $R^2$ are the same or different and each represents a hydrogen atom or a $C_1$–$C_5$ alkyl group; $R^3$ represents a hydrogen atom, a $C_1$–$C_6$ aliphatic acyl group, an aromatic acyl group or a pyridinecarbonyl group; and $R^4$ and $R^5$ are the same or different and each represents a hydrogen atom, a $C_1$–$C_5$ alkyl group or a $C_1$ or $C_2$ alkoxy group.

(3) Compounds as defined in (2) above, in which: $R^1$, $R^2$, $R^4$ and $R^5$ are the same or different and each represents a hydrogen atom or a $C_1$–$C_5$ alkyl group; n is 1 or 2; and W represents the —$CH_2$— or >CO group.

(4) Compounds as defined in (3) above, in which $R^3$ represents a hydrogen atom, a $C_1$–$C_5$ aliphatic acyl group, a benzoyl group, or a nicotinoyl group.

(5) Compounds as defined in (4) above, in which: $R^1$ and $R^4$ are the same or different and each represents a $C_1$–$C_5$ alkyl group; $R^2$ and $R^5$ are the same or different and each represents the hydrogen atom or the methyl group; and $R^3$ represents a hydrogen atom or a $C_1$–$C_4$ aliphatic acyl group.

(6) Compounds in which: W represents the —$CH_2$— or >CO group; Y and Z both represent oxygen atoms; n is 1 or 2; $R^1$ and $R^4$ are the same or different and each represents a $C_1$–$C_4$ alkyl group; $R^2$ and $R^5$ are the same or different and each represents the hydrogen atom or the methyl group; and $R^3$ represents a hydrogen atom or a $C_1$–$C_4$ aliphatic acyl group.

(7) Compounds as defined in (6) above, in which n is 1.

(8) Compounds as defined in (6) or (7) above, in which W represents the —$CH_2$— group.

Preferred compounds among the compounds of this invention are those wherein: $R^1$ is a $C_1$–$C_4$ alkyl group, more preferably a methyl or isobutyl group, most preferably a methyl group; $R^2$ is a hydrogen atom or a $C_1$–$C_4$ alkyl group, preferably a hydrogen atom, or a methyl or isopropyl group, more preferably a hydrogen atom or a methyl group, most preferably a methyl group; $R^3$ is a hydrogen atom, a $C_1$–$C_4$ aliphatic acyl group, an aromatic acyl group or a pyridinecarbonyl group, preferably a hydrogen atom, or an acetyl, butyryl, benzoyl or nicotinoyl group, more preferably a hydrogen atom or an acetyl, butyryl or benzoyl group, most preferably a hydrogen atom or an acetyl group;

$R^4$ is a hydrogen atom, a $C_1$–$C_4$ alkyl group or a $C_1$ or $C_2$ alkoxy group, preferably a methyl, isopropyl, t-butyl or methoxy group, more preferably a methyl or t-butyl group, most preferably a methyl group; $R^5$ is a hydrogen atom, a $C_1$–$C_4$ alkyl group or a $C_1$ or $C_2$ alkoxy group, preferably a hydrogen atom, or a methyl or methoxy group, more preferably a hydrogen atom or a methyl group and most preferably a methyl group; n is 1 or 2, preferably 1; Y is an oxygen atom; Z is an oxygen atom or an imino group, most preferably an oxygen atom; and W is a —CH$_2$— or >C=O group, preferably a —CH$_2$— group.

Specific examples of compounds of the present invention are given in the following list:

1. 5-[4-(6-hydroxy-2,5,7,8-tetramethylchroman-2-ylmethoxy)benzyl]thiazolidine-2,4-dione
2. 5-[4-(6-hydroxy-2,5,7-trimethylchroman-2-ylmethoxy)benzyl]thiazolidine-2,4-dione
3. 5-[4-(7-t-butyl-6-hydroxy-2-methylchroman-2-ylmethoxy)benzyl]thiazolidine-2,4-dione
4. 5-[4-(6-hydroxy-2-methylchroman-2-ylmethoxy)benzyl]thiazolidine-2,4-dione
5. 5-[4-(2-ethyl-6-hydroxy-5,7,8-trimethylchroman-2-ylmethoxy)benzyl]thiazolidine-2,4-dione
6. 5-[4-(6-hydroxy-5,7,8-trimethylchroman-2-ylmethoxy)benzyl]thiazolidine-2,4-dione
7. 5-[4-(6-hydroxy-2,7,8-trimethylchroman-2-ylmethoxy)benzyl]thiazolidine-2,4-dione
8. 5-[4-(6-hydroxy-7-isopropyl-2-methylchroman-2-ylmethoxy)benzyl]thiazolidine-2,4-dione
9. 5-[4-(6-hydroxy-5,7-diisopropyl-2-methylchroman-2-ylmethoxy)benzyl]thiazolidine-2,4-dione
10. 5-[4-(6-hydroxy-2-methyl-7-propylchroman-2-ylmethoxy)benzyl]thiazolidine-2,4-dione
11. 5-{4-[2-(6-hydroxy-2,5,7,8-tetramethylchroman-2-yl)ethoxy]benzyl}thiazolidine-2,4-dione
12. 5-{4-[2-(6-hydroxy-2,5,7-trimethylchroman-2-yl)ethoxy]benzyl}thiazolidine-2,4-dione
13. 5-{4-[2-(7-t-butyl-6-hydroxy-2-methylchroman-2-yl)ethoxy]benzyl}thiazolidine-2,4-dione
14. 5-{4-[2-(6-hydroxy-2-methylchroman-2-yl)ethoxy]benzyl}thiazolidine-2,4-dione
15. 5-{4-[2-(2-ethyl-6-hydroxy-5,7,8-trimethylchroman-2-yl)ethoxy]benzyl}thiazolidine-2,4-dione
16. 5-{4-[2-(6-hydroxy-5,7,8-trimethylchroman-2-yl)ethoxy]benzyl}thiazolidine-2,4-dione
17. 5-{4-[2-(6-hydroxy-5,7-diisopropyl-2,8-dimethylchroman-2-yl)ethoxy]benzyl}thiazolidine-2,4-dione
18. 5-{4-[2-(6-hydroxy-7-pentyl-2-propylchroman-2-yl)ethoxy]benzyl}thiazolidine-2,4-dione
19. 5-[4-(6-hydroxy-7,8-dimethoxy-2,5-dimethylchroman-2-ylmethoxy)benzyl]thiazolidine-2,4-dione
20. 5-[4-(6-hydroxy-7,8-dimethoxy-5-methylchroman-2-ylmethoxy)benzyl]thiazolidine-2,4-dione
21. 5-[4-(2-ethyl-6-hydroxy-7,8-dimethoxy-5-methylchroman-2-ylmethoxy)benzyl]thiazolidine-2,4-dione
22. 5-[4-(6-hydroxy-2,5-dimethyl-7,8-methylenedioxychroman-2-ylmethoxy)benzyl]thiazolidine-2,4-dione
23. 5-{4-[2-(6-hydroxy-7,8-dimethoxy-2,5-dimethylchroman-2-yl)ethoxy]benzyl}thiazolidine-2,4-dione
24. 5-{4-[3-(6-hydroxy-2,5,7,8-tetramethylchroman-2-yl)propoxy]benzyl}thiazolidine-2,4-dione
25. 5-{4-[3-(7-t-butyl-6-hydroxychroman-2-yl)propoxy]benzyl}thiazolidine-2,4-dione
26. 5-[4-(6-hydroxychroman-2-ylmethoxy)benzyl]thiazolidine-2,4-dione
27. 5-[4-(6-hydroxy-2,7-dimethylchroman-2-ylmethoxy)benzyl]thiazolidine-2,4-dione
28. 5-[4-(6-hydroxy-5,7,8-trimethyl-2-propylchroman-2-ylmethoxy)benzyl]thiazolidine-2,4-dione
29. 5-[4-(7-t-butyl-6-hydroxy-2-isopropylchroman-2-ylmethoxy)benzyl]thiazolidine-2,4-dione
30. 5-[4-(6-hydroxy-2-isobutyl-5,7,8-trimethylchroman-2-ylmethoxy)benzyl]thiazolidine-2,4-dione
31. 5-[4-(6-hydroxy-2-isobutyl-7-isopropylchroman-2-ylmethoxy)benzyl]thiazolidine-2,4-dione
32. 5-[4-(6-hydroxy-5,7,8-trimethyl-2-pentylchroman-2-ylmethoxy)benzyl]thiazolidine-2,4-dione
33. 5-[4-(6-hydroxy-2-isopentyl-5,7-dimethylchroman-2-ylmethoxy)benzyl]thiazolidine-2,4-dione
34. 5-[4-(6-hydroxy-2,5,7,8-tetramethylchroman-2-ylmethoxy)benzyl]-2-iminothiazolidin-4-one
35. 5-[4-(6-hydroxy-5,7-diisopropyl-2-methylchroman-2-ylmethoxy)benzyl]-2-iminothiazolidin-4-one
36. 5-[4-(7-t-butyl-6-hydroxy-2-methylchroman-2-ylmethoxy)benzyl]-2-iminothiazolidin-4-one 37. 5-[4-(6-hydroxy-2-methylchroman-2-ylmethoxy)benzyl]-2-iminothiazolidin-4-one
38. 5-[4-(2-ethyl-6-hydroxy-5,7,8-trimethylchroman-2-ylmethoxy)benzyl]-2-iminothiazolidin-4-one
39. 5-[4-(6-hydroxy-7,8-dimethoxy-2,5-dimethylchroman-2-ylmethoxy)benzyl]-2-iminothiazolidin-4-one
40. 5-[4-(6-hydroxy-5,7,8-trimethylchroman-2-ylmethoxy)benzyl]-2-iminothiazolidin-4-one
41. 5-[4-(2-ethyl-6-hydroxy-7,8-dimethoxy-5-methylchroman-2-ylmethoxy)benzyl]-2-iminothiazolidin-4-one
42. 5-[4-(6-hydroxy-2,7-dimethylchroman-2-ylmethoxy)benzyl]-2-iminothiazolidin-4-one
43. 5-{4-[2-(6-hydroxy-2,5,7,8-tetramethylchroman-2-yl)ethoxy]benzyl}-2-iminothiazlidin-4-one
44. 5-{4-[2-(6-hydroxy-2-methylchroman-2-yl)ethoxy]benzyl}-2-iminothiazolidin-4-one
45. 5-{4-[2-(7-t-butyl-6-hydroxy-2-methylchroman-2-yl)ethoxy]benzyl}-2-iminothiazolidin-4-one
46. 5-{4-[2-(6-hydroxy-7,8-dimethoxy-2,5-dimethylchroman-2-yl)ethoxy]benzyl}-2-iminothiazolidin-4-one
47. 5-{4-[2-(2-ethyl-6-hydroxy-7,8-dimethoxy-5-methylchroman-2-yl)ethoxy]benzyl}-2-iminothiazolidin-4-one
48. 5-{4-[2-(6-hydroxy-7,8-dimethoxy-5-methylchroman-2-yl)ethoxy]benzyl}-2-iminothiazolidin-4-one
49. 5-{4-[3-(6-hydroxy-2,5,7,8-tetramethylchroman-2-yl)propoxy]benzyl}-2-iminothiazolidin-4-one
50. 5-[4-(6-hydroxy-2,5,7,8-tetramethylchroman-2-ylmethoxy)benzyl]-2,4-diiminothiazolidine
51. 5-[4-(6-hydroxy-2,5,7-trimethylchroman-2-ylmethoxy)benzyl]-2,4-diiminothiazolidine
52. 5-[4-(7-t-butyl-6-hydroxy-2-methylchroman-2-ylmethoxy)benzyl]-2,4-diiminothiazolidine
53. 5-[4-(6-hydroxy-2-methylchroman-2-ylmethoxy)benzyl]-2,4-diiminothiazolidine
54. 5-[4-(7-t-butyl-6-hydroxychroman-2-ylmethoxy)benzyl]-2,4-diiminothiazolidine
55. 5-[4-(6-hydroxy-7,8-dimethoxy-2,5-dimethylchroman-2-ylmethoxy)benzyl]-2,4-diiminothiazolidine
56. 5-[4-(6-hydroxy-7,8-dimethoxy-5-methylchroman-2-ylmethoxy)benzyl]-2,4-diiminothiazolidine
57. 5-[4-(2-ethyl-6-hydroxy-7,8-dimethoxy-5-methylchroman-2-ylmethoxy)benzyl]-2,4-diiminothiazolidine
58. 5-{4-[2-(6-hydroxy-2,5,7,8-tetramethylchroman-2-yl)ethoxy]benzyl}-2,4-diiminothiazolidine
59. 5-{4-[2-(7-t-butyl-6-hydroxy-2-methylchroman-2-yl)ethoxy]benzyl}-2,4-diiminothiazolidine 60. 5-{4-[2-(6-hydroxy-2-methylchroman-2-yl)ethoxy]benzyl}-2,4-diiminothiazolidine
61. 5-{4-[3-(6-hydroxy-7,8-dimethoxy-2,5-dimethylchroman-2-yl)propoxy]benzyl}-2,4-diiminothiazolidine
62. 5-[4-(6-acetoxy-2,5,7,8-tetramethylchroman-2-ylmethoxy)benzyl]thiazolidine-2,4-dione
63. 5-[4-(6-benzoyloxy-2,5,7,8-tetramethylchroman-2-ylmethoxy)benzyl]thiazolidine-2,4-dione
64. 5-[4-(6-acetoxy-7-t-butyl-2-methylchroman-2-ylmethoxy)benzyl]thiazolidine-2,4-dione
65. 5-[4-(6-acetoxy-2-methylchroman-2-ylmethoxy)benzyl]thiazolidine-2,4-dione
66. 5-[4-(2-ethyl-6-isobutyryloxy-5,7,8-trimethylchroman-2-ylmethoxy)benzyl]thiazolidine-2,4-dione
67. 5-[4-(6-butyryloxy-2,5,7,8-tetramethylchroman-2-ylmethoxy)benzyl]thiazolidine-2,4-dione
68. 5-{4-[2-(6-m-fluorobenzoyloxy-2,5,7-trimethylchroman-2-yl)ethoxy]benzyl}thiazolidine-2,4-dione
69. 5-{4-[2-(6-acryloyloxy-7-t-butyl-2-methylchroman-2-yl)ethoxy]benzyl}thiazolidine-2,4-dione
70. 5-{4-[2-(6-heptanoyloxy-2-methylchroman-2-yl)ethoxy]benzyl}thiazolidine-2,4-dione
71. 5-{4-[2-(6-p-aminobenzoyloxy-2-ethyl-5,7,8-trimethylchroman-2-yl)ethoxy]benzyl}thiazolidine-2,4-dione
72. 5-{4-[2-(5,7,8-trimethyl-6-3'-thenoyloxychroman-2-yl)ethoxy]benzyl}thiazolidine-2,4-dione
73. 5-{4-[2-(6-2'-furoyloxy-5,7-diisopropyl-2,8-dimethylchroman-2-yl)ethoxy]benzyl}thiazolidine-2,4-dione
74. 5-{4-[2-(6-β-naphthoyloxy-7-pentyl-2-propylchroman-2-yl)ethoxy]benzyl}thiazolidine-2,4-dione
75. 5-[4-(2,5,7,8-tetramethyl-6-nicotinoyloxychroman-2-ylmethoxy)benzyl]thiazolidine-2,4-dione
76. 5-{4-[6-(3,5-dichlorobenzoyloxy)-7,8-dimethoxy-5-methylchroman-2-ylmethoxy]benzyl}thiazolidine-2,4-dione
77. 5-[4-(2-ethyl-7,8-dimethoxy-5-methyl-6-valeryloxychroman-2-ylmethoxy)benzyl]thiazolidine-2,4-dione
78. 5-[4-(6-isonicotinoyloxy-2,5-dimethyl-7,8-methylenedioxychroman-2-ylmethoxy)benzyl]thiazolidine-2,4-dione
79. 5-{4[2-(7,8-dimethoxy-2,5-dimethyl-6-p-nitrobenzoyloxychroman-2-yl)ethoxy]benzyl}thiazolidine-2,4-dione
80. 5-{4-[3-(6-o-chlorobenzoyloxy-2,5,7,8-tetramethylchroman-2-yl)propyl]benzyl}thiazolidine-2,4-dione
81. 5-{4-[3-(7-t-butyl-6-m-dimethylaminobenzoyloxy-5-methylchroman-2-yl)propoxy]benzyl}thiazolidine-2,4-dione
82. 5-[4-(6-acetoxychroman-2-ylmethoxy)benzyl]thiazolidine-2,4-dione
83. 5-[4-(6-acetoxy-2,7-dimethylchroman-2-ylmethoxy)benzyl]thiazolidine-2,4-dione
84. 5-[4-(6-acetoxy-2,5,7,8-tetramethylchroman-2-ylmethoxy)benzyl]-2-iminothiazolidin-4-one
85. 5-[4-(6-acetoxy-5,7-diisopropyl-2-methylchroman-2-ylmethoxy)benzyl]-2-iminothiazolidin-4-one
86. 5-{4-[7-t-butyl-6-(3,5-di-t-butyl-4-hydroxybenzoyloxy)-2-methylchroman-2-ylmethoxy]benzyl}-2-iminothiazolidin-4-one
87. 5-[4-(6-acetoxy-2-methylchroman-2-ylmethoxy)benzyl]-2-iminothiazolidin-4-one
88. 5-[4-(2-ethyl-5,7,7-trimethyl-6-phenylacetoxychroman-2-ylmethoxy)benzyl]-2-iminothiazolidin-4-one
89. 5-[4-(6-cinnamoyloxy-7,8-dimethoxy-2,5-dimethylchroman-2-ylmethoxy)benzyl]-2-iminothiazolidin-4-one
90. 5-[4-(6-m-chlorobenzoyloxy-7,8-dimethoxy-5-methylchroman-2-ylmethoxy)benzyl]-2-iminothiazolidin-4-one
91. 5-[4-(2-ethyl-7,8-dimethoxy-5-methyl-6-valeryloxychroman-2-ylmethoxy)benzyl]-2-iminothiazolidin-4-one
92. 5-[4-(6-acetoxy-2,7-dimethylchroman-2-ylmethoxy)benzyl]-2-iminothiazolidin-4-one
93. 5-{4-[2-(6-o-methoxybenzoyloxy-2,5,7,8-tetramethylchroman-2-yl)ethoxy]benzyl}-2-iminothiazolidin-4-one
94. 5-{4-[2-(2-methyl-6-pivaloyloxychroman-2-yl)ethoxy]benzyl}-2-iminothiazolidin-4-one
95. 5-{4-[2-(7-t-butyl-2-methyl-6-propionyloxychroman-2-yl)ethoxy]benzyl}-2-iminothiazolidin-4-one
96. 5-{4-[2-(6-ethoxycarbonyloxy-7,8-dimethoxy-2,5-dimethylchroman-2-yl)ethoxy]benzyl}-2-iminothiazolidin-4-one
97. 5-{4-[2-(6-p-chlorophenylacetoxy-2-ethyl-7,8-dimethoxy-5-methylchroman-2-yl)ethoxy]benzyl}-2-iminothiazolidin-4-one
98. 5-{4-[2-(7,8-dimethoxy-5-methyl-6-3'-phenylpropionyloxychroman-2-yl)ethoxy]benzyl}-2-iminothiazolidin-4-one
99. 5-{4-[3-(6-benzyloxycarbonyloxy-2,5,7,8-tetramethylchroman-2-yl)propoxy]benzyl}-2-iminothiazolidin-4-one
100. 5-[4-(6-benzoyloxy-2,5,7,8-tetramethylchroman-2-ylmethoxy)benzyl]-2,4-diiminothiazolidine
101. 5-[4-(6-cyclohexanecarbonyloxy-2,5,7-trimethylchroman-2-ylmethoxy)benzyl]-2,4-diiminothiazolidine
102. 5-[4-(6-acetoxy-7-t-butyl-2-methylchroman-2-ylmethoxy)benzyl]-2,4-diiminothiazolidine
103. 5-[4-(6-acetoxy-2-methylchroman-2-ylmethoxy)benzyl]-2,4-diiminothiazolidine
104. 5-[4-(6-acetoxy-7-t-butylchroman-2-ylmethoxy)benzyl]-2,4-diiminothiazolidine
105. 5-[4-(6-acetoxy-2,7-dimethylchroman-2-ylmethoxy)benzyl]-2,4-diiminothiazolidine
106. 5-[4-(6-acetoxy-7,8-dimethoxy-2,5-dimethylchroman-2-ylmethoxy)benzyl]-2,4-diiminothiazolidine
107. 5-[4-(6-acetoxy-7,8-dimethoxy-5-methylchroman-2-ylmethoxy)benzyl]-2,4-diiminothiazolidine
108. 5-[4-(6-acetoxy-2-ethyl-7,8-dimethoxy-5-methylchroman-2-ylmethoxy)benzyl]-2,4-diiminothiazolidine
109. 5-{4-[2-(6-methoxycarbonyloxy-2,5,7,8-tetramethylchroman-2-yl)ethoxy]benzyl}-2,4-diiminothiazolidine
110. 5-{4-[2-(7-t-butyl-6-cyclopentanecarbonyloxy-2-methylchroman-2-yl)ethoxy]benzyl}-2,4-diiminothiazolidine
111. 5-{4-[2-(6-formyloxy-2-methylchroman-2-yl)ethoxy]benzyl}-2,4-diiminothiazolidine
112. 5-{4-[3-(6-methacryloyloxy-7,8-dimethoxy-2,5-dimethylchroman-2-yl)propoxy]benzyl}-2,4-diiminothiazolidine
113. 5-[4-(6-hydroxy-2,5,7,8-tetramethyl-4-oxochroman-2-ylmethoxy)benzyl]thiazolidine-2,4-dione
114. 5-[4-(4,6-dihydroxy-2,5,7,8-tetramethylchroman-2-ylmethoxy)benzyl]thiazolidine-2,4-dione
115. 5-[4-(6-hydroxy-2,5,7-trimethyl-4-oxochroman-2-ylmethoxy)benzyl]thiazolidine-2,4-dione 116. 5-[4-(7-t-butyl-6-hydroxy-2-methyl-4-oxochroman-2-ylmethoxy)benzyl]thiazolidine-2,4-dione
117. 5-[4-(7-t-butyl-4,6-dihydroxy-2-methylchroman-2-ylmethoxy)benzyl]thiazolidine-2,4-dione
118. 5-[4-(6-hydroxy-2-methyl-4-oxochroman-2-ylmethoxy)benzyl]thiazolidine-2,4-dione
119. 5-[4-(2-ethyl-6-hydroxy-5,7,8-trimethyl-4-oxochroman-2-ylmethoxy)benzyl]thiazolidine-2,4-dione
120. 5-[4-(2-ethyl-4,6-dihydroxy-5,7,8-trimethylchroman-2-ylmethoxy)benzyl]thiazolidine-2,4-dione
121. 5-[4-(6-hydroxy-5,7,8-trimethyl-4-oxochroman-2-ylmethoxy)benzyl]thiazolidine-2,4-dione
122. 5-[4-(6-hydroxy-2,7,8-trimethyl-4-oxochroman-2-ylmethoxy)benzyl]thiazolidine-2,4-dione
123. 5-[4-(6-hydroxy-7-isopropyl-2-methyl-4-oxochroman-2-ylmethoxy)benzyl]thiazolidine-2,4-dione
124. 5-[4-(6-hydroxy-5,7-diisopropyl-2-methyl-4-oxochroman-2-ylmethoxy)benzyl]thiazolidine-2,4-dione
125. 5-[4-(6-hydroxy-2-methyl-4-oxo-7-propylchroman-2-ylmethoxy)benzyl]thiazolidine-2,4-dione
126. 5-{4-[2-(6-hydroxy-2,5,7,8-tetramethyl-4-oxochroman-2-yl)ethoxy]benzyl}thiazolidine-2,4-dione
127. 5-{4-[2-(4,6-dihydroxy-2,5,7,8-tetramethylchroman-2-yl)ethoxy]benzyl}thiazolidine-2,4-dione
128. 5-{4-[2-(6-hydroxy-2,5,7-trimethyl-4-oxochroman-2-yl)ethoxy]benzyl}thiazolidine-2,4-dione
129. 5-{4-[2-(7-t-butyl-6-hydroxy-2-methyl-4-oxochroman-2-yl)ethoxy]benzyl}thiazolidine-2,4-dione
130. 5-{4-[2-(7-t-butyl-4,6-dihydroxy-2-methylchroman-2-yl)ethoxy]benzyl}thiazolidine-2,4-dione
131. 5-{4-[2-(6-hydroxy-2-methyl-4-oxochroman-2-yl)ethoxy]benzyl}thiazolidine-2,4-dione
132. 5-{4-[2-(2-ethyl-6-hydroxy-5,7,8-trimethyl-4-oxochroman-2-yl)ethoxy]benzyl}thiazolidine-2,4-dione
133. 5-{4-[2-(6-hydroxy-5,7,8-trimethyl-4-oxochroman-2-yl)ethoxy]benzyl}thiazolidine-2,4-dione
134. 5-{4-[2-(6-hydroxy-5,7-diisopropyl-2,8-dimethyl-4-oxochroman-2-yl)ethoxy]benzyl}thiazolidine-2,4-dione
135. 5-{4-[2-(6-hydroxy-4-oxo-7-pentyl-2-propylchroman-2-yl)ethoxy]benzyl}thiazolidine-2,4-dione
136. 5-[4-(6-hydroxy-7,8-dimethoxy-2,5-dimethyl-4-oxochroman-2-ylmethoxy)benzyl]thiazolidine-2,4-dione
137. 5-[4-(6-hydroxy-7,8-dimethoxy-5-methyl-4-oxochroman-2-ylmethoxy)benzyl]thiazolidine-2,4-dione
138. 5-[4-(2-ethyl-6-hydroxy-7,8-dimethoxy-5-methyl-4-oxochroman-2-ylmethoxy)benzyl]thiazolidine-2,4-dione
139. 5-[4-(6-hydroxy-2,5-dimethyl-7,8-methylenedioxy-4-oxochroman-2-ylmethoxy)benzyl]thiazolidine-2,4-dione
140. 5-{4-[2-(6-hydroxy-7,8-dimethoxy-2,5-dimethyl-4-oxochroman-2-yl)ethoxy]benzyl}thiazolidine-2,4-dione
141. 5-{4-[3-(6-hydroxy-2,5,7,8-tetramethyl-4-oxochroman-2-yl)propoxy]benzyl}thiazolidine-2,4-dione
142. 5-{4-[3-(7-t-butyl-6-hydroxy-4-oxochroman-2-yl)propoxy]benzyl}thiazolidine-2,4-dione
143. 5-[4-(6-hydroxy-4-oxochroman-2-ylmethoxy)benzyl]thiazolidine-2,4-dione
144. 5-[4-(6-hydroxy-2,7-dimethyl-4-oxochroman-2-ylmethoxy)benzyl]thiazolidine-2,4-dione
145. 5-[4-(6-hydroxy-5,7,8-trimethyl-4-oxo-2-propylchroman-2-ylmethoxy)benzyl]thiazolidine-2,4-dione
146. 5-[4-(7-t-butyl-6-hydroxy-2-isopropyl-4-oxochroman-2-ylmethoxy)benzyl]thiazolidine-2,4-dione
147. 5-[4-(2-butyl-6-hydroxy-5,7,8-trimethyl-4-oxochroman-2-ylmethoxy)benzyl]thiazolidine-2,4-dione
148. 5-[4-(6-hydroxy-2-isobutyl-5,7,8-trimethyl-4-oxochroman-2-ylmethoxy)benzyl]thiazolidine-2,4-dione
149. 5-[4-(4,6-dihydroxy-2-isobutyl-5,7,8-trimethylchroman-2-ylmethoxy)benzyl]thiazolidine-2,4-dione
150. 5-[4-(2-t-butyl)-6-hydroxy-5,7,8-trimethyl-4-oxochroman-2-ylmethoxy)benzyl]thiazolidine-2,4-dione
151. 5-[4-(6-hydroxy-2-isobutyl-7-isopropyl-4-oxochroman-2-ylmethoxy)benzyl]thiazolidine-2,4-dione
152. 5-[4-(6-hydroxy-5,7-dimethyl-4-oxo-2-pentylchroman-2-ylmethoxy)benzyl]thiazolidine-2,4-dione
153. 5-[4-(6-hydroxy-5,7,8-trimethyl-2-pentyl-4-oxochroman-2-ylmethoxy)benzyl]thiazolidine-2,4-dione
154. 5-[4-(6-hydroxy-2-isopentyl-5,7,8-trimethyl-4-oxochroman-2-ylmethoxy)benzyl]thiazolidine-2,4-dione
155. 5-{4-[6-hydroxy-5,7,8-trimethyl-2-(2-methylbutyl)-4-oxochroman-2-ylmethoxy]benzyl}thiazolidine-2,4-dione
156. 5-{4-[2-(2,2-dimethylpropyl)-6-hydroxy-5,7,8-trimethyl-4-oxochroman-2-ylmethoxy]benzyl}thiazolidine-2,4-dione
157. 5-[4-(6-hydroxy-2,5,7,8-tetramethyl-4-oxochroman-2-ylmethoxy)benzyl]-2-iminothiazolidin-4-one
158. 5-[4-(6-hydroxy-5,7-diisopropyl-2-methyl-4-oxochroman-2-ylmethoxy)benzyl]-2-iminothiazolidin-4-one
159. 5-[4-(7-t-butyl-6-hydroxy-2-methyl-4-oxochroman-2-ylmethoxy)benzyl]-2-iminothiazolidin-4-one
160. 5-[4-(6-hydroxy-2-methyl-4-oxochroman-2-ylmethoxy)benzyl]-2-iminothiazolidin-4-one
161. 5-[4-(2-ethyl-6-hydroxy-5,7,8-trimethyl-4-oxochroman-2-ylmethoxy)benzyl]-2-iminothiazolidin-4-one
162. 5-[4-(6-hydroxy-2-isobutyl-5,7,8-trimethyl-4-oxochroman-2-ylmethoxy)benzyl]-2-iminothiazolidin-4-one
163. 5-[4-(6-hydroxy-7,8-dimethoxy-2,5-dimethyl-4-oxochroman-2-ylmethoxy)benzyl]-2-iminothiazolidin-4-one
164. 5-[4-(6-hydroxy-5,7,8-trimethyl-4-oxochroman-2-ylmethoxy)benzyl]-2-iminothiazolidin-4-one
165. 5-[4-(2-ethyl-6-hydroxy-7,8-dimethoxy-5-methyl-4-oxochroman-2-ylmethoxy)benzyl]-2-iminothiazolidin-4-one
166. 5-[4-(6-hydroxy-2,7-dimethyl-4-oxochroman-2-ylmethoxy)benzyl]-2-iminothiazolidin-4-one
167. 5-{4-[2-(6-hydroxy-2,5,7,8-tetramethyl-4-oxochroman-2-yl)ethoxy]benzyl}-2-iminothiazolidin-4-one
168. 5-{4-[2-(6-hydroxy-2-methyl-4-oxochroman-2-yl)ethoxy]benzyl}-2-iminothiazolidin-4-one
169. 5-{4-[2-(7-t-butyl-6-hydroxy-2-methyl-4-oxochroman-2-yl)ethoxy]benzyl}-2-iminothiazolidin-4-one
170. 5-{4-[2-(6-hydroxy-7,8-dimethoxy-2,5-dimethyl-4-oxochroman-2-yl)ethoxy]benzyl}-2-iminothiazolidin-4-one
171. 5-{4-[2-(2-ethyl-6-hydroxy-7,8-dimethoxy-5-methyl-4-oxochroman-2-yl)ethoxy]benzyl}-2-iminothiazolidin-4-one
172. 5-{4-[2-(6-hydroxy-7,8-dimethoxy-5-methyl-4-oxochroman-2-yl)ethoxy]benzyl}-2-iminothiazolidin-4-one
173. 5-{4-[3-(6-hydroxy-2,5,7,8-tetramethyl-4-oxochroman-2-yl)propoxy]benzyl}-2-iminothiazolidin-4-one
174. 5-[4-(6-hydroxy-2,5,7,8-tetramethyl-4-oxochroman-2-ylmethoxy)benzyl]-2,4-diiminothiazolidine
175. 5-[4-(6-acetoxy-2,5,7,8-tetramethyl-4-oxochroman-2-ylmethoxy)benzyl]thiazolidine-2,4-dione 176. 5-[4-(6-acetoxy-4-hydroxy-2,5,7,8-tetramethylchroman-2-ylmethoxy)benzyl]thiazolidine-2,4-dione
177. 5-[4-(4,6-diacetoxy-2,5,7,8-tetramethylchroman-2-ylmethoxy)benzyl]thiazolidine-2,4-dione
178. 5-[4-(6-acetoxy-4-benzoyloxy-2,5,7,8-tetramethylchroman-2-ylmethoxy)benzyl]thiazolidine-2,4-dione
179. 5-[4-(4-acetoxy-6-benzoyloxy-2,5,7,8-tetramethylchroman-2-ylmethoxy)benzyl]thiazolidine-2,4-dione
180. 5-[4-(4,6-dibenzoyloxy-2,5,7,8-tetramethylchroman-2-ylmethoxy)benzyl]thiazolidine-2,4-dione
181. 5-[4-(2-ethyl-4,6-diisobutyryloxy-5,7,8-trimethylchroman-2-ylmethoxy)benzyl]thiazolidine-2,4-dione
182. 5-[4-(4,6-dibutyryloxy-2,5,7,8-tetramethylchroman-2-ylmethoxy)benzyl]thiazolidine-2,4-dione
183. 5-{4-[2-(6-m-fluorobenzoyloxy-4-heptanoyloxy-2,5,7-trimethylchroman-2-yl)ethoxy]benzyl}thiazolidine-2,4-dione
184. 5-{4-[2-(4,6-diacryloyloxy-7-t-butyl-2-methylchroman-2-yl)ethoxy]benzyl}thiazolidine-2,4-dione
185. 5-{4-[2-(4-m-fluorobenzoyloxy-6-heptanoyloxy-2-methylchroman-2-yl)ethoxy]benzyl}thiazolidine-2,4-dione
186. 5-{4-[2-(5,7,8-trimethyl-4,6-bis{3-thenoxyloxy}chroman-2-yl)ethoxy]benzyl}thiazolidine-2,4-dione
187. 5-{4-[2-(4,6-bis{2-furoyloxy}-5,7-diisopropyl-2,8-dimethylchroman-2-yl)ethoxy]benzyl}thiazolidine-2,4-dione
188. 5-[4-(2,5,7,8-tetramethyl-4,6-dinicotinoyloxychroman-2-ylmethoxy)benzyl]thiazolidine-2,4-dione
189. 5-{4-[4,6-bis(3,5-dichlorobenzoyloxy)-7,8-dimethoxy-5-methylchroman-2-ylmethoxy]benzyl}thiazolidine-2,4-dione
190. 5-[4-(2-ethyl-7,8-dimethoxy-5-methyl-4,6-divaleryloxychroman-2-ylmethoxy)benzyl]thiazolidine-2,4-dione
191. 5-{4-[7-t-butyl-6-(3,5-di-t-butyl-4-hydroxybenzoyloxy)-2-methyl-4-oxochroman-2-ylmethoxy]benzyl}thiazolidine-2,4-dione
192. 5-[4-(2-ethyl-5,7,8-trimethyl-4-oxo-6-phenylacetoxychroman-2-ylmethoxy)benzyl]thiazolidine-2,4-dione
193. 5-[4-(6-cinnamoyloxy-7,8-dimethoxy-2,5-dimethyl-4-oxochroman-2-ylmethoxy)benzyl]thiazolidine-2,4-dione
194. 5-[4-(6-m-chlorobenzoyloxy-7,8-dimethoxy-5-methyl-4-oxochroman-2-ylmethoxy)benzyl]thiazolidine-2,4-dione
195. 5-[4-(2-ethyl-7,8-dimethoxy-5-methyl-4-oxo-6-valeryloxychroman-2-ylmethoxy)benzyl]thiazolidine-2,4-dione
196. 5-{4-[2-(6-o-methoxybenzoyloxy-2,5,7,8-tetramethyl-4-oxochroman-2-yl)ethoxy]benzyl}-2-iminothiazolidin-4-one
197. 5-{4-[2-(2-methyl-4-oxo-6-pivaloyloxychroman-2-yl)ethoxy]benzyl}thiazolidine-2,4-dione
198. 5-{4-[2-(7-t-butyl-2-methyl-4-oxo-6-propionyloxychroman-2-yl)ethoxy]benzyl}thiazolidine-2,4-dione
199. 5-{4-[2-(6-ethoxycarbonyloxy-7,8-dimethoxy-2,5-dimethyl-4-oxochroman-2-yl)ethoxy]benzyl}thiazolidine-2,4-dione
200. 5-{4-[2-(6-p-chlorophenylacetoxy-2-ethyl-7,8-dimethoxy-5-methyl-4-oxochroman-2-yl)ethoxy]benzyl}thiazolidine-2,4-dione
201. 5-[4-{2-[7,8-dimethoxy-5-methyl-4-oxo-6-(3-phenylpropionyloxy)chroman-2-yl]ethoxy}benzyl]thiazolidine-2,4-dione
202. 5-[4-(6-cyclohexanecarbonyloxy-2,5,7,8-tetramethyl-4-oxochroman-2-ylmethoxy)benzyl]-2,4-diiminothiazolidine
203. 5-[4-(6-acetoxy-2,5,7,8-tetramethyl-4-oxochroman-2-ylmethoxy)benzyl]-2-iminothiazolidin-4-one
204. 5-[4-(6-acetoxy-7-t-butyl-2-methyl-4-oxochroman-2-ylmethoxy)benzyl]-2-iminothiazolidin-4-one
205. 5-[4-(6-acetoxy-5,7,8-trimethylchroman-2-ylmethoxy)benzyl]-2-iminothiazolidin-4-one
206. 5-{4-[2-(6-acetoxy-7-t-butyl-2-methylchroman-2-yl)ethoxy]benzyl}-2-iminothiazolidin-4-one
207. 5-{4-[2-(6-acetoxy-7,8-dimethoxy-2,5-dimethylchroman-2-yl)ethoxy]benzyl}-2-iminothiazolidin-4-one
208. 5-{4-[2-(2,5,7,8-tetramethyl-6-nicotinoyloxychroman-2-yl)ethoxy]benzyl}thiazolidine-2,4-dione Of the compounds listed above, preferred compounds are Compounds No. 1, 5, 6, 11, 13, 23, 27, 30, 34, 36, 38, 40, 42, 62, 63, 67, 75, 113, 116, 148, 157, 159, 162, 175, 205, 206, and 207. More preferred compounds are Compounds No. 1, 5, 13, 30, 62, 67, 113 and 116 and the most preferred compounds are Compounds No. 1 and 62.

Various of the compounds of the invention can exist in the form of tautomers. For example, those compounds of the invention in which Z represents an imino group and Y represents an oxygen atom can exist in the form of the tautomers (IV), (IVa) and (IVb):

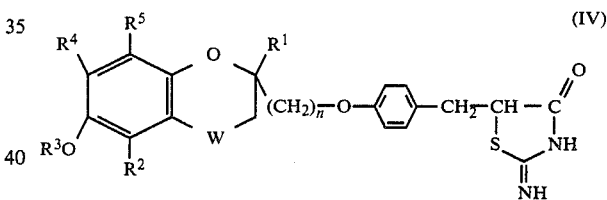

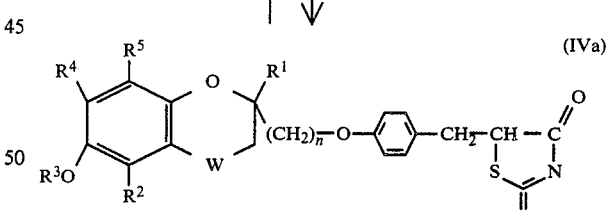

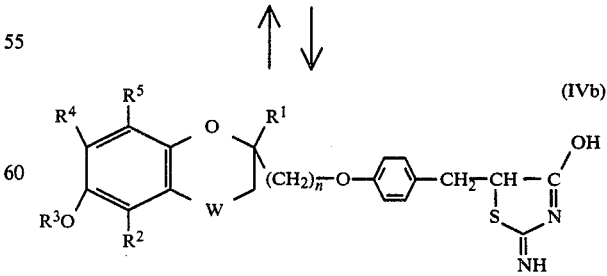

Compounds in which both Y and Z represent imino groups can exist in the form of the tautomers (V), (Va) and (Vb):

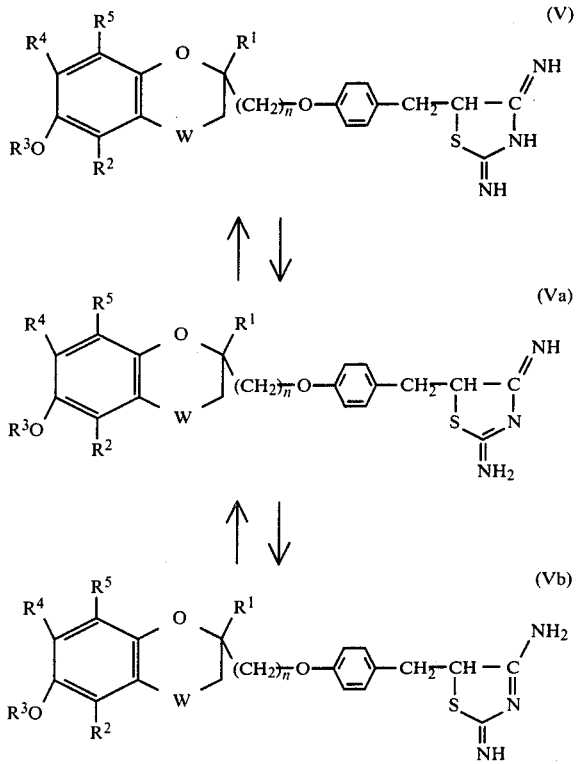

compounds in which Y and Z both represent oxygen atoms can exist in the form of the tautomers (VI), (VIa) and (VIb):

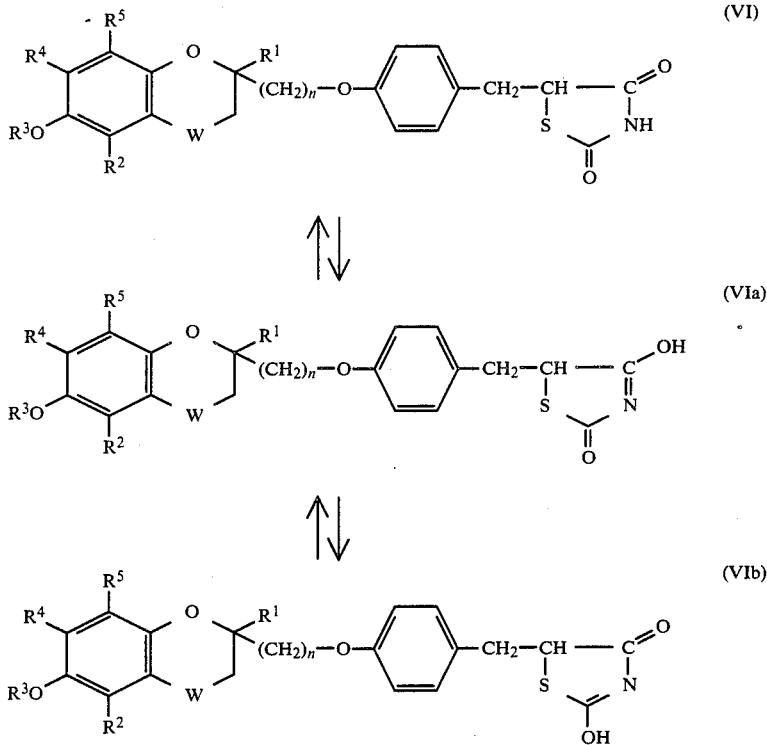

For convenience, all of the tautomers are represented by a single formula, but the tautomeric nature of these compounds should be remembered, as it can have an effect upon various of the properties of the compounds, including their salt-forming ability, as discussed hereafter.

In addition, the compounds of the invention can exist in the form of various stereoisomers. For example, where W represents a $>C=O$ or $-CH_2-$ group, the carbon atoms at the 2-position of the chroman ring and the 5-position of the thiazolidine ring are both asymmetric. Furthermore, where W represents a $>CH-OR^6$ group, the carbon atoms at the 2- and 4-positions of the chroman ring and at the 5-position of the thiazolidine ring are asymmetric. All of these thus give rise to the possibility of stereoisomers. All of the isomers are represented herein by a single formula, and the present invention envisages both mixtures of the isomers and the individual isomers, which may be separated from each other by conventional means.

The compounds of the present invention also include salts of compounds of the invention described above, which may be salts with cations. Cations with which the compounds of the invention may form salts include: alkali metals, such as sodium or potassium; alkaline earth metals, such as calcium; and trivalent metals, such as aluminum.

It will, however, be appreciated that the particular nature of the salt employed is not critical to the present invention and any cations known in the art for forming salts of this type may equally be used in the present invention. The only constraint is that the cations should not, or should not to an unacceptable extent, increase the toxicity or reduce the activity of the resulting compound.

Because the compounds of the invention contain a number of salt-forming centres, mono- and di-salts may be formed. For example, because of the tautomerism described above in relation to the compounds of formula (VI), there are two potential salt-forming reactive sites at the oxygen atom in the group —OR³ and the nitrogen atom at the 3-position of the thiazolidine ring.

PREPARATION OF NEW COMPOUNDS

Step (a)

Compounds of the invention in which Z represents an imino group, that is to say compounds of formula (III):

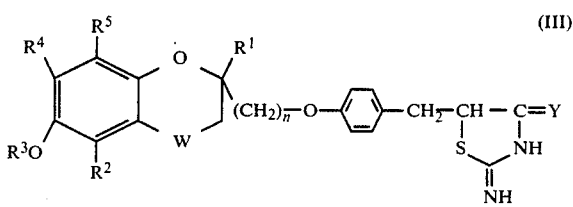

(in which $R^1$-$R^5$, n, W and Y are as defined above) may be prepared by reacting a compound of formula (II):

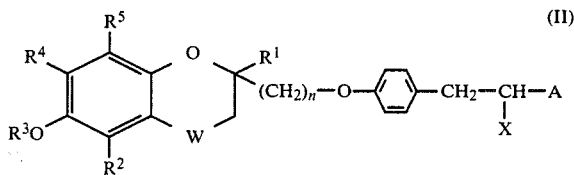

[in which $R^1$-$R^5$ and n are as defined above, A represents a cyano group, a carboxy group, an alkoxycarbonyl group, a carbamoyl group or a group of formula —COO(M)$_m$, in which M represents a cation and m is the reciprocal of its valency, and X represents a halogen atom] with thiourea.

Where A represents a cyano group, the product is a compound in which Y represents an imino group; where A represents a carboxy, alkoxycarbonyl, carbamoyl or —COO(M)$_m$ group, the product is a compound where Y represents an oxygen atom.

In the above formula (II), where A represents an alkoxycarbonyl group, this is preferably a ($C_1$-$C_6$ alkoxy)carbonyl group, for example a methoxycarbonyl, ethoxycarbonyl, propoxycarbonyl, isopropoxycarbonyl or butoxycarbonyl group. M preferably represents a metal atom, such as a sodium, potassium, calcium or aluminum atom, or an ammonium group. X preferably represents a chlorine, bromine or iodine atom.

This reaction is preferably applied only to those compounds where W represents a —$CH_2$— or >C=O group, compounds in which W represents a >CH—$OR^6$ group being prepared from the corresponding compound where W represents a >C=O group, as explained hereafter.

Reaction of the compound of formula (II) with thiourea is preferably effected in the presence of a solvent, the nature of which is not critical, provided that it has no adverse effect on the reaction. Suitable solvents include: alcohols, such as methanol, ethanol, propanol, butanol or ethylene glycol monomethyl ether; ethers, such as tetrahydrofuran or dioxane; ketones, such as acetone; dimethyl sulfoxide; sulfolane; or amides, such as dimethylformamide.

There is no particular limitation on the molar ratio of the compound of formula (II) to thiourea; however, we would normally prefer to use equimolar amounts of a molar excess of thiourea, preferably a slight molar excess. In general, from 1 to 2 moles of thiourea per mole of the compound of formula (II) are preferred.

The various reaction conditions, such as the reaction temperature and time, will vary, depending upon the natures of the starting materials and the solvent; however, the reaction is normally effected at the reflux temperature of the solvent or at a temperature of from 80° to 150° C. for a period of from 1 to 20 hours.

The resulting compound of formula (III) may be the desired final product of the present invention, in which case it may be isolated from the reaction mixture by conventional means, as discussed hereafter. Alternatively, with or without isolation and/or purification, the compound of formula (III) may be subjected to one or both of steps (b) and (c), in any order, and, if desired, step (c) may be followed by step (d). The product of any of these steps may be subjected to the salification reaction discussed in step (e).

Step (b)

In this step, the compound of formula (III), that is to say a compound of formula (I) in which Z represents an imino group, may be hydrolysed to give the corresponding compound of formula (I) in which Z represents an oxygen atom, that is to say a compound of formula (VII):

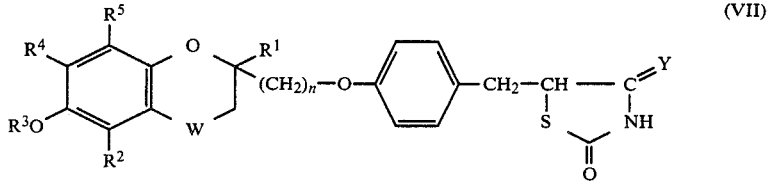

(in which $R^1$-$R^5$, n, W and Y are as defined above).

The hydrolysis reaction is preferably carried out by heating the compound of formula (III) in a suitable solvent with water and an organic acid (such as acetic acid) or a mineral acid (such as sulfuric acid or hydrochloric acid). The nature of the solvent is not critical to the invention, provided that it has no adverse effect upon the reaction; suitable solvents include: sulfolane; and alcohols, such as methanol, ethanol or ethylene glycol monomethyl ether.

The amount of acid used is preferably from 0.1 to 10 moles, more preferably from 0.2 to 3 moles, per mole of the compound of formula (III). The water or aqueous solvent is preferably employed in a large molar excess over the compound of formula (III).

Although not critical, the temperature employed for the reaction is preferably from 50° to 100° C. and the time required for the reaction is normally from 2 to 20 hours.

Where Y in the compound of formula (III) represents an imino group, the hydrolysis of the present step will normally likewise convert said imino group to an oxygen atom, the product being a compound in which both Y and Z are oxygen atoms. However, by careful control of the hydrolysis conditions, it is possible to prevent the hydrolysis reaction going to completion, in which case part of the product will be a compound in which Y represents an imino group and Z represents an oxygen atom.

In addition to converting the imino group represented by Z to an oxygen atom, where $R^3$ in the compound of formula (III) represents an acyl group, the hydrolysis reaction may convert this to a hydrogen atom, although it is possible to maintain the acyl group represented by $R^3$ intact, provided that appropriate reaction conditions are chosen, as is well-known in the art.

Where the compound of formula (VII) is a compound in which $R^3$ represents a hydrogen atom, this may be acylated to give a corresponding compound in which $R^3$ represents one of the acyl groups defined above.

This acylation reaction may be carried out at any suitable stage in the reaction sequence and may, if desired, be carried out simultaneously with the acylation reaction of step (d), as described hereafter. Where, however, the acylation reaction is carried out separately from step (d), the conditions are preferably as follows:

The acylating agent is preferably an acid halide or an acid anhydride, or it may be an organic acid, such as an aromatic carboxylic acid or an aliphatic carboxylic acid, in association with a dehydrating agent or dehydrating catalyst such as a mineral acid (e.g. hydrochloric acid or sulfuric acid) or an organic acid (e.g. p-toluenesulfonic acid).

The reaction is normally carried out in the presence of a solvent, the nature of which is not critical, provided that it has no adverse effect upon the reaction. Suitable solvents include: ethers, such as diethyl ether, tetrahydrofuran or dioxane; aromatic hydrocarbons, such as benzene or toluene; aliphatic hydrocarbons, such as hexane, cyclohexane or heptane; halogenated hydrocarbons, such as methylene chloride or chloroform; ketones, such as acetone or methyl ethyl ketone; amides, such as dimethylformamide or dimethylacetamide; organic bases, such as pyridine or triethylamine; sulfoxides, such as dimethyl sulfoxide; sulfones, such as sulfolane; or water; a single one of these solvents or a mixture of any two or more thereof may be employed.

The ratio of the amount of the compound of formula (VII) in which $R^3$ represents a hydrogen atom to the amount of acylating agent is not particularly critical, but the use of a slight molar excess of the acylating agent over the compound of formula (VII) may be desirable. In general, we prefer to employ from 1 to 2 moles of acylating agent per mole of compound of formula (VII).

The reaction conditions, such as the reaction temperature and reaction time, will vary, depending upon a number of factors, including the nature of the starting materials and solvent, but the reaction is generally carried out at a temperature of from 0° to 100° C. for a period of from several minutes to about 20 hours.

Step (c)

Compounds of formula (I) in which W represents a group of formula >CH—OH, that is to say compounds of formula (Id):

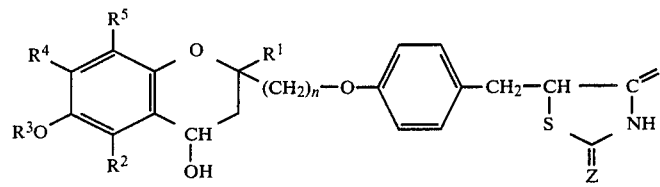

(in which $R^1$–$R^5$, n, Y and Z are as defined above) may be prepared by reducing the corresponding compound in which W represents a group of formula >C=O, that is to say a compound of formula (Ib):

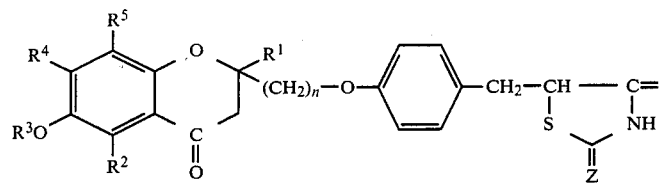

(in which $R^1$–$R^5$, n, Y and Z are as defined above).

The reducing agent employed for this reaction is any one which is capable of reducing a ring carbonyl group to a >CH—OH group without affecting, or affecting to a substantial degree, the remainder of the molecule. Suitable reducing agents include borohydrides, such as sodium borohydride, or K-Selectride, especially sodium borohydride.

The reaction is preferably effected in the presence of a solvent, the nature of which is not critical, provided that it has no adverse effect upon the reaction. Suitable solvents include, for example: alcohols, such as methanol, ethanol, propanol, butanol or ethylene glycol monomethyl ether; and ethers, such as tetrahydrofuran or dioxane.

The molar ratio of the compound of formula (Ib) to the reducing agent is not critical, however we prefer to employ a molar excess of reducing agent, preferably from 1 to 20 moles of reducing agent (especially sodium borohydride) per mole of compound of formula (Ib).

The reaction conditions, particularly the reaction temperature and time, will vary depending upon a number of factors, especially the natures of the starting material, solvent and reducing agent. However, the reaction is normally carried out at a temperature of from 0° to 100° C. for a period of from 1 to about 20 hours.

Step (d)

Optionally, compounds of formula (I) in which W represents a group of formula >CH—OR$^{6'}$ (in which R$^{6'}$ represents any one of the groups defined for R$^6$ but not the hydrogen atom), that is to say compounds of formula (Ie):

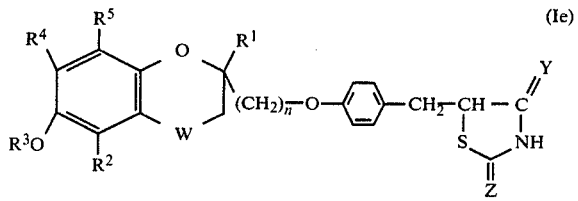

(in which R$^1$-R$^5$, R$^{6'}$, n, Y and Z are as defined above) may be prepared by acylating the corresponding compound of formula (Id), prepared as described in step (c).

The acylating agent is preferably an acid halide or acid anhydride, the parent acid of which will depend upon the acyl group R$^{6'}$ which is desired to be introduced into the compound.

The acylation reaction is preferably effected in the presence of a solvent, the nature of which is not critical, provided that it has no adverse effect upon the reaction. Examples of suitable solvents include: ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, such as methylene chloride or chloroform; organic bases, such as pyridine or triethylamine; amides, such as dimethylformamide or dimethylacetamide; sulfoxides, such as dimethyl sulfoxide; and sulfones, such as sulfolane.

The ratio of the amount of compound of formula (Id) to the acylating agent is not particularly critical and we therefore prefer to employ a slight molar excess of acylating agent over compound (Id). In general, from 1 to 2 moles of acylating agent are employed per mole of compound of formula (Id).

The reaction conditions, particularly reaction temperature and time, will vary depending upon a number of factors, especially the natures of the starting material, acylating agent and solvent, but we normally prefer to carry out the reaction at a temperature of from 0° to 100° C. for a period of from several minutes to about 20 hours.

Step (e)

The compounds of the invention, prepared as described in any of the above steps may be converted to their salts by conventional means, for example by reaction with a basic compound of an alkali metal (such as sodium or potassium), an alkaline earth metal (such as calcium) or a trivalent metal (such as aluminum). Preferred such compounds are sodium hydroxide, potassium hydroxide, sodium ethoxide and potassium t-butoxide.

It will be appreciated that the compounds produced in all of the above steps can exist in various tautomeric forms, as illustrated in relation to compounds (IV), (V) and (VI).

The compounds prepared as described in any of the above steps may be separated after that step and, if desired, purified by conventional means. Suitable isolation and purification steps include concentration of the reaction mixture by evaporating off the solvent under reduced pressure, extraction with a suitable solvent, recrystallization, transfer into another solvent, chromatography and optical resolution. However, where two or more of the above steps are to be carried out, they may, if desired, be carried out without intermediate isolation or purification.

PREPARATION OF STARTING MATERIALS

The α-halocarboxylic acid derivatives of formula (II), which are the principal starting materials for preparing the compounds of the invention, are novel compounds and may be prepared by Methods A and B described below.

Method A

Compounds of formula (II) in which W represents a —CH$_2$— group may be prepared by the sequence of reactions illustrated in the following reaction scheme:

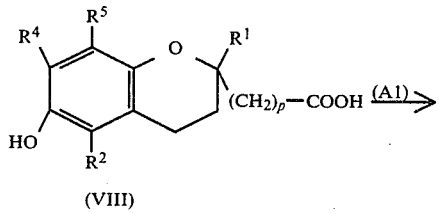

(VIII)

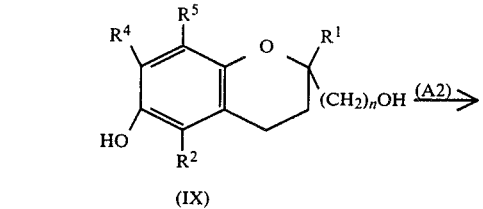

(IX)

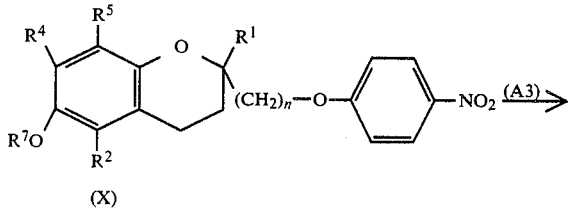

(X)

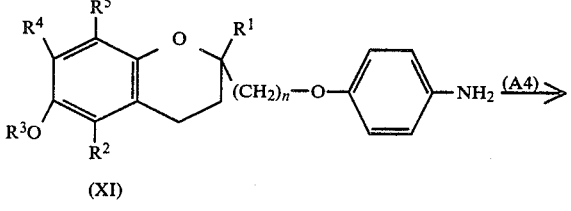

(XI)

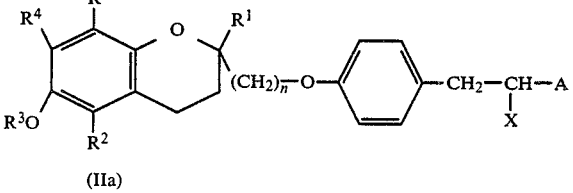

(IIa)

In the above formulae, R$^1$-R$^5$, n, A and X are as defined above, p=(n−1); and R$^7$ represents a hydroxy-protecting group.

Step (A1)

The chroman carboxylic acid homologs (VIII), which are the starting materials for this Method, may be prepared as described, for example, in the Journal of the American Oil Chemical Society, 51, 200 (1974).

These acids (VIII) are reduced with a reducing agent, such as lithium aluminum hydride or Vitride [sodium bis(2-methoxyethoxy)aluminum hydride], to give the corresponding chroman alcohol homolog (IX). This reaction is preferably effected in the presence of a solvent, the nature of which is not critical, provided that it does not interfere with the reaction. Suitable solvents include: ethers, such as diethyl ether, tetrahydrofuran or ethylene glycol dimethyl ether; aromatic hydrocarbons, such as benzene, toluene or xylene; and aliphatic hydrocarbons, such as hexane, heptane, cyclohexane, petroleum ether, ligroin or ethylcyclohexane.

The ratio of the amount of acid (VIII) to reducing agent is not particularly critical, but we generally prefer to use a slight molar excess of reducing agent. Preferably the amount of reducing agent is from 1 to 2 moles per mole of acid (VIII). The reaction conditions, particularly the reaction temperature and time, will vary depending upon a number of factors, such as the nature of the starting material, the reducing agent and the solvent, but the reaction is generally carried out at a temperature of from 10° to 100° C. for a period of from 10 minutes to 20 hours.

Alternatively, the chroman alcohol homolog (IX) may be prepared by reacting a hydroquinone with a compound of formula (XII):

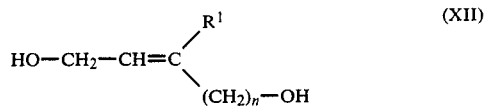

(XII)

(in which n and $R^1$ are as defined above), e.g. a compound of formula (XIIa):

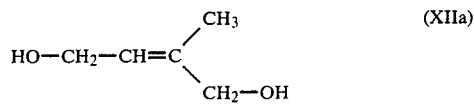

(XIIa)

in the presence of aluminum chloride, as described in West German Pat. No. 3,010,504.

Step (A2)

The chroman alcohol homologs of formula (IX) obtained in step (A1) may be converted to the corresponding nitrophenoxyalkyl chroman compounds (X). However, before carrying out this reaction, we prefer that the phenolic hydroxy group should be protected by a hydroxy-protecting group $R^7$.

The nature of the hydroxy-protecting group is not critical and any such group commonly used in this type of reaction and compound may be employed. Suitable groups include: alkoxyalkyl groups, such as the methoxymethyl group; aralkyl groups, such as the benzyl group; the 2-tetrahydropyranyl group; and acyl groups, such as the acetyl or benzoyl groups. The alkoxyalkyl groups are preferred. The reaction is normally effected by contacting a compound $R^7X$ (in which $R^7$ is as defined above and X represents a halogen atom, preferably a chlorine atom), such as chloromethyl methyl ether or benzyl chloride, with the compound of formula (IX) in the presence of a base such as an alkali metal or alkaline earth metal hydride (e.g. sodium hydride or calcium hydride) or an alkali metal alkoxide (e.g. sodium methoxide, sodium ethoxide or potassium t-butoxide). The reaction is normally carried out in the presence of a solvent, for example; an ether, such as diethyl ether, tetrahydrofuran or dioxane; an aromatic hydrocarbon, such as benzene, toluene or xylene; an aliphatic hydrocarbon, such as hexane or heptane; an amide, such as dimethylformamide or dimethylacetamide; a sulfoxide, such as dimethyl sulfoxide; or a sulfone, such as sulfolane. There is no particular limitation on the molar ratio of compound (IX) to the compound $R^7X$, but we generally prefer to use a slight molar excess of the compound (IX), in order to reduce the risk of protecting the hydroxy group in the side chain at the 2-position. In general, we prefer to employ from 0.8 to 1 mole of the compound $R^7X$ per mole of the compound (IX). The reaction conditions, particularly the reaction temperature and time, may vary depending upon a number of factors, especially the nature of the starting material, the compound $R^7X$ and the solvent, but we normally prefer a reaction temperature of from 0° to 50° C. and a time of from several minutes to several tens of minutes.

The protected chroman alcohol produced by this reaction can, if desired, be isolated and purified, but it may be, and preferably is, converted to the nitrophenoxyalkylchroman compound of formula (X) without intermediate isolation.

Conversion to the compound of formula (X) is effected by reacting the protected compound (IX) with a 4-halonitrobenzene in the presence of a base, such as sodium hydride, in a solvent, such as dimethyl sulfoxide or dimethylformamide. The amount of 4-halonitrobenzene employed is preferably about 2 moles per mole of protected compound (IX). The reaction temperature is preferably from 30° to 100° C. and the time required for the reaction is usually from several minutes to several hours.

Step (A3)

The nitro compound of formula (X) thus obtained is reduced in this step to the corresponding amino compound of formula (XI). In the course of or before or after this reduction, the protecting group $R^7$ may be allowed to remain as it is, removed or converted to another group (particularly an acryl group, such as an acetyl or benzoyl group).

When deprotection of the compound (X) is desired, this can easily be achieved by reacting the compound (X) with a dilute aqueous acid (such as hydrochloric acid, sulfuric acid or nitric acid) to hydrolyse the protecting group. The reaction is normally carried out in the presence of a solvent, for example: an alcohol, such as methanol, ethanol or propanol; an ether, such as tetrahydrofuran or dioxane; a ketone, such as acetone or methyl ethyl ketone; an organic acid, such as acetic acid or propionic acid; dimethyl sulfoxide; dimethylformamide; or water. Of these, water or an organic acid is preferred. The amount of acid used for hydrolysis is preferably from 0.01 to 5 moles, more preferably from 0.01 to 1 mole, per mole of the compound (X). We prefer to carry out the reaction in the presence of a large molar excess of water or of acetic acid as the solvent. The reaction temperature is preferably from ambient temperature to 100° C. and the time required for the reaction is normally from several minutes to about 20 hours.

If it is desired to convert the protecting group $R^7$ to another group, particularly an acyl group, this may be achieved by acylation of the deprotected compound obtained as described above. The acylating agent may be an acid halide, such as acetyl chloride or benzoyl chloride, or an acid anhydride, such as acetic anhydride. This reaction is preferably carried out in the presence of an organic amine (such as pyridine or triethylamine) or in the presence of an inorganic base (for example an alkali metal hydroxide, such as sodium hydroxide or potassium hydroxide, or an alkali metal carbonate or bicarbonate, such as sodium carbonate, potassium carbonate or sodium bicarbonate). The acylating reaction is preferably carried out in the presence of a solvent, for example: an aliphatic hydrocarbon, such as hexane, cyclohexane, heptane, ligroin or ethylcyclohexane; an aromatic hydrocarbon, such as benzene, toluene or xylene; an organic amine, such as pyridine or triethylamine; a ketone, such as acetone or methyl ethyl ketone; an amide, such as dimethylformamide; a sulfoxide, such as dimethyl sulfoxide; or water. The ratio of the amount of deprotected compound (X) to acylating agent is not particularly critical, however, a slight molar excess of acylating agent is usually preferred, for example from 1 to 1.5 moles of acylating agent per mole of deprotected compound (X). Where an organic amine is employed as the acid-binding agent, it may be employed in any amount from 1 mole to a large molar excess per mole of the compound of formula (X). Where an inorganic base is employed as the acid-binding agent, it is preferably employed in an amount of from 1 to 10 moles per mole of the compound of formula (X). The reaction conditions, particularly the reaction temperature and time, may vary depending upon a number of factors, particularly the natures of the starting material and solvent employed, but the reaction is preferably effected at a temperature of from 0° to 100° C. for a period of from several minutes to 20 hours.

The nitro compound of formula (X) (which may optionally have been subjected to any of the processes described above) is then reduced to the amino compound of formula (XI). The reduction may be a catalytic reduction process employing hydrogen or reduction with a metal (such as zinc or iron) and an acid (which may be a mineral acid such as hydrochloric acid or sulfuric acid or an organic acid such as acetic acid). Preferably a catalytic reduction process is employed. The catalyst employed for this catalytic reduction is preferably palladium-on-carbon, Raney nickel or platinum oxide, of which palladium-on-carbon is particularly preferred. The hydrogen pressure is preferably from 1 to 100 atmospheres (1.01 to 101 bars), more preferably from 1 to 6 atmospheres (1.01 to 6.06 bars). The reaction is preferably effected in the presence of a solvent, the nature of which is not critical, provided that it has no adverse effect upon the reaction. Suitable solvents include: alcohols, such as methanol or ethanol; aromatic hydrocarbons, such as benzene or toluene; ethers, such as tetrahydrofuran; organic acids, such as acetic acid; water; or mixtures of any two or more thereof. The reaction conditions, particularly the reaction temperature and time, may vary depending upon a number of factors, particularly the nature of the starting material, the method employed for reduction and the solvent, but the reaction is normally effected at a temperature from ambient to 50° C. and the period required for the reaction is generally from several minutes to about 20 hours.

Step (A4)

The 2-(4-aminophenoxyalkyl)chroman derivative of formula (XI), prepared as described in step (A3) above, is diazotized and then subjected to a Meerwein arylation, to give the desired α-halocarboxylic acid compound of formula (IIa). The two reactions are preferably effected sequentially in the same reaction system and under essentially the same conditions.

The diazotization reaction comprises reacting the amino compound of formula (IX) with a nitrite (such as sodium nitrite) in the presence of an acid, such as hydrochloric acid or hydrobromic acid.

The Meerwein arylation reaction comprises reacting the resulting diazonium compound with acrylic acid, an acrylic acid ester (such as methyl acrylate or ethyl acrylate) or another acrylic acid derivative (such as acrylonitrile or acrylamide) in the presence of a catalytic amount of a cuprous compound (which may be a salt, such as cuprous chloride, or another cuprous compound such as cuprous oxide). The acrylic acid esters are preferred and the preferred cuprous compound is cuprous oxide.

The reactions are preferably effected in the presence of a solvent, the nature of which is not critical, provided that it does not interfere with the reactions. Suitable solvents include: alcohols, such as methanol or ethanol; ketones, such as acetone or methyl ethyl ketone; water; or a mixture of any two or more thereof. The molar ratio of the amino compound of formula (XI) to the acrylic acid or derivative thereof is preferably from 1:1 to 1:15, more preferably from 1:5 to 1:10. The molar ratio of the amino compound (XI) to the cuprous compound is preferably from 1:0.01 to 1:1, more preferably from 1:0.03 to 1:0.3. The reaction conditions, particularly the reaction temperature and time, may vary depending upon a number of factors, especially the natures of the starting materials and the solvent employed, but the reaction is normally carried out at a temperature from ambient temperature to 100° C., preferably from 30° to 60° C., and the period required for the reaction is normally from about 20 minutes to about 20 hours, more preferably from 30 minutes to 2 hours.

Method B

α-Halocarboxylic acid derivatives of formula (II) in which W represents a >C=O group, that is compounds of formula (IIb), may be prepared as illustrated in the following reaction scheme:

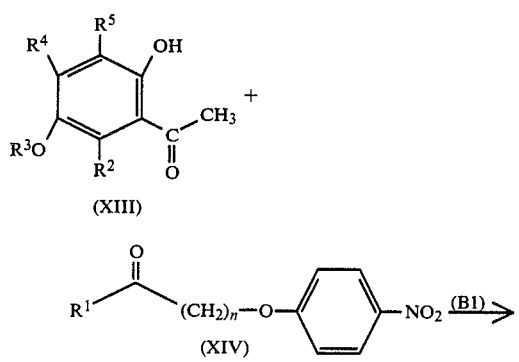

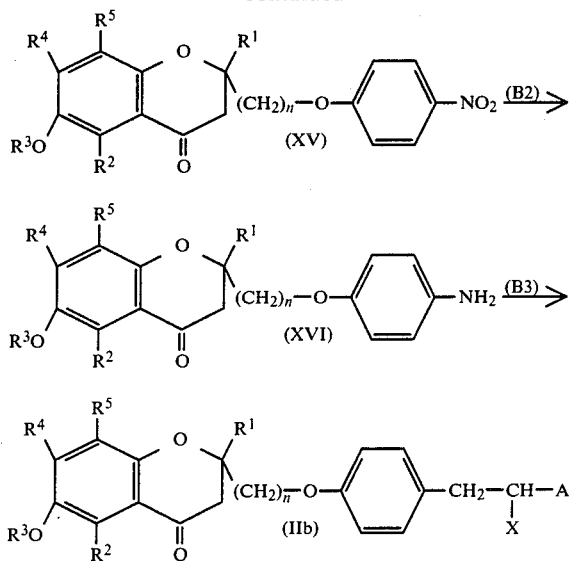

In the above formulae, $R^1$-$R^5$, n, A and X are as defined above. The reaction sequence comprises the following steps:

Step (B1)

The acetophenone derivative of formula (XIII) which is one of the starting materials for this step may be prepared, for example, as described in Chem. Berichte, 95, 1413. The other starting materials, the p-nitrophenoxyalkyl alkyl ketones of formula (XIV), may be prepared, for example, as described in J. Med. Chem., 21, 386 (1978) and J. Am. Chem. Soc., 99, 7653 (1977).

In this step, the compounds (XIII) or (XIV) are reacted together in the presence of a secondary amine, as described, for example, in Japanese Patent Application Kokai No. 19670/77.

The reaction is preferably effected in the presence of a solvent, the nature of which is not critical, provided that it has no adverse effect upon the reaction. Suitable solvents include: aliphatic and aromatic hydrocarbons, such as petroleum ether, benzene, toluene, xylene, hexane and cyclohexane; halogenated aliphatic and aromatic hydrocarbons, such as carbon tetrachloride, methylene chloride, chloroform, chlorobenzene and dichlorobenzene; ethers, such as diethyl ether, tetrahydrofuran and dioxane; amides, such as dimethylformamide, dimethylacetamide and N-methylpyrrolidone; alcohols, such as methanol, ethanol and ethylene glycol monomethyl ether; esters, such as ethyl acetate; nitriles, such as acetonitrile; and sulfoxides, such as dimethyl sulfoxide.

The secondary amine employed in this reaction is preferably a compound of formula $R^9$—NH—$R^{10}$, in which $R^9$ and $R^{10}$ may be the same or different and each represents an alkyl group or $R^9$ and $R^{10}$, together with the nitrogen atom to which they are attached, represent a nitrogen-containing heterocyclic ring system. Examples of such secondary amines include diethylamine, dimethylamine, N-methylpiperazine, pyrrolidine, piperidine or morpholine, of which pyrrolidine is particularly preferred.

The molar ratio of the compound of formula (XIII) to the compound of formula (XIV) is not particularly critical, but, to avoid waste, roughly equimolar amounts of the two compounds are used. In general, the amount of secondary amine is preferably from 0.05 to 1.5 moles, more preferably from 0.1 to 1 mole, per mole of the compound of formula (XIII) or (XIV).

The reaction conditions, particularly reaction temperature and time, may vary depending upon a number of factors, especially the nature of the starting materials and of the solvent, but, in general, we prefer to carry out the reaction at a temperature of from $-30°$ C. to $+150°$ C., more preferably from $10°$ to $120°$ C., for a period of from 30 minutes to 3 days.

Step (B2)

In this step, the nitro compound of formula (XV) prepared as in step (B1) is reduced to the corresponding amino compound of formula (XVI). This reaction is precisely the same as step (A3) of Method A, employing the same reaction conditions and reagents.

Step (B3)

In this step, the amino compound of formula (XVI), obtained as described in step (B2), is diazotized and then subjected to a Meerwein arylation, to give the desired α-halocarboxylic acid derivative of formula (IIb). These reactions are precisely the same as those described in step (A4) of Method A and may be carried out employing the same reagents and reaction conditions.

If desired, the corresponding α-halocarboxylic acid derivative of formula (II) in which W represents a >CH—OH or >CH—$OR^{6'}$ group may be prepared following essentially the same procedures as described in steps (c) and (d) of the process of the present invention; it is, however, much preferred that, instead, the compound of formula (IIb) should be employed as the starting material in the process of the invention and that steps (c) and optionally (d) should be carried out, if desired, as part of the process of the invention.

The compounds of formulae (IIa) and (IIb) prepared as described above in Methods (A) and (B) can, if desired, be converted to various of their hydrolysis products or may be transesterified or converted to salts, for example such metal salts as the sodium, potassium, calcium or aluminum salts. Alternatively, they can be converted from metal salts or from compounds having free hydroxyphenyl groups or free carboxy groups to derivatives thereof, for example as follows:

Compounds in which $R^3$ represents a hydrogen atom and A represents a carboxy group can be prepared by hydrolysis of the corresponding compound of formula (II) in which, for example, $R^3$ represents an acyl group and A represents an alkoxycarbonyl group. This reaction is preferably effected in the presence of a base, for example: an inorganic base, such as an alkali metal carbonate (e.g. sodium carbonate or potassium carbonate) of an alkali metal hydroxide (e.g. sodium hydroxide or potassium hydroxide); or an organic base, such as an alkali metal alkoxide (e.g. sodium methoxide, sodium ethoxide or potassium t-butoxide). The reaction is preferably effected in the presence of a solvent, the nature of which is not critical, provided that it has no adverse effect upon the reaction. Suitable solvents include: lower alcohols, such as methanol or ethanol; ethers, such as tetrahydrofuran or dioxane; water; or mixtures of any two or more thereof.

The molar ratio of the compound of formula (II) to the base is preferably from 1:1 to 1:5, more preferably from 1:2 to 1:3. Although the reaction conditions, particularly the reaction temperature and time, may vary depending upon a number of factors, particularly the natures of the starting material, base and solvent employed, the reaction is generally carried out at a temperature of from $-10°$ C. to $+30°$ C., more preferably from 0° to 10° C. and the reaction time is generally from several minutes to several tens of hours.

The compound of formula (II) in which $R^3$ represents a hydrogen atom and A represents an alkoxycarbonyl group can be prepared by solvolysis of the corresponding compound in which $R^3$ represents an acyl group and A represents an alkoxycarbonyl group. This is carried out in the presence of a base, preferably an alkali metal alkoxide, such as sodium methoxide, sodium ethoxide or potassium t-butoxide. The reaction is preferably effected in the presence of a solvent, for example: an alcohol, such as methanol, ethanol, propanol, isopropanol or t-butanol; an ether, such as tetrahydrofuran or dioxane; or a mixture of any two or more thereof. If the alkoxycarbonyl group represented by A in the starting material is to be kept intact, it is preferred that the alkali metal alkoxide should be the alkoxide corresponding to this alkoxycarbonyl group and that the solvent should be an alcohol, which likewise corresponds to the alkoxycarbonyl group. However, the alkoxycarbonyl group in the starting material may, if desired, be converted into any other alkoxycarbonyl group by suitable choice of the alkali metal alkoxide and the alcohol solvent.

The molar ratio of the compound of formula (II) to the base is preferably from 1:1 to 1:3, more preferably from 1:1 to 1:2. The reaction conditions, especially the reaction temperature and reaction time, may vary, depending upon a number of factors, particularly the natures of the starting materials, bases and solvents employed, but the reaction is preferably carried out at a temperature of from $-10°$ C. to $+30°$ C., more preferably from 0° to 10° C., for a period of from several minutes to several tens of hours.

Compounds of formula (II) in which $R^3$ represents an acyl group and A represents a carboxy group may be prepared by hydrolysis of the corresponding compound of formula (II) in which $R^3$ represents an acyl group and A represents an alkoxycarbonyl group. In this case, the hydrolysis is effected in the presence of an inorganic base (for example an alkali metal carbonate, such as sodium carbonate or potassium carbonate, or an alkali metal hydroxide, such as sodium hydroxide or potassium hydroxide) or in the presence of another base such as an alkali metal alkoxide (for example sodium methoxide, sodium ethoxide or potassium t-butoxide). This reaction is preferably effected in the presence of a solvent, for example: a lower alcohol, such as methanol or ethanol; an ether, such as tetrahydrofuran or dioxane; water; or a mixture of any two or more thereof. The molar ratio of the compound of formula (II) to the base is preferably from 1:1 to 1:5, more preferably from 1:1 to 1:2. The reaction conditions, particularly the reaction temperature and time, may vary depending upon a number of factors, especially the natures of the starting materials, bases and solvents employed, but the reaction is normally effected at a temperature of from $-10°$ C. to $+30°$ C., more preferably from 0° to 10° C. for a period of from several minutes to several tens of hours.

In the α-halocarboxylic acid compounds of formula (II), the carbon atom at the 2-position of the chroman ring and that carbon atom to which the group A and the atom X are both attached are both asymmetric and accordingly give rise to stereoisomers, all of which are represented herein by a single formula. However, of course, the isomers may, if desired, be separated by conventional means and the present invention envisages the use of both individual isomers and mixtures thereof.

The α-halocarboxylic acid compounds of formula (II) have also been observed to lower the level of blood lipid peroxides and, in addition, have the effect of lowering blood triglycerides and blood cholesterol. They can therefore be expected to be useful as antihyperlipemic agents.

Of the compounds of formula (II) which exhibit the therapeutic effects mentioned above and which also form part of the present invention, preferred compounds are those listed below:

1. 2-chloro-3-[4-(6-hydroxy-2,5,7,8-tetramethylchroman-2-ylmethoxy)phenyl]propionic acid
2. 3-[4-(6-acetoxy-2,5,7,8-tetramethylchroman-2-ylmethoxy)phenyl]-2-chloropropionic acid
3. Ethyl 2-chloro-3-[4-(6-hydroxy-2,5,7,8-tetramethylchroman-2-ylmethoxy)phenyl]propionate
4. Ethyl 3-[4-(6-acetoxy-2,5,7,8-tetramethylchroman-2-ylmethoxy)phenyl]-2-chloropropionate
5. Ethyl 3-[4-(6-benzoylozy-2,5,7,8-tetramethylchroman-2-ylmethoxy)phenyl]-2-chloropropionate
6. 3-[4-(7-t-butyl-6-hydroxy-2-methylchroman-2-ylmethoxy)phenyl]-2-chloropropionic acid
7. Ethyl 3-[4-(7-t-butyl-6-hydroxy-2-methylchroman-2-ylmethoxy)phenyl]-2-chloropropionate
8. Ethyl 3-[4-(6-acetoxy-7-t-butyl-2-methylchroman-2-ylmethoxy)phenyl]-2-chloropropionate
9. 2-chloro-3-[4-(6-hydroxy-2-methylchroman-2-ylmethoxy)phenyl]propionic acid
10. Ethyl 3-[4-(6-acetoxy-2-methylchroman-2-ylmethoxy)phenyl]-2-chloropropionate
11. 2-chloro-3-[4-(6-hydroxy-7,8-dimethoxy-2,5-dimethylchroman-2-ylmethoxy)phenyl]propionic acid
12. 3-{4-[2-(6-acetoxy-7,8-dimethoxy-5-methylchroman-2-yl)ethoxy]phenyl}-2-chloropropionic acid
13. Ethyl 2-bromo-3-[4-(2-ethyl-6-hydroxy-7,8-dimethoxy-5-methylchroman-2-ylmethoxy)phenyl]propionate
14. 2-chloro-3-[4-(6-hydroxy-2,7-dimethylchroman-2-ylmethoxy)phenyl]propionic acid
15. Ethyl 2-chloro-3-[4-(6-hydroxy-2,7-dimethylchroman-2-ylmethoxy)phenyl]propionate
16. Ethyl 3-[4-(6-acetoxy-2,7-dimethylchroman-2-ylmethoxy)phenyl]-2-chloropropionate
17. Ammonium 2-chloro-3-{4-[2-(2-ethyl-6-hydroxy-5,7-diisopropylchroman-2-yl)ethoxy]phenyl}propionate
18. 3-{4-[6-(3,5-di-t-butyl-4-hydroxybenzoyloxy)-5,7-diisopropyl-2-methylchroman-2-ylmethoxy]phenyl}-2-chloropropionic acid
19. Sodium 2-chloro-3-{4-[3-(8-ethyl-5,7-diisopentyl-6-p-methylbenzoyloxy-2-propylchroman-2-yl)propoxy]phenyl}propionate
20. Potassium 2-chloro-3-{4-[2-(5,7-dibutyl-6-cyclohexanecarbonyloxy-2-isopropyl-8-propylchroman-2-yl)ethoxy]phenyl}propionate
21. Aluminum tris{3-[4-(2-butyl-6-2'-furoyloxy-7-isopentyl-5,8-dimethylchroman-2-ylmethoxy)phenyl]-2-chloropropionate}
22. 2-chloro-3-{4-[2-(2-isopentyl-5,7-dimethyl-6-phenylacetoxychroman-2-yl)ethoxy]phenyl}propionamide 23. Ethyl 3-[4-(6-acetoxy-2-ethyl-5,7,8-trimethylchroman-2-ylmethoxy)phenyl]-2-chloropropionate
24. Ethyl 3-[4-(6-acetoxy-2-isobutyl-5,7,8-trimethylchroman-2-ylmethoxy)phenyl]-2-chloropropionate
25. 2-chloro-3-[4-(6-hydroxy-2,5,7,8-tetramethyl-4-oxochroman-2-ylmethoxy)phenyl]propionic acid
26. 3-[4-(6-acetoxy-2,5,7,8-tetramethyl-4-oxochroman-2-ylmethoxy)phenyl]-2-chloropropionic acid
27. Ethyl 2-chloro-3-[4-(6-hydroxy-2,5,7,8-tetramethyl-4-oxochroman-2-ylmethoxy)phenyl]propionate
28. Ethyl 3-[4-(6-acetoxy-2,5,7,8-tetramethyl-4-oxochroman-2-ylmethoxy)phenyl]-2-chloropropionate
29. Ethyl 3-[4-(6-benzoyloxy-2,5,7,8-tetramethyl-4-oxochroman-2-ylmethoxy)phenyl]-2-chloropropionate
30. 3-[4-(7-t-butyl-6-hydroxy-2-methyl-4-oxochroman-2-ylmethoxy)phenyl]-2-chloropropionic acid
31. Ethyl 3-[4-(7-t-butyl-6-hydroxy-2-methyl-4-oxochroman-2-ylmethoxy)phenyl]-2-chloropropionate
32. Ethyl 3-[4-(6-acetoxy-7-t-butyl-2-methyl-4-oxochroman-2-ylmethoxy)phenyl]-2-chloropropionate
33. 2-chloro-3-[4-(6-hydroxy-2-methyl-4-oxochroman-2-ylmethoxy)phenyl]propionic acid
34. Ethyl 3-[4-(6-acetoxy-2-methyl-4-oxochroman-2-ylmethoxy)phenyl]-2-chloropropionate
35. 2-chloro-3-[4-(6-hydroxy-7,8-dimethoxy-2,5-dimethyl-4-oxochroman-2-ylmethoxy)phenyl]propionic acid
36. 3-{4-[2-(6-acetoxy-7,8-dimethoxy-5-methyl-4-oxochroman-2-yl)ethoxy]phenyl}-2-chloropropionic acid
37. Ethyl 2-bromo-3-[4-(2-ethyl-6-hydroxy-7,8-dimethoxy-5-methyl-4-oxochroman-2-ylmethoxy)phenyl]propionate
38. 2-chloro-3-[4-(6-hydroxy-2,7-dimethyl-4-oxochroman-2-ylmethoxy)phenyl]propionic acid
39. Ethyl 2-chloro-3-[4-(6-hydroxy-2,7-dimethyl-4-oxochroman-2-ylmethoxy)phenyl]propionate
40. Ethyl 3-[4-(6-acetoxy-2,7-dimethyl-4-oxochroman-2-ylmethoxy)phenyl]-2-chloropropionate
41. Ammonium 2-chloro-3-{4-[2-(2-ethyl-6-hydroxy-5,7-diisopropyl-4-oxochroman-2-yl)ethoxy]phenyl}propionate
42. 2-chloro-3-{4-[6-(3,5-di-t-butyl-4-hydroxybenzoyloxy)-5,7-diisopropyl-2-methyl-4-oxochroman-2-ylmethoxy]phenyl}propionic acid
43. Sodium 2-chloro-3-{4-[3-(8-ethyl-5,7-diisopentyl-6-p-methylbenzoyloxy-4-oxo-2-propylchroman-2-yl)propoxy]phenyl}propionate
44. Potassium 2-chloro-3-{4-[2-(5,7-dibutyl-6-cyclohexanecarbonyloxy-2-isopropyl-4-oxo-8-propylchroman-2-yl)ethoxy]phenyl}propionate
45. Aluminum tris{3-[4-(2-butyl-6-2'-furoyloxy-7-isopentyl-5,8-dimethyl-4-oxochroman-2-ylmethoxy)phenyl]-2-chloropropionate}
46. 2-chloro-3-{4-[2-(2-isopentyl-5,7-dimethyl-4-oxo-6-phenylacetoxychroman-2-yl)ethoxy]phenyl}propionamide
47. 2-chloro-3-[4-(6-hydroxy-2-isobutyl-5,7,8-trimethyl-4-oxochroman-2-ylmethoxy)phenyl]propionic acid The compounds of the invention have been shown to have a very strong ability to lower the level of lipid peroxides, as demonstrated by the test against rat liver microsomal lipid peroxidation described in Biochem. Biophys. Res. Commun., 95, 734 (1980). In addition, in experiments using alloxan-induced hyperlipaemic mice, the compounds have demonstrated the ability to lower blood lipid peroxide, triglyceride and cholesterol levels. Moreover, the compounds of the invention are less toxic than many known compounds to experimental animals such as rats, as assessed by tests in which the appetite, body weight and hepatic enlargement are checked.

Accordingly, it is considered that the compounds of the present invention will be useful for the therapeutic treatment of human hyperlipaemia, diabetes and complications thereof, especially diabetes mellitus. The compounds of the invention may be administered orally, for example in the form of tablets, capsules, powders or granules, or parenterally, for example by injection or in the form of a suppository. The recommended dosage will, of course, vary depending upon the age and body weight of the patient as well as the nature and severity of the disease. However, for an adult human patient, a daily dose of from 50 mg to 5 g (which may be administered in a single dose or in divided doses) is recommended in the treatment of hyperlipaemia, diabetes mellitus and complications thereof.

The following Examples illustrate the preparation of various of the compounds of the present invention, whilst the subsequent Test Examples illustrate the valuable biological properties of these compounds. Preparation of various of the starting materials employed in the Examples is illustrated in the subsequent Preparations.

In the nuclear magnetic resonance spectra reported in the Examples and Preparations, the abbreviation "D" means that the signal disappeared upon the addition of heavy water ($D_2O$), and the abbreviation "nd" means that precise identification of the signal was not possible because of overlap by other signals or the absorption of the solvent.

EXAMPLE 1

(a)

5-[4-(6-Hydroxy-2,5,7,8-tetramethylchroman-2-ylmethoxy)benzyl]-2-iminothiazolidin-4-one A mixture of 9.6 g of ethyl 3-[4-(6-acetoxy-2,5,7,8-tetramethylchroman-2-ylmethoxy)phenyl]-2-chloropropionate, 1.8 g of thiourea and 11 ml of sulfolane was reacted for 80 minutes under a nitrogen stream at 115°–120° C. Subsequently, a mixture of 90 ml of acetic acid, 30 ml of concentrated hydrochloric acid and 15 ml of water was added to this, and the resulting mixture was further heated for 12 hours at 85°–90° C. 27 g of sodium bicarbonate were added to this reaction mixture, and, once evolution of carbon dioxide had ceased, the solvent was distilled off. A 10:1 by volume mixture of benzene and ethyl acetate was added to the residue, and the crude product was washed with a mixture of equal volumes of a saturated aqueous solution of sodium bicarbonate and water. The white powder produced was removed by filtration and washed again with water. It was then recrystallized from acetone to give 2.2 g of 5-[4-(6-hydroxy-2,5,7,8-tetramethylchroman-2-ylmethoxy)benzyl]-2-iminothiazolidin-4-one, melting at 205°–207° C.

Nuclear Magnetic Resonance Spectrum (heptadeuterated dimethylformamide+$D_2O$) δppm: 1.37 (3H, singlet); about 2 (2H, multiplet); 2.02 (3H, singlet); 2.14 (6H, singlet); 2.3–3.1 (solvent absorption); 3.42 (1H, doublet of doublets, J=15 & 4.5 Hz); 4.60 (1H, doublet of doublets, J=9 & 4.5 Hz); 6.93 (2H, doublet, J=9 Hz); 7.23 (2H, doublet, J=9 Hz).

(b)
5-[4-(6-Hydroxy-2,5,7,8-tetramethylchroman-2-ylmethoxy)benzyl]thiazolidine-2,4-dione The organic solution produced by removing the white powder in step (a) above was washed with water and dried over anhydrous sodium sulfate. The solvent was then distilled off. The resulting crude product was purified by column chromatography through silica gel eluted with a mixture of benzene and ethyl acetate first in a volume ratio of 10:1 and then in a volume ratio of 10:1.4. 3.4 g of the desired 5-[4-(6-hydroxy-2,5,7,8-tetramethylchroman-2-ylmethoxy)benzyl]thiazolidine-2,4-dione, melting at 184°–186° C., were obtained from the fractions eluted with the latter mixture.

Nuclear Magnetic Resonance Spectrum (hexadeuterated acetone) $\delta$ ppm: 1.39 (3H, singlet); about 2 (2H, multiplet); 2.02 (3H, singlet); 2.09 (3H, singlet); 2.13 (3H, singlet); 2.63 (2H, broad triplet, J=6 Hz); 3.07 (1H, doublet of doublets, J=15 & 9 Hz); 3.41 (1H, doublet of doublets, J=15 & 4.5 Hz); 3.97 (2H, AB Type, J=9 Hz); 4.70 (1H, doublet of doublets, J=9 & 4.5 Hz); 6.90 (2H, doublet, J=9 Hz); 7.21 (2H, doublet, J=9 Hz).

EXAMPLE 2

5-[4-(6-Hydroxy-2,5,7,8-tetramethylchroman-2-ylmethoxy)benzyl]thiazolidine-2,4-dione 3.1 g of 5-[4-(6-hydroxy-2,5,7,8-tetramethylchroman-2-ylmethoxy)benzyl]-2-iminothiazolidin-4-one [prepared as described in Example 1(a)] were added to a mixture of 45 ml of acetic acid, 15 ml of concentrated hydrochloric acid and 8 ml of water, and the mixture was reacted for 12 hours at 85°–90° C. It was then processed and purified in a similar manner to Example 1(a), giving 2.5 g of 5-[4-(6-hydroxy-2,5,7,8-tetramethylchroman-2-ylmethoxy)benzyl]thiazolidine-2,4-dione, whose melting point and nuclear magnetic resonance spectrum were consistent with those of the product of Example 1(b).

EXAMPLE 3

(a) Benzene mono adduct of 5-[4-(6-acetoxy-2,5,7,8-tetramethylchroman-2-ylmethoxy)benzyl]thiazolidine-2,4-dione 0.725 g of 5-[4-(6-hydroxy-2,5,7,8-tetramethylchroman-2-ylmethoxy)benzyl]thiazolidine-2,4-dione was dissolved in 4 ml of benzene; 400 mg of dry pyridine were added; 0.2 g of acetic anhydride was added dropwise under a nitrogen stream at 5°–10° C.; and the mixture was reacted for 2 days at room temperature. The resulting white crystals were separated by filtration, washed with benzene and vacuum-dried for 30 minutes at 90° C., giving 0.74 g of the benzene mono adduct of 5-[4-(6-acetoxy-2,5,7,8-tetramethylchroman-2-ylmethoxy)benzyl]thiazolidine-2,4-dione. This substance was liquefied at 98°–100° C., solidified and again liquefied at 176°–178° C.

Nuclear Magnetic Resonance Spectrum (CDCl$_3$) $\delta$ ppm: 1.42 (3H, singlet); 1.98 (3H, singlet); about 2 (2H, multiplet); 2.03 (3H, singlet); 2.09 (3H, singlet); 2.31 (3H, singlet); 2.63 (2H, broad triplet, J=6 Hz); 3.03 (1H, doublet of doublets, J=15 & 9 Hz); 3.42 (1H, doublet of doublets, J=15 & 4.5 Hz); 3.84 and 3.98 (2H, AB Type, J=9 Hz); 4.45 (1H, doublet of doublets, J=9 & 4.5 Hz); 6.87 (2H, doublet, J=9 Hz); 7.15 (2H, doublet, J=9 Hz); 7.38 (6H, singlet); 8–8.5 (1H, broad singlet).

Elemental Analysis: Calculated for $C_{26}H_{29}NO_6S \cdot C_6H_6$: C, 68.45%, H, 6.28%, N, 2.50%, S, 5.70%. Found: C, 68.54%, H, 6.13%, N, 2.51%, S, 5.87%.

(b)
5-[4-(6-Acetoxy-2,5,7,8-tetramethylchroman-2-ylmethoxy)benzyl]thiazolidine-2,4-dione In order that the desired free 5-[4-(6-acetoxy-2,5,7,8-tetramethylchroman-2-ylmethoxy)benzyl]thiazolidine-2,4-dione could be obtained, 730 mg of the benzene mono adduct obtained as described in step (a) above were dissolved in 5 ml of acetone; the solvent was distilled off; the residue was solidified by adding water; and the white amorphous powder produced was vacuum-dried in a dessicator in the presence of phosphorus pentoxide, to give 0.61 g of the title compound, softening at about 90° C.

Elemental Analysis: Calculated for $C_{26}H_{29}NO_6S$: C, 64.60%, H, 6.06%, N, 2.90%, S, 6.62%. Found: C, 64.34%, H, 6.15%, N, 2.84%, S, 6.55%.

Nuclear Magnetic Resonance Spectrum (hexadeuterated acetone) $\delta$ ppm: 1.41 (3H, singlet); 1.97 (3H, singlet); 1.98 (3H, singlet); about 2 (2H, nd); 2.04 (3H, singlet); 2.27 (3H, singlet); 2.67 (2H, broad triplet, J=6 Hz); 3.07 (1H, doublet of doublets, J=15 & 9 Hz); 3.42 (1H, doublet of doublets, J=15 & 4.5 Hz); 4.00 (2H, AB Type, J=9 Hz); 4.71 (1H, doublet of doublets, J=9 & 4.5 Hz); 6.91 (2H, doublet, J=9 Hz); 7.21 (2H, doublet, J=9 Hz).

EXAMPLE 4

5-[4-(6-Acetoxy-5,7,8-trimethylchroman-2-ylmethoxy)benzyl]-2-iminothiazolidin-4-one The procedure described in Example 1(a) was repeated, except that 490 mg of ethyl 3-[4-(6-acetoxy-5,7,8-trimethylchroman-2-ylmethoxy)phenyl]-2-chloropropionate, 100 mg of thiourea and 2 ml of sulfolane were heated at 110°–120° C. for 5 hours. The product was then treated as described in Example 1(a), except that the crude product (in the form of crystals) was washed with ethyl acetate, to give the title compound, softening at 228°–236° C.

Mass spectrum (m/e): 468 (M+).

Nuclear Magnetic Resonance Spectrum (hexadeuterated dimethyl sulfoxide+CDCl$_3$) $\delta$ ppm: 1.92 (3H, singlet); 1.93 (3H, singlet); 2.02 (3H, singlet); 1.63–2.17 (2H, nd); 2.30 (3H, singlet); 2.57–3.97 (4H, nd); 4.0–4.37 (3H, nd); 4.53 (1H, doublet of doublets, J=9 & 4 Hz); 6.93 (2H, doublet, J=9 Hz); 7.19 (2H, doublet, J=9 Hz); 8.5–9.0 (2H, broad singlet, D).

EXAMPLE 5

(a)
5-[4-(6-Acetoxy-2,7-dimethylchroman-2-ylmethoxy)benzyl]thiazolidine-2,4-dione The reactions described in Example 1(a) were repeated, except that 1.5 g of ethyl 3-[4-(6-acetoxy-2,7-dimethylchroman-2-ylmethoxy)phenyl]-2-chloropropionate, 300 mg of thiourea and 2 ml of sulfolane were heated at 120° C. for 2 hours. The reaction mixture was then purified by adding diethyl ether to the reaction mixture, and distilling off the solvent to leave a residue. This residue was purified by column chromatography through silica gel eluted first with a 9:1 by volume mixture of benzene and ethyl acetate, to give the title compound.

Mass spectrum (m/e): 455 (M+).

Rf value: 0.41 (thin layer chromatography, silica gel, developing solvent: 4:1 by volume mixture of benzene and ethyl acetate).

Nuclear Magnetic Resonance Spectrum (CDCl$_3$) δ ppm: 1.42 (3H, singlet); 1.65–2.4 (2H, multiplet); 2.10 (3H, singlet); 2.28 (3H, singlet); 2.73 (2H, broad triplet, J=6 Hz); 3.0–3.6 (2H, multiplet); 3.93 (2H, AB Type, J=9 Hz); 4.50 (1H, doublet of doublets, J=9 & 4.5 Hz); 6.70 (1H, singlet); 6.73 (1H, singlet); 6.85 (2H, doublet, J=9 Hz); 7.15 (2H, doublet, J=9 Hz); 8.7–9.0 (1H, broad singlet, D).

(b)
5-[4-(6-Acetoxy-2,7-dimethylchroman-2-ylmethoxy)-benzyl]-2-iminothiazolidin-4-one The silica gel chromatography column described in Example 5(a) was then eluted with a 1:4 by volume mixture of benzene and tetrahydrofuran, to give the title compound as a solid softening at 170°–175° C.

Rf value: 0.57 (thin layer chromatography, silica gel, developing solvent: 1:4 by volume mixture of benzene and tetrahyrofuran).

Mass spectrum (m/e): 454 (M+).

Nuclear Magnetic Resonance Spectrum (heptadeuterated dimethylformamide) δ ppm: 1.39 (3H, singlet); 1.7–2.2 (2H, multiplet); 2.03 (3H, singlet); 2.27 (3H, singlet); 2.6–3.0 (3H, nd); 3.0–4.0 (1H, broad singlet, D); 3.42 (1H, doublet of doublets, J=15 & 4.5 Hz); 4.02 (2H, singlet); 4.53 (1H, doublet of doublets, J=9 & 4.5 Hz); 6.65 (1H, singlet); 6.79 (1H, singlet); 6.95 (2H, doublet, J=9 Hz); 7.21 (2H, doublet, J=9 Hz); 8.4–9.0 (1H, broad singlet, D).

EXAMPLE 6

5-{4-[2-(6-Acetoxy-7-t-butyl-2-methylchroman-2-yl)ethoxy]benzyl}-2-iminothiazolidin-4-one The procedure described in Example 1(a) was repeated, except that 266 mg of ethyl 3-{4-[2-(6-acetoxy-7-t-butyl-2-methylchroman-2-yl)ethoxy]phenyl}-2-chloropropionate, 50 mg of thiourea and 4 ml of sulfolane were heated at 110°–120° C. for 4.5 hours. The product was treated as described in Example 1(a) except that the crude product was purified by column chromatography through silica gel eluted with a 1:1 by volume mixture of benzene and ethyl acetate, to give the title compound, melting at 175°–178° C.

Mass spectrum (m/e): 510 (M+).

Nuclear Magnetic Resonance Spectrum (hexadeuterated dimethyl sulfoxide) δ ppm: 1.24 (9H, singlet); 1.31 (3H, singlet); 1.82 (2H, broad triplet, J=7 Hz); 2.03 (2H, broad triplet, J=7 Hz); 2.25 (3H, singlet); 2.68 (2H, triplet, J=7 Hz); 2.87 (1H, doublet of doublets, J=14 & 9 Hz); 3.30 (1H, doublet of doublets, J=14 & 4 Hz); 4.13 (2H, triplet, J=7 Hz); 4.51 (1H, doublet of doublets, J=9 & 4 Hz); 6.68 (1H, singlet); 6.75 (1H, singlet); 6.87 (2H, doublet, J=9 Hz); 7.15 (2H, doublet, J=9 Hz); 8.67 (1H, broad singlet, D); 8.88 (1H, broad singlet, D).

EXAMPLE 7

5-{4-[2-(6-Acetoxy-7,8-dimethoxy-2,5-dimethylchroman-2-yl)ethoxy]benzyl}-2-iminothiazolidin-4-one The procedure described in Example 1(a) was repeated, except that 558 mg of ethyl 3-{4-[2-(6-acetoxy-7,8-dimethoxy-2,5-dimethylchroman-2-yl)ethoxy]-phenyl}-2-chloropropionate, 100 mg of thiourea and 12 ml of sulfolane were heated at 110°–115° C. for 3.5 hours. The product was subsequently treated as described in Example 1(a), except that the crude product, in the form of an oil, was purified by column chromatography through silica gel, eluted with a 20:1 by volume mixture of ethyl acetate and methanol, to give the title compound, softening at 103°–110° C.

Mass spectrum (m/e): 528 (M+).

Nuclear Magnetic Resonance Spectrum (hexadeuterated acetone) δ ppm: 1.39 (3H, singlet); 1.94 (3H, singlet); 1.8–2.15 (4H, nd); 2.23 (3H, singlet); 2.63 (2H, broad triplet, J=6 Hz); 2.83 (1H, doublet of doublets, J=15 & 9 Hz); 3.42 (1H, doublet of doublets, J=15 & 5 Hz); 3.77 (3H, singlet); 3.78 (3H, singlet); 4.21 (2H, broad triplet, J=6 Hz); 4.45 (1H, doublet of doublets, J=9 & 5 Hz); 6.87 (2H, doublet, J=9 Hz); 7.19 (2H, doublet, J=9 Hz); 7.7–8.2 (1H, broad singlet, D).

EXAMPLE 8

5-{4-[2-(6-Hydroxy-2,5,7,8-tetramethylchroman-2-yl)ethoxy]benzyl}thiazolidine-2,4-dione 1.6 g of ethyl 3-{4-[2-(6-acetoxy-2,5,7,8-tetramethylchroman-2-yl)ethoxy]phenyl}-2-chloropropionate, 300 mg of thiourea and 2 ml of sulfolane were heated at 110°–115° C. for 3 hours under a nitrogen stream. A mixture of 4 ml of water, 2 ml of ethylene glycol monomethyl ether and 1 ml of concentrated hydrochloric acid was then added and the whole mixture was heated at 95°–97° C. for 4.5 hours. The mixture was then treated as described in Example 1(a), except that the crude product, in the form of an oil, was purified by column chromatography through silica gel, eluted with a 10:1 by volume mixture of benzene and ethyl acetate, to give the title compound, melting at 152°–154° C.

Mass spectrum (m/e): 455 (M+).

Nuclear Magnetic Resonance Spectrum (hexadeuterated acetone) δ ppm: 1.34 (3H, singlet); 1.87 (2H, broad triplet, J=7 Hz); 2.03 (3H, singlet); 2.07 (3H, singlet); 2.14 (3H, singlet); 2.0 (2H, nd); 2.64 (2H, broad triplet, J=7 Hz); 3.07 (1H, doublet of doublets, J=15 & 9 Hz); 3.41 (1H, doublet of doublets, J=15 & 4.5 Hz); 4.0–4.4 (3H, multiplet); 4.70 (1H, doublet of doublets, J=9 & 4.5 Hz); 6.95 (2H, doublet, J=9 Hz); 7.20 (2H, doublet, J=9 Hz).

EXAMPLE 9

(a)
5-{4-[2-(6-Hydroxy-2,5,7,8-tetramethylchroman-2-yl)ethoxy]benzyl}thiazolidine-2,4-dione The procedure described in Example 1(a) was repeated, except that 13.5 g of ethyl 2-chloro-3-{4-[2-(6-hydroxy-2,5,7,8-tetramethylchroman-2-yl)ethoxy]-phenyl}propionate, 4.4 g of thiourea and 20 ml of sulfolane were reacted for 14 hours at 110° C. The crude product was dissolved in ethyl acetate and the solution was washed with water and dried over anhydrous sodium sulfate. The solvent was then distilled off under reduced pressure and the resulting residue was purified by column chromatography through silica gel. This was first eluted with a 4:1 by volume mixture of benzene and ethyl acetate, and from these fractions were obtained the desired 5-{4-[2-(6-hydroxy-2,5,7,8-tetramethylchroman-2-yl)ethoxy]benzyl}thiazolidine-2,4-dione, whose melting point and nuclear magnetic resonance spectra agreed with those of the product of Example 8.

(b)
5-{4-[2-(6-Hydroxy-2,5,7,8-tetramethylchroman-2-yl)ethoxy]benzyl}-2-iminothiazolidin-4-one The column described in Example 9(a) above was then eluted with a 1:1 by volume mixture of benzene and tetrahydrofuran, and from the resulting fractions were obtained the desired 5-{4-[2-(6-hydroxy-2,5,7,8-tetramethylchroman-2-yl)ethoxy]benzyl}-2-iminothiazolidin-4-one, melting at 175°–180° C.

Mass spectrum (m/e): 454 (M+).

Nuclear Magnetic Resonance Spectrum (hexadeuterated dimethyl sulfoxide) δ ppm: 1.28 (3H, singlet); 1.6–2.2 (13H, nd); 2.2–3.2 (2H, nd); 2.80 (1H, doublet of doublets, J=15 & 9 Hz); 3.1–3.5 (1H, nd); 3.9–4.3 (2H, multiplet); 5.5 (1H, doublet of doublets, J=9 & 4.5 Hz); 6.82 (2H, doublet, J=9 Hz); 7.15 (2H, doublet, J=9 Hz); 7.37 (1H, singlet, D); 8.67 (1H, broad singlet, D); 8.89 (1H, broad singlet, D).

EXAMPLE 10

5-[4-(6-Hydroxy-5,7,8-trimethylchroman-2-ylmethoxy)benzyl]thiazolidine-2,4-dione 290 mg of 5-[4-(6-acetoxy-5,7,8-trimethylchroman-2-ylmethoxy)benzyl]-2-iminothiazolidin-4-one (prepared as described in Example 4) were added to a mixture of 3 ml of concentrated hydrochloric acid, 1.5 ml of water and 5 ml of ethylene glycol monomethyl ether, and the mixture was heated under reflux for 3.5 hours. The reaction mixture was then processed and purified as described in Example 1(a), and the crude product, in the form of an oil, was subjected to column chromatography through silica gel. The title compound, melting at 158°–159° C., was obtained from the fractions eluted with a 4:1 by volume mixture of benzene and ethyl acetate.

Mass spectrum (m/e): 427 (M+).

Nuclear Magnetic Resonance Spectrum (hexadeuterated dimethyl sulfoxide) δ ppm: 1.99 (3H, singlet); 2.04 (3H, singlet); 2.06 (3H, singlet); 1.5–2.25 (2H, nd); 2.25–2.87 (2H, nd); 2.87–3.5 (2H, nd); 3.97–4.34 (3H, nd); 4.87 (1H, doublet of doublets, J=9 & 4 Hz); 6.98 (2H, doublet, J=9 Hz); 7.20 (2H, doublet, J=9 Hz); 7.44 (1H, broad singlet, D); 11.3–12.3 (1H, broad singlet, D).

EXAMPLE 11

5-[4-(6-Hydroxy-2,7-dimethylchroman-2-ylmethoxy)benzyl]thiazolidine-2,4-dione 170 mg of 5-[4-(6-acetoxy-2,7-dimethylchroman-2-ylmethoxy)benzyl]-2-iminothiazolidin-4-one (prepared as described in Example 5) were added to a mixture of 0.2 ml of 2N hydrochloric acid and 2 ml of ethylene glycol monomethyl ether, and the mixture was reacted at 95°–97° C. for 6 hours. It was then processed and purified as described in Example 1(a), except that the crude product, in the form of an oil, was subjected to column chromatography through silica gel, eluted with a 9:1 by volume mixture of benzene and ethyl acetate, to give the title compound.

Rf value: 0.36 (thin layer chromatography, silica gel, developing solvent: 4:1 by volume mixture of benzene and ethyl acetate).

Mass spectrum (m/e): 413 (M+).

Nuclear Magnetic Resonance Spectrum (CDCl3) δ ppm: 1.42 (3H, singlet); 1.78 (1H, doublet of doublets, J=15 & 7 Hz); 2.07 (1H, doublet of doublets, J=15 & 7 Hz); 2.17 (3H, singlet); 2.68 (2H, broad triplet, J=7 Hz); 3.06 (1H, doublet of doublets, J=15 & 9 Hz); 3.46 (1H, doublet of doublets, J=15 & 4.5 Hz); 3.88 (2H, AB Type, J=9 Hz); 4.4–4.6 (2H, multiplet), changing after adding D2O to 4.47 (1H, doublet of doublets, J=9 & 4.5 Hz); 6.50 (1H, singlet); 6.62 (1H, singlet); 6.87 (2H, doublet, J=9 Hz); 7.15 (2H, doublet, J=9 Hz); 8.4–8.6 (1H, broad singlet, D).

EXAMPLE 12

5-{4-[2-(7-t-Butyl-6-hydroxy-2-methylchroman-2-yl)ethoxy]benzyl}thiazolidine-2,4-dione 75 mg of 5-{4-[2-(6-acetoxy-7-t-butyl-2-methylchroman-2-yl)ethoxy]benzyl}-2-iminothiazolidin-4-one (prepared as described in Example 6) were added to a mixture of 0.5 ml of concentrated hydrochloric acid, 2 ml of water and 2 ml of ethylene glycol monomethyl ether, and the mixture was heated under reflux for 4 hours. The mixture was then processed and purified by the procedures described in Example 1(a), except that the crude product, in the form of an oil, was purified by column chromatography through silica gel, eluted with a 5:1 by volume mixture of benzene and ethyl acetate, to give the title compound.

Rf value: 0.21 (thin layer chromatography, silica gel, developing solvent: 5:1 by volume mixture of benzene and ethyl acetate).

Mass spectrum (m/e): 469 (M+).

Nuclear Magnetic Resonance Spectrum (hexadeuterated dimethyl sulfoxide) δ ppm: 1.30 (9H, singlet); 1.32 (3H, singlet); 1.77 (2H, broad triplet, J=7 Hz); 1.99 (2H, broad triplet, J=7 Hz); 2.60 (2H, broad triplet, J=7 Hz); 3.03 (1H, doublet of doublets, J=15 & 9 Hz); 3.29 (1H, doublet of doublets, J=15 & 4.5 Hz); 4.11 (2H, broad triplet, J=7 Hz); 4.85 (1H, doublet of doublets, J=9 & 4.5 Hz); 6.48 (1H, singlet); 6.51 (1H, singlet); 6.89 (2H, doublet, J=9 Hz); 7.16 (2H, doublet, J=9 Hz); 8.63 (1H, broad singlet, D); 11.3–12.7 (1H, broad singlet, D).

EXAMPLE 13

5-{4-[2-(6-Hydroxy-7,8-dimethoxy-2,5-dimethylchroman-2-yl)ethoxy]-benzyl}thiazolidine-2,4-dione 560 mg of 5-{4-[2-(6-acetoxy-7,8-dimethoxy-2,5-dimethylchroman-2-yl)ethoxy]benzyl}-2-iminothiazolidin-4-one (prepared as described in Example 7) were added to a mixture of 7 ml of concentrated hydrochloric acid, 2.5 ml of water and 10 ml of ethylene glycol monomethyl ether, and the mixture was heated under reflux for 13 hours. The reaction mixture was then processed and purified as described in Example 1(a), except that the crude product, in the form of an oil, was purified by column chromatography through silica gel eluted with a 9:1 by volume mixture of chloroform and ethyl acetate, to give the title compound.

Rf value: 0.15 (thin layer chromatography, silica gel, developing solvent: 9:1 by volume mixture of chloroform and ethyl acetate).

Mass spectrum (m/e): 487 (M+).

Nuclear Magnetic Resonance Spectrum (CDCl3) δ ppm: 1.39 (3H, singlet); 1.90 (2H, broad triplet, J=6 Hz); 2.10 (3H, singlet); 2.15 (2H, broad triplet, J=6 Hz); 2.62 (2H, broad triplet, J=6 Hz); 3.09 (1H, doublet of doublets, J=15 & 9 Hz); 3.45 (1H, doublet of doublets, J=15 & 5 Hz); 3.85 (3H, singlet); 3.95 (3H, singlet); 4.20 (2H, broad triplet, J=6 Hz); 4.49 (1H, doublet of doublets, J=9 & 5 Hz); 5.40 (1H, singlet, D); 6.87 (2H, doublet, J=9 Hz); 7.16 (2H, doublet, J=9 Hz); 8.1-8.4 (1H, broad singlet, D).

EXAMPLE 14

5-{4-[2-(6-Hydroxy-2,5,7,8-tetramethylchroman-2-yl)ethoxy]benzyl}thiazolidine-2,4-dione The reaction described in Example 13 was repeated, except that 5-{4-[2-(6-hydroxy-2,5,7,8-tetramethylchroman-2-yl)ethoxy]benzyl}-2-iminothiazolidin-4-one (prepared as described in Example 9) was used as the starting material. This was subsequently treated as described in Example 1(a) and then separated and purified as in Example 8, to give the title compound, whose melting point and mass and nuclear magnetic resonance spectra agreed with those of the product of Example 8.

EXAMPLES 15-18

The procedure described in Example 3 was repeated, except that the acetic anhydride was replaced by the appropriate acylating agent identified hereafter and, in Example 18, a different thiazolidine derivative was used, to give the following compounds:

EXAMPLE 15

5-[4-(6-butyryloxy-2,5,7,8-tetramethylchroman-2-ylmethoxy)benzyl]thiazolidine-2,4-dione, using butyryl chloride Melting at: 147°-150° C.
Mass spectrum (m/e): 511 (M+).
Nuclear Magnetic Resonance Spectrum (CDCl$_3$) δ ppm: 1.06 (3H, triplet, J=6 Hz); 1.65-2.2 (13H, multiplet); 2.45-2.75 (4H, multiplet).

EXAMPLE 16

5-[4-(6-benzoyloxy-2,5,7,8-tetramethylchroman-2-ylmethoxy)benzyl]thiazolidine-2,4-dione, from benzoic anhydride.

Rf value: 0.53 (thin layer chromatography, silica gel, developing solvent: 4.1 by volume mixture of benzene and ethyl acetate).
Mass spectrum (m/e): 545 (M+).
Nuclear Magnetic Resonance Spectrum (hexadeuterated dimethyl sulfoxide) δ ppm: 7.45-7.85 (3H, multiplet); 8.05-8.3 (2H, multiplet).

EXAMPLE 17

5-[4-(2,5,7,8-tetramethyl-6-nicotinoyloxychroman-2-ylmethoxy)benzyl]thiazolidine-2,4-dione, from nicotinoyl chloride hydrochloride Melting at: 196°-198° C.
Mass spectrum (m/e): 546 (M+).
Nuclear Magnetic Resonance Spectrum (CDCl$_3$) δ ppm: 7.35-7.65 (1H, multiplet); 8.43-8.65 (1H, multiplet); 8.7-9.1 (1H, multiplet); 9.4-9.6 (1H, multiplet).

EXAMPLE 18

5-{4-[2-(2,5,7,8-tetramethyl-6-nicotinoyloxychroman-2-yl)ethoxy]benzyl}thiazolidine-2,4-dione, from nicotinoyl chloride hydrochloride and
5-{4-[2-(6-hydroxy-2,5,7,8-tetramethylchroman-2-yl)ethoxy]benzyl}thiazolidine-2,4-dione (prepared as described in Example 14)

Rf value: 0.45 (thin layer chromatography, silica gel, developing solvent: 1:1 by volume mixture of benzene and ethyl acetate).
Mass spectrum (m/e): 560 (M+).
Nuclear Magnetic Resonance Spectrum (heptadeuterated dimethylformamide) δ ppm: 7.6-7.85 (1H, multiplet); 8.5-8.7 (1H, multiplet); 8.9-9.1 (1H, multiplet); 9.35-9.5 (1H, multiplet).

In the nuclear magnetic resonance spectra reported in the above Examples 15-18, only those signals are reported which are characteristic of the 6-acyloxy part of the compound prepared.

EXAMPLE 19

5-[4-(2-Ethyl-6-hydroxy-5,7,8-trimethylchroman-2-ylmethoxy)benzyl]thiazolidine-2,4-dione 2.4 g of ethyl 3-[4-(6-acetoxy-2-ethyl-5,7,8-trimethylchroman-2-ylmethoxy)phenyl]-2-chloropropionate, 494 mg of thiourea and 3 ml of sulfolane were heated under a nitrogen stream for 4.5 hours at 100°-110° C. At the end of this time, 3 ml of ethylene glycol monomethyl ether, 3 ml of water and 1 ml of concentrated hydrochloric acid were added and the resulting mixture was heated for a further 3.5 hours at 96°-98° C. The reaction mixture was then processed as described in Example 1(a) and the resulting crude product, in the form of an oil, was purified by column chromatography, eluted with a 10:1 by volume mixture of benzene and ethyl acetate, to give the title compound.

Rf value: 0.29 (thin layer chromatography, silica gel, developing solvent: 4:1 by volume mixture of benzene and ethyl acetate).
Mass spectrum (m/e): 455 (M+).
Nuclear Magnetic Resonance Spectrum (hexadeuterated dimethyl sulfoxide) δ ppm: 0.90 (3H, triplet, J=6 Hz); 1.5-2.1 (4H, nd); 1.99 (3H, singlet); 2.01 (3H, singlet); 2.05 (3H, singlet); 2.4-2.7 (2H, multiplet); 2.8-3.7 (2H, nd); 3.94 (2H, singlet); 4.84 (1H, doublet of doublets, J=9 & 4.5 Hz); 6.90 (2H, doublet, J=9 Hz); 7.15 (2H, doublet, J=9 Hz); 7.40 (1H, broad singlet, D).

EXAMPLE 20

5-[4-(6-Hydroxy-2-isobutyl-5,7,8-trimethylchroman-2-ylmethoxy)benzyl]thiazolidine-2,4-dione 1.99 g of ethyl 3-[4-(6-acetoxy-2-isobutyl-5,7,8-trimethylchroman-2-ylmethoxy)phenyl]-2-chloropropionate, 0.42 g of thiourea and 2.1 g of sulfolane were reacted under a nitrogen stream at 125°-150° C. for 3.5 hours. At the end of this time, 15 ml of ethylene glycol monomethyl ether, 4 ml of water and 2 ml of concentrated hydrochloric acid were added and the mixture was reacted for a further 3.5 hours at 96°-98° C. The reaction mixture was then treated as described in Example 1(a) and the resulting crude product, in the form of an oil, was purified by column chromatography through silica gel, eluted with a 5:1 by volume mixture of hexane and ethyl acetate, to give the title compound.

Rf value: 0.30 (thin layer chromatography, silica gel, developing solvent: 4:1 by volume mixture of benzene and ethyl acetate).
Mass spectrum (m/e): 483 (M+).
Nuclear Magnetic Resonance Spectrum (CDCl$_3$) δ ppm: 0.96 (3H, doublet, J=6 Hz); 1.01 (3H, doublet, J=6 Hz); 1.71 (2H, doublet, J=6 Hz); 1.8-2.3 (3H, nd); 2.10 (6H, singlet); 2.16 (3H, singlet); 2.61 (2H, triplet, J=6 Hz); 3.02 (1H, doublet of doublets, J=9 & 15 Hz); 3.43 (1H, doublet of doublets, J=4 & 15 Hz); 3.92 (2H, singlet); 4.33 (1H, singlet); 4.43 (1H, doublet of doublets, J=4 & 9 Hz); 6.85 (2H, doublet, J=9 Hz); 7.13 (2H, doublet, J=9 Hz); 8.4-9.0 (1H, broad).

EXAMPLE 21

Monosodium salt of
5-[4-(6-hydroxy-2,5,7,8-tetramethylchroman-2-ylmethoxy)benzyl]thiazolidine-2,4-dione 101 mg of 5-[4-(6-hydroxy-2,5,7,8-tetramethylchroman-2-ylmethoxy)benzyl]thiazolidine-2,4-dione were suspended in 0.5 ml of 99.5% ethanol. 4.33 ml of a 0.0526N ethanolic solution of sodium hydroxide were then added to the suspension and the mixture was stirred at room temperature for 1 hour. The crystals obtained by evaporating off the solvent under reduced pressure were dried by heating them under reduced pressure at 60° C. for 3 hours in the presence of phosphorus pentoxide, to give the title compound, melting at 203°–208° C. (with decomposition).

Nuclear Magnetic Resonance Spectrum (hexadeuterated dimethyl sulfoxide) δ ppm: 1.30 (3H, singlet); 1.66–2.10 (2H, multiplet); 1.96 (3H, singlet); 2.03 (3H, singlet); 2.05 (3H, singlet); 2.35–2.80 (3H, multiplet); 3.15–3.35 (1H, multiplet); 3.92 (2H, broad singlet); 4.09 (1H, doublet of doublets, J=4.5 & 11.5 Hz); 6.85 (2H, doublet, J=9 Hz); 7.10 (2H, doublet, J=9 Hz); 7.42 (1H, broad singlet, D).

Elemental analysis: Calculated for $C_{24}H_{26}NO_5SNa \cdot H_2O$: C, 59.86%; H, 5.86%; N, 2.91%; S, 6.66%; Na, 4.77%. Found: C, 59.78%; H, 5.54%; N, 2.84%; S, 6.37%; Na, 5.04%.

EXAMPLE 22

5-[4-(6-Hydroxy-2,5,7,8-tetramethyl-4-oxochroman-2-ylmethoxy)benzyl]thiazolidine-2,4-dione A mixture of 1.3 g of ethyl 3-[4-(6-acetoxy-2,5,7,8-tetramethyl-4-oxochroman-2-ylmethoxy)phenyl]-2-chloropropionate (prepared as described in Preparation 45), 0.4 g of thiourea and 2 g of sulfolane was heated at 120°–130° C. for 4 hours under a nitrogen stream. Then 15 ml of ethylene glycol monomethyl ether, 4 ml of water and 2 ml of concentrated hydrochloric acid were added, in that order, to the reaction mixture, and heating was continued, but at 70°–90° C., for a further 2.5 days. Water was then added to the reaction mixture, after which it was extracted with benzene. The extract was washed with water and dried over anhydrous sodium sulfate. Benzene was distilled off from the extract. The residue was subjected to silica gel column chromatography, eluted with a 5:3 by volume mixture of hexane and ethyl acetate, to yield 5-[4-(6-hydroxy-2,5,7,8-tetramethyl-4-oxochroman-2-ylmethoxy)benzyl]-thiazolidine-2,4-dione. Its softening point was 79°–83° C.

Nuclear Magnetic Resonance Spectrum (CDCl$_3$) δ ppm: 1.50 (3H, singlet); 2.11 (3H, singlet); 2.22 (3H, singlet); 2.56 (3H, singlet); 2.66 (1H, doublet, J=15 Hz); 3.05 (1H, doublet, J=15 Hz); 3.05 (1H, doublet of doublets, J=9 & 15 Hz); 3.42 (1H, doublet of doublets, J=4 & 15 Hz); 3.95 (1H, doublet, J=10 Hz); 4.07 (1H, doublet, J=10 Hz); 4.46 (1H, doublet of doublets, J=4 & 9 Hz); 4.5–5.2 (1H, broad singlet); 6.84 (2H, doublet, J=9 Hz); 7.13 (2H, doublet, J=9 Hz).

EXAMPLE 23

5-[4-(4,6-Dihydroxy-2,5,7,8-tetramethylchroman-2-ylmethoxy)benzyl]thiazolidine-2,4-dione 450 mg of sodium borohydride were added to a mixture of 278 mg of 5-[4-(6-hydroxy-2,5,7,8-tetramethyl-4-oxochroman-2-ylmethoxy)benzyl]thiazolidine-2,4-dione (prepared as described in Example 22) and 9 ml of methanol, and the resulting mixture was stirred at room temperature for 2 hours. Then, a 1% w/v aqueous solution of acetic acid was added to the reaction mixture, and the mixture was neutralized with an aqueous solution of potassium carbonate and extracted with ethyl acetate. The ethyl acetate solution was washed with water and dried over anhydrous sodium sulfate. Ethyl acetate was distilled off from the mixture under reduced pressure, and the resulting residue was subjected to silica gel column chromatography, eluted with a 5:3 by volume mixture of hexane and ethyl acetate, to yield 5-[4-(4,6-dihydroxy-2,5,7,8-tetramethylchroman-2-ylmethoxy)benzyl]thiazolidine-2,4-dione. Its melting point was 102°–118° C.

Nuclear Magnetic Resonance Spectrum (hexadeuterated acetone and D$_2$O) δ ppm: 1.52 (3H, singlet); 2.01 (3H, singlet); 2.13 (3H, singlet); 2.29 (3H, singlet); 1.9–2.5 (1H, nd); 2.9–3.6 (2H, multiplet); 4.03 (2H, singlet); 3.9–4.5 (1H, nd); 4.6–5.1 (2H, multiplet); 6.7–7.4 (4H, nd).

EXAMPLE 24

5-[4-(7-t-Butyl-6-hydroxy-2-methyl-4-oxochroman-2-ylmethoxy)benzyl]thiazolidine-2,4-dione In a similar manner to Example 22, a mixture of 291 mg of ethyl 3-[4-(6-acetoxy-7-t-butyl-2-methyl-4-oxochroman-2-ylmethoxy)phenyl]-2-chloropropionate (prepared as described in Preparation 49), 64 mg of thiourea and 1 ml of sulfolane was heated. 5 ml of ethylene glycol monomethyl ether, 1 ml of concentrated hydrochloric acid and 2 ml of water were added, and the resulting mixture was further heated under reflux for 6 hours. Ethyl acetate was then added to the reaction mixture, and the resulting solution was washed with water and dried over anhydrous sodium sulfate. The ethyl acetate was removed by evaporation under reduced pressure, and the resulting residue was subjected to silica gel column chromatography, eluted with a 5:1 by volume mixture of benzene and ethyl acetate, to give 143 mg of the desired 5-[4-(7-t-butyl-6-hydroxy-2-methyl-4-oxochroman-2-ylmethoxy)benzyl]thiazolidine-2,4-dione.

Softening point: 95°–107° C.

Nuclear Magnetic Resonance Spectrum (hexadeuterated acetone) δ ppm: 1.40 (9H, singlet); 1.48 (3H, singlet); 2.65 (1H, doublet, J=16.5 Hz); 3.05 (1H, doublet, J=16.5 Hz); 3.08 (1H, doublet of doublets, J=9 & 14 Hz); 3.42 (1H, doublet or doublets, J=4.5 & 14 Hz); 4.14 (2H, singlet); 4.74 (1H, doublet of doublets, J=4.5 & 9 Hz); 6.83 (1H, singlet); 6.92 (2H, doublet, J=9 Hz); 7.23 (1H, singlet); 7.24 (2H, doublet, J=9 Hz); 7.50–9.40 (1H, broad, D).

EXAMPLE 25

5-[4-(6-Acetoxy-2,5,7,8-tetramethyl-4-oxochroman-2-ylmethoxy)benzyl]-2-iminothiazolidin-4-one A mixture of 2.0 g of ethyl 3-[4-(6-acetoxy-2,5,7,8-tetramethyl-4-oxochroman-2-ylmethoxy)phenyl]-2-chloropropionate (prepared as described in Preparation 45), 0.62 g of thiourea, and 3.1 g of sulfolane was heated at 120°–125° C. for 7 hours under a nitrogen stream. The reaction mixture was extracted with benzene and then the benzene was distilled off from the extract. Water was then added to the residue and the oily layer was separated. The oily layer was subjected to silica gel column chromatography [successively with an eluent of (1) a 2:1 by volume mixture of n-hexane and ethyl acetate, (2) ethyl acetate, and (3) a 1:1 by volume mixture of ethyl acetate and ethanol] to yield 5-[4-(6-acetoxy-2,5,7,8-tetramethyl-4-oxochroman-2-ylmethoxy)benzyl]-2-iminothiazolidin-4-one in a yield of 0.74 g. This was further purified by recrystallization from ethyl acetate, to give the purified title compound melting at was 218°–222° C.

Nuclear Magnetic Resonance Spectrum (hexadeuterated dimethyl sulfoxide+$D_2O$) δ ppm: 1.43 (3H, singlet); 2.04 (6H, singlet); 2.32 (3H, singlet); 2.35 (3H, singlet); 2.4–3.5 (4H, nd); 4.13 (2H, singlet); 4.56 (1H, doublet of doublets, J=4 & 9 Hz); 6.85 (2H, doublet, J=9 Hz); 7.14 (2H, doublet, J=9 Hz).

TEST EXAMPLE 1

Effect on hyperlipidaemia

The test animals were 8 weeks old male mice. These animals were fasted for 18 hours, after which 75 mg/kg of alloxan was injected into the tail vein of each animal. Each of the test compounds was administered orally at a dose of 100 mg/kg body weight 30 minutes before and 24 and 30 hours after administration of the alloxan. Blood was collected from an incision in the cervical region 48 hours after administration of the alloxan. The amount collected was 100 or 200 μl. The blood was diluted 10 or 20 times with a physiological saline solution and centrifuged (3,000 rpm, 10 minutes) to determine the lipid content.

Lipid peroxide was determined at TBA (thiobarbituric acid)—reacting substance according to Yagi's method [K. Yagi: Biochem. Med., 15, 212–216 (1976)]. Measurements of cholesterol and triglyceride were made according to the enzyme method. A Determiner TC (a registered trade mark of Kyowa Medix) kit was used for the measurement of cholesterol and Triglyceride Measuring Agent (GPO-p-chlorophenol color developing method) (Wako Jyunyaku) kit was used for triglyceride.

As a control, the procedure was repeated, except that no test compound was administered.

The test compounds were as follows:

Compound A:

5-[4-(6-hydroxy-2,5,7,8-tetramethylchroman-2-ylmethoxy)benzyl]thiazolidine-2,4-dione (a compound of the invention);

Compound B:

5-[4-(1-methylcyclohexylmethoxy)benzyl]thiazolidine-2,4-dione (a prior art compound).

The results are shown in the following Table:

TABLE 1

| agent | No. of animals | lipid peroxide (nmol/ml) | triglyceride (mg/dl) | cholesterol (mg/dl) |
| --- | --- | --- | --- | --- |
| Control | 10 | 36.8 ± 6.9 | 636 ± 128 | 81.3 ± 4.7 |
| Compound A | 10 | 16.8 ± 1.5 ($P < 0.02$) | 270 ± 33 ($P < 0.02$) | 59.6 ± 1.4 ($P < 0.01$) |
| Compound B | 10 | 29.9 ± 5.2 (NS) | 586 ± 127 (NS) | 72.5 ± 5.6 (NS) |

NS = not significant.

As shown in Table 1, Compound A of this invention significantly inhibited lipid peroxide, triglyceride and cholesterol, but the comparative compound did not exhibit such an inhibitory action.

TEST EXAMPLE 2

Effect On Blood Sugar

The test animals employed were male mice of the $C_{57}BL/6J$-Ob/Ob strain aged about 4 months. The animals were employed in groups of 4 for each test.

Compound A and the same prior art Compound B as was used in Test Example 1 were mixed at a level of 0.2% by weight with a powder feed (MM-1, Funabashi Farm) and given freely to the mice for 2 weeks, during which time water was also freely available. At the end of the experiment, blood was collected from a vein in the tail and the blood sugar level was determined by the glucose oxidase method. A control group was treated similarly, except that the active compounds were omitted.

With the blood sugar level of the control set arbitrarily at 100, the blood sugar level of Compound A was 57 and that of Compound B was 56, indicating an excellent ability to reduce blood sugar levels.

PREPARATION 1

6-(Methoxymethoxy)-2,5,7,8-tetramethylchroman-2-ylmethanol 16.1 g of 6-hydroxy-2,5,7,8-tetramethylchroman-2-ylmethanol were dissolved in 70 ml of dry dimethylformamide. 3.0 g of a 50% w/w suspension of sodium hydride in oil (which had been washed with cyclohexane 3 times) were added gradually to the resulting solution at 5°–10° C., with stirring and under a nitrogen stream. The mixture was reacted for 1 hour at room temperature, and then the solution was ice-cooled to 3°–5° C., and 5.5 g of chloromethyl methyl ether dissolved in 40 ml of dry benzene were added dropwise. After the whole of this had been added, the solution was reacted for 1 hour at room temperature. The reaction mixture was then poured into ice-water and extracted with cyclohexane. The extract was washed four times with a 5% w/v aqueous solution of sodium hydroxide, and then with water. It was then dried and the solvent was distilled off under reduced pressure, giving the desired 6-(methoxymethoxy)-2,5,7,8-tetramethylchroman-2-ylmethanol. On thin layer chromatography, the Rf value was 0.45 [silica gel; developing solvent:benzene:ethyl acetate=4:1 by volume].

Nuclear Magnetic Resonance Spectrum ($CDCl_3$) δ ppm: 1.21 (3H, singlet); 1.6–2.0 (3H, multiplet); 2.07 (3H, singlet); 2.15 (3H, singlet); 2.19 (3H, singlet); 2.6 (2H, broad triplet, J=9 Hz); 3.60 (3H, singlet); 3.63 (2H, singlet); 4.85 (2H, singlet).

PREPARATION 2

6-(Methoxymethoxy)-2,5,7,8-tetramethyl-2-(4-nitrophenoxymethyl)chroman 6 g of a 50% w/w suspension of sodium hydride in oil were placed in a reaction container and washed with cyclohexane. 100 ml of dry dimethyl sulfoxide and then 19.0 g of 6-(methoxymethoxy)-2,5,7,8-tetramethylchroman-2-ylmethanol dissolved in 20 ml of dry benzene were added, and the mixture was reacted for 20 minutes under a nitrogen stream at 60° C. Small portions of p-chloronitrobenzene (totalling 21.6 g) were added to this solution whilst cooling with water to 30° C., and then the reaction was continued for 1 hour at 60° C. The reaction mixture was then poured into ice-water and extracted with ethyl acetate. The extract was washed with water, and dried over anhydrous sodium sulfate. The solvent was distilled off, leaving a reddish brown crude oil. This oil was subjected to silica gel column chromatography, eluted first with a 1:1 by volume mixture of benzene and cyclohexane and then with benzene alone. A light yellowish oil, the desired 6-(methoxymethoxy)-2,5,7,8-tetramethyl-2-(4-nitrophenoxymethyl)-chroman, was obtained from the portion eluted with benzene. Rf value on thin layer chromatography: 0.12 [silica gel; developing solvent:benzene].

Nuclear Magnetic Resonance Spectrum (CDCl$_3$) δ ppm: 1.41 (3H, singlet); about 2 (2H, multiplet); 2.05 (3H, singlet); 2.14 (3H, singlet); 2.18 (3H, singlet); 2.6 (2H, broad triplet, J=9 Hz); 3.60 (3H, singlet); 3.95 and 4.09 (2H, AB type, J=9 Hz); 4.86 (2H, singlet); 6.96 (2H, doublet, J=9 Hz); 8.19 (2H, doublet, J=9 Hz).

PREPARATION 3

6-Hydroxy-2,5,7,8-tetramethyl-2-(4-nitrophenoxymethyl)chroman 32.8 g of 6-(methoxymethoxy)-2,5,7,8-tetramethyl-2-(4-nitrophenoxymethyl)chroman were dissolved in 300 ml of acetic acid containing 5.3 g of a 10% w/w aqueous solution of sulfuric acid, and the mixture was heated for 10 minutes at 60° C. The reaction mixture was cooled and then poured into a mixture of 420 g of sodium bicarbonate and 1 kg of ice and extracted with ethyl acetate. The extract was washed with water and dried over anhydrous sodium sulfate. The solvent was distilled off from the extract, leaving a light yellowish powder, the desired 6-hydroxy-2,5,7,8-tetramethyl-2-(4-nitrophenoxymethyl)chroman, melting at 114°–116° C.

Nuclear Magnetic Resonance Spectrum (CDCl$_3$) δ ppm: 1.41 (3H, singlet); about 2 (2H, multiplet); 2.06 (3H, singlet); 2.10 (3H, singlet); 2.15 (3H, singlet); 2.6 (2H, broad triplet, J=6 Hz); 4.05 (2H, AB Type, J=9 Hz); 4.25 (1H, broad singlet); 6.96 (2H, doublet, J=9 Hz); 8.16 (2H, doublet, J=9 Hz).

PREPARATION 4

6-Acetoxy-2,5,7,8-tetramethyl-2-(4-nitrophenoxymethyl)chroman 20.4 g of 6-hydroxy-2,5,7,8-tetramethyl-2-(4-nitrophenoxymethyl)chroman were dissolved in 60 ml of pyridine, and, while stirring, 30 ml of acetic anhydride were added dropwise at 10° C. The mixture was gradually restored to room temperature and then reacted for 1 hour at 30° C. The reaction mixture was cooled and then poured into ice-water and extracted with a 1:1 by volume mixture of benzene and cyclohexane. The extract was washed well with a 2% w/v aqueous solution of hydrochloric acid and then with water, after which it was dried over anhydrous sodium sulfate. The solvent was removed by evaporation under reduced pressure, giving the desired 6-acetoxy-2,5,7,8-tetramethyl-2-(4-nitrophenoxymethyl)chroman. Rf value on thin layer chromatography: 0.64 [silica gel; developing solvent; benzene and ethyl acetate=10:1 by volume]

Nuclear Magnetic Resonance Spectrum (CDCl$_3$) δ ppm: 1.41 (3H, singlet); 1.98 (3H, singlet); about 2 (2H, multiplet); 2.02 (3H, singlet); 2.05 (3H, singlet); 2.31 (3H, singlet); 2.6 (2H, broad triplet, J=6 Hz); 3.98 and 4.10 (2H, AB Type, J=9 Hz); 6.97 (2H, doublet, J=9 Hz); 8.20 (2H, doublet, J=9 Hz).

PREPARATION 5

6-Acetoxy-2-(4-aminophenoxymethyl)-2,5,7,8-tetramethylchroman 24.3 g of 6-acetoxy-2,5,7,8-tetramethyl-2-(4-nitrophenoxymethyl)chroman were dissolved in a mixture of 200 ml of methanol and 20 ml of benzene and reacted for 3 hours under a hydrogen pressure of 45–55 lb/sq. inch (3.1–3.8 bars), using Pearl's hydrogen adding apparatus, in the presence of 7 g of 10% w/w palladium-on-carbon. The palladium-on-carbon was removed by filtration from the reaction mixture and washed with a mixture of 600 ml of acetone and 60 ml of concentrated hydrochloric acid. The filtrate and the washings were combined and the mixture was neutralized with sodium bicarbonate. The solvent was then distilled off, and the crude crystals obtained were dissolved in ethyl acetate. The ethyl acetate solution was washed with water and dried over anhydrous sodium sulfate. The ethyl acetate was then distilled from the extract, and the crude substance obtained was washed with a 1:1 by volume mixture of benzene and cyclohexane, giving the desired 6-acetoxy-2-(4-aminophenoxymethyl)-2,5,7,8-tetramethylchroman, melting at 138°–140° C.

Nuclear Magnetic Resonance Spectrum (CDCl$_3$) δ ppm: 1.42 (3H, singlet); about 2 (2H, multiplet); 2.00 (3H, singlet); 2.04 (3H, singlet); 2.10 (3H, singlet); 2.31 (3H, singlet); 2.6 (2H, broad triplet, J=6 Hz); 3.37 (2H, broad singlet); 3.80 and 3.95 (2H, AB Type, J=9 Hz); 6.62 (2H, doublet, J=9 Hz); 6.78 (2H, doublet, J=9 Hz).

PREPARATION 6

Ethyl 3-[4-(6-acetoxy-2,5,7,8-tetramethylchroman-2-ylmethoxy)phenyl]-2-chloropropionate 17.5 g of 6-acetoxy-2-(4-aminophenoxymethyl)-2,5,7,8-tetramethylchroman were dissolved in a mixture of 130 ml of acetone and 30 ml of water, and 13 ml of concentrated hydrochloric acid, followed by 4.3 g of sodium nitrite dissolved in 8.5 ml of water, were added dropwise, with ice-cooling, to the product. 37.3 ml of ethyl acrylate were added dropwise, and then 680 mg of cuprous oxide were added gradually to the product, whilst keeping its temperature at 40°–43° C. Generation of nitrogen terminated after about 30 minutes. Benzene was then added to the reaction mixture (which consisted of 2 layers) to extract the organic layer. The benzene extract was washed with a saturated aqueous solution of sodium chloride and dried over anhydrous sodium sulfate. The solvent was then distilled off from the extract. The dark brownish oil thus obtained was subjected to silica gel column chromatography, eluted with a 1:1 by volume mixture of benzene and cyclohexane and then the proportion of benzene was progressively increased until it was eluted with benzene alone. Ethyl 3-[4-(6-acetoxy-2,5,7,8-tetramethylchroman-2-ylmethoxy)phenyl]-2-chloropropionate was obtained from the fractions eluted with a 2:1 by volume mixture of benzene and cyclohexane and with benzene alone. Rf value on thin layer chromatography: 0.39 [silica gel; developing solvent:benzene:ethyl acetate=20:1 by volume].

Nuclear Magnetic Resonance Spectrum (CDCl$_3$) δ ppm: 1.23 (3H, triplet, J=7.5 Hz); 1.42 (3H, singlet); 1.98 (3H, singlet); about 2 (2H, multiplet); 2.04 (3H, singlet); 2.09 (3H, singlet); 2.31 (3H, singlet); 2.6 (2H, broad triplet, J=6 Hz); 3.05 (1H, doublet or doublets, J=15 & 7.5 Hz); 3.31 (1H, doublet or doublets, J=15 & 7.5 Hz); 3.83 and 3.99 (2H, AB Type, J=9 Hz); 4.18 (2H, quartet, J=7.5 Hz); 4.38 (1H, triplet, J=7.5 Hz); 6.85 (2H, doublet, J=9 Hz); 7.14 (2H, doublet, J=9 Hz).

PREPARATION 7

3-[4-(6-Acetoxy-2,5,7,8-tetramethylchroman-2-ylmethoxy)phenyl]-2-chloropropionic acid 0.16 g of ethyl 3-[4-(6-acetoxy-2,5,7,8-tetramethylchroman-2-ylmethoxy)phenyl]-2-chloropropionate was dissolved in a mixture of 1.5 ml of 99.5% ethanol and 0.2 ml of tetrahydrofuran. 265 mg of a 9.55% w/w aqueous solution of sodium hydroxide were added dropwise, under a nitrogen stream at 0°–4° C., to the resulting mixture. The mixture was then reacted for a further 20 hours at 0°–5° C., after which it was neutralized, whilst ice-cooling, by adding 0.68 g of a 10% w/w aqueous solution of hydrochloric acid. The solvent was then distilled off under reduced pressure. The separated light reddish oil was further extracted with chloroform, and the chloroform extract was washed with water and dried over anhydrous sodium sulfate. The crude product obtained by distilling off the chloroform under reduced pressure was subjected to column chromatography through silica gel and the desired 3-[4-(6-acetoxy-2,5,7,8-tetramethylchroman-2-ylmethoxy)phenyl]-2-chloropropionic acid was obtained from the fractions eluted with a 20:1 by volume mixture of benzene and 99.5% ethanol. Rf value on thin layer chromatography: 0.6 (tailing) [silica gel; developing solvent; benzene:99.5% ethanol=4:1 by volume].

Nuclear Magnetic Resonance Spectrum (CDCl$_3$) δ ppm: 1.42 (3H, singlet); 1.98 (3H, singlet); about 2 (2H, multiplet); 2.03 (3H, singlet); 2.09 (3H, singlet); 2.32 (3H, singlet); 2.6 (2H, broad triplet, J=6 Hz); 3.2 (2H, multiplet); 3.85 and 4.00 (2H, AB Type, J=9 Hz); 4.4 (1H, multiplet); 6.86 (2H, doublet, J=9 Hz); about 7 (1H, broad singlet); 7.15 (2H, doublet, J=9 Hz).

PREPARATION 8

2-Chloro-3-[4-(6-hydroxy-2,5,7,8-tetramethylchroman-2-ylmethoxy)phenyl]propionic acid 0.48 g of ethyl 3-[4-(6-acetoxy-2,5,7,8-tetramethylchroman-2-ylmethoxy)phenyl]-2-chloropropionate was dissolved in a mixture of 5 ml of 99.5% ethanol and 2 ml of tetrahydrofuran. To this was added dropwise, under a nitrogen stream at 8°–10° C., a solution prepared by dissolving 133 mg of sodium hydroxide in 1 ml of 99.5% ethanol. When the whole of the solution had been added, the mixture was reacted for a further 18 hours at 0°–5° C., after which it was neutralized by adding to it dropwise a solution prepared by dissolving 0.37 g of concentrated hydrochloric acid in 1 ml of 99.5% ethanol. The solvent was then distilled off from the mixture under reduced pressure. The pale reddish oil thus separated was extracted with chloroform, and the chloroform extract was washed with water and then dried over anhydrous sodium sulfate. The crude product obtained by distilling the chloroform off under reduced pressure was subjected to silica gel column chromatography, and the desired 2-chloro-3-[4-(6-hydroxy-2,5,7,8-tetramethylchroman-2-ylmethoxy)phenyl]propionic acid was obtained from the fractions eluted with a 10:1 by volume mixture of benzene and ethyl acetate. Rf value on thin layer chromatography: 0.4 (tailing) [silica gel; developing solvent; benzene:99.5% ethanol=6:1 by volume]. Melting point 148°–149° C.

Nuclear Magnetic Resonance Spectrum (CDCl$_3$) δppm: 1.40 (3H, singlet); about 2 (2H, multiplet); 2.10 (6H, singlet); 2.15 (3H, singlet); 2.6 (2H, broad triplet, J=6 Hz); 3.05 (1H, doublet of doublets, J=15 & 7.5 Hz); 3.30 (1H, doublet of doublets, J=15 & 7.5 Hz); 3.83 and 3.98 (2H, AB type, J=9 Hz); 4.40 (1H, triplet, J=7.5 Hz); about 6 (2H, broad singlet); 6.85 (2H, doublet, J=9 Hz); 7.14 (2H, doublet, J=9 Hz).

PREPARATION 9

Ethyl 2-chloro-3-[4-(6-hydroxy-2,5,7,8-tetramethylchroman-2-ylmethoxy)phenyl]propionate 0.48 g of ethyl 3-[4-(6-acetoxy-2,5,7,8-tetramethylchroman-2-ylmethoxy)phenyl]-2-chloropropionate was dissolved in a mixture of 3 ml of absolute ethanol and 2 ml of dry tetrahydrofuran. An ethanolic solution of sodium ethoxide (prepared by dissolving 49.0 mg sodium in 2 ml of absolute ethanol) was added dropwise, under a nitrogen stream at 10°–13° C., to the resulting solution. The mixture was then reacted for 21 hours at 0°–5° C., after which 0.22 g of concentrated hydrochloric acid dissolved in 99.5% ethanol was added dropwise, with ice-cooling. The solvent was then distilled off from the reaction mixture under reduced pressure; the separated light reddish oil was extracted with chloroform; and the extract was washed with water and then dried over anhydrous sodium sulfate. The crude product obtained by distilling the chloroform off from the extract under reduced pressure was subjected to silica gel column chromatography, and the desired ethyl 2-chloro-3-[4-(6-hydroxy-2,5,7,8-tetramethylchroman-2-ylmethoxy)phenyl]propionate was obtained from the fractions eluted with benzene. Rf value on thin layer chromatography: 0.60 [silica gel; developing solvent; benzene:ethyl acetate=10:1 by volume].

Nuclear Magnetic Resonance Spectrum (CDCl$_3$) δ ppm: 1.23 (3H, triplet, J=7.5 Hz); 1.40 (3H, singlet); about 2 (2H, multiplet); 2.10 (6H, singlet); 2.15 (3H, singlet); 2.6 (2H, broad triplet, J=6 Hz); 3.05 (1H, doublet of doublets, J=15 & 7.5 Hz); 3.30 (1H, doublet of doublets, J=15 & 7.5 Hz); 3.83 and 3.95 (2H, AB Type, J=9 Hz); 4.16 (2H, quartet, J=7.5 Hz); 4.18 (1H, singlet); 4.36 (1H, triplet, J=7.5 Hz); 6.85 (2H, doublet, J=9 Hz); 7.13 (2H, doublet, J=9 Hz).

In the following Preparations 10–38, only those parts of the signals of the nuclear magnetic resonance spectra which are relevant to the compounds prepared are reported.

PREPARATIONS 10–16

The procedure described in Preparation 3 was repeated, but using the appropriate chroman starting material, to prepare the following compounds:

PREPARATION 10

6-hydroxy-5,7,8-trimethyl-2-(4-nitrophenoxymethyl)-chroman

Melting at: 167.5°–169° C.

Mass spectrum (m/e): 343 (M+).

Rf value: 0.60 (thin layer chromatography, silica gel, developing solvent: 9:1 by volume mixture of benzene and ethyl acetate).

Nuclear Magnetic Resonance Spectrum (CDCl$_3$) δ ppm: 4.23 (1H, singlet, D); 7.05 (2H, doublet, J=9 Hz); 8.23 (2H, doublet, J=9 Hz).

PREPARATION 11

6-hydroxy-2,7-dimethyl-2-(4-nitrophenoxymethyl)-chroman

Rf value: 0.45 (thin layer chromatography, silica gel, developing solvent: 10:1 by volume mixture of benzene and ethyl acetate).

Mass spectrum (m/e): 329 (M+).

Nuclear Magnetic Resonance Spectrum (CDCl$_3$) δ ppm: 4.03 (1H, singlet, D); 6.95 (2H, doublet, J=9 Hz); 8.20 (2H, doublet, J=9 Hz).

PREPARATION 12

7-t-butyl-6-hydroxy-2-methyl-2-[2-(4-nitrophenoxy)ethyl]chroman

Rf value: 0.71 (thin layer chromatography, silica gel, developing solvent: 5:1 by volume mixture of benzene and ethyl acetate).

Mass spectrum (m/e): 385 (M+).

Nuclear Magnetic Resonance Spectrum (CDCl$_3$) δ ppm: 4.34 (1H, singlet, D); 6.97 (2H, doublet, J=9 Hz); 8.21 (2H, doublet, J=9 Hz).

PREPARATION 13

6-hydroxy-7,8-dimethoxy-2,5-dimethyl-2-[2-(4-nitrophenoxy)ethyl]chroman

Melting at: 119°-121° C.

Mass spectrum (m/e): 403 (M+).

Rf value: 0.49 (thin layer chromatography, silica gel, developing solvent: 9:1 by volume mixture of benzene and ethyl acetate).

Nuclear Magnetic Resonance Spectrum (CDCl$_3$) δ ppm: 5.43 (1H, singlet, D); 6.99 (2H, doublet, J=9 Hz); 8.23 (2H, doublet, J=9 Hz).

PREPARATION 14

6-hydroxy-2,5,7,8-tetramethyl-2-[2-(4-nitrophenoxy)ethyl]chroman

Rf value: 0.33 (thin layer chromatography, silica gel, developing solvent, 10:1 by volume mixture of benzene and ethyl acetate).

Mass spectrum (m/e): 371 (M+).

Nuclear Magnetic Resonance Spectrum (CDCl$_3$) δ ppm: 4.21 (1H, singlet, D); 6.95 (2H, doublet, J=9 Hz); 8.20 (2H, doublet, J=9 Hz).

PREPARATION 15

2-ethyl-6-hydroxy-5,7,8-trimethyl-2-(4-nitrophenoxymethyl)chroman

Rf value: 0.42 (thin layer chromatography, silica gel, developing solvent: 20:1 by volume mixture of benzene and ethyl acetate).

Mass spectrum (m/e): 371 (M+).

Nuclear Magnetic Resonance Spectrum (CDCl$_3$) δ ppm: 4.20 (1H, singlet, D); 6.98 (2H, doublet, J=9 Hz); 8.18 (2H, doublet, J=9 Hz).

PREPARATION 16

6-hydroxy-2-isobutyl-5,7,8-trimethyl-2-(4-nitrophenoxymethyl)chroman

Rf value: 0.42 (thin layer chromatography, silica gel, developing solvent: 20:1 by volume mixture of benzene and ethyl acetate).

Mass spectrum (m/e): 399 (M+).

Nuclear Magnetic Resonance Spectrum (CDCl$_3$) δ ppm: 4.22 (1H, singlet, D); 6.98 (2H, doublet, J=9 Hz); 8.18 (2H, doublet, J=9 Hz).

PREPARATIONS 17-23

Using the corresponding 6-hydroxy compounds prepared as described in Preparations 10-16 above, the procedure of Preparation 4 was repeated, to give the following 6-acetoxy compounds:

PREPARATION 17

6-acetoxy-5,7,8-trimethyl-2-(4-nitrophenoxymethyl)-chroman

Melting at: 132°-134° C.

Rf value: 0.66 (thin layer chromatography, silica gel, developing solvent: 9:1 by volume mixture of benzene and ethyl acetate).

Mass spectrum (m/e): 385 (M+).

Nuclear Magnetic Resonance Spectrum (CDCl$_3$) δ ppm: 2.31 (3H, singlet); 7.05 (2H, doublet, J=9 Hz); 8.23 (2H, doublet, J=9 Hz).

PREPARATION 18

6-acetoxy-2,7-dimethyl-2-(4-nitrophenoxymethyl)chroman

Rf value: 0.45 (thin layer chromatography, silica gel, developing solvent: 20:1 by volume mixture of benzene and ethyl acetate).

Mass spectrum (m/e): 371 (M+).

Nuclear Magnetic Resonance Spectrum (CDCl$_3$) δ ppm: 2.23 (3H, singlet); 6.95 (2H, doublet, J=9 Hz); 8.20 (2H, doublet, J=9 Hz).

PREPARATION 19

6-acetoxy-7-t-butyl-2-methyl-2-[2-(4-nitrophenoxy)ethyl]chroman

Rf value: 0.21 (thin layer chromatography, silica gel, developing solvent: 50:1 by volume mixture of benzene and ethyl acetate).

Mass spectrum (m/e): 427 (M+).

Nuclear Magnetic Resonance Spectrum (CDCl$_3$) δ ppm: 2.29 (3H, singlet); 6.95 (2H, doublet, J=9 Hz); 8.21 (2H, doublet, J=9 Hz).

PREPARATION 20

6-acetoxy-7,8-dimethoxy-2,5-dimethyl-2-[2-(4-nitrophenoxy)ethyl]chroman

Rf value: 0.45 (thin layer chromatography, silica gel, developing solvent: 9:1 by volume mixture of benzene and ethyl acetate).

Mass spectrum (m/e): 445 (M+).

Nuclear Magnetic Resonance Spectrum (CDCl$_3$) δ ppm: 2.33 (3H, singlet); 6.99 (2H, doublet, J=9 Hz); 8.23 (2H, doublet, J=9 Hz).

PREPARATION 21

6-acetoxy-2,5,7,8-tetramethyl-2-[2-(4-nitrophenoxy)ethyl]chroman

Rf value: 0.38 (thin layer chromatography, silica gel, developing solvent: 10:1 by volume mixture of benzene and ethyl acetate).

Mass spectrum (m/e): 413 (M+).

Nuclear Magnetic Resonance Spectrum (CDCl$_3$) δ ppm: 2.31 (3H, singlet); 6.95 (2H, doublet, J=9 Hz); 8.20 (2H, doublet, J=9 Hz).

PREPARATION 22

6-acetoxy-2-ethyl-5,7,8-trimethyl-2-(4-nitrophenoxymethyl)chroman

Rf value: 0.44 (thin layer chromatography, silica gel, developing solvent: 4:1 by volume mixture of cyclohexane and ethyl acetate).

Mass spectrum (m/e): 413 (M+).

Nuclear Magnetic Resonance Spectrum (CDCl$_3$) δ ppm: 2.31 (3H, singlet); 6.98 (2H, doublet, J=9 Hz); 8.20 (2H, doublet, J=9 Hz).

PREPARATION 23

6-acetoxy-2-isobutyl-5,7,8-trimethyl-2-(4-nitrophenoxymethyl)chroman

Rf value: 0.41 (thin layer chromatography, silica gel, developing solvent: 4:1 by volume mixture of cyclohexane and ethyl acetate).

Mass spectrum (m/e): 441 (M+).

Nuclear Magnetic Resonance Spectrum (CDCl$_3$) δ ppm: 2.32 (3H, singlet); 6.98 (2H, doublet, J=9 Hz); 8.17 (2H, doublet, J=9 Hz).

PREPARATIONS 24–30

Following the procedure described in Preparation 5, but using the appropriate nitrophenoxy compounds prepared as described in Preparations 17–23, the following compounds were prepared:

PREPARATION 24

6-acetoxy-2-(4-aminophenoxymethyl)-5,7,8-trimethylchroman

Melting at 162.5°–164.5° C.

Rf value: 0.11 (thin layer chromatography, silica gel, developing solvent: 9:1 by volume mixture of benzene and ethyl acetate).

Mass spectrum (m/e): 355 (M+).

Nuclear Magnetic Resonance Spectrum (CDCl$_3$) δ ppm: 3.37 (2H, singlet, D); 6.65 (2H, doublet, J=9 Hz); 6.85 (2H, doublet, J=9 Hz).

PREPARATION 25

6-acetoxy-2-(4-aminophenoxymethyl)-2,7-dimethylchroman

Rf value: 0.52 (thin layer chromatography, silica gel, developing solvent: 1:1 by volume mixture of benzene and ethyl acetate).

Mass spectrum (m/e): 341 (M+).

Nuclear Magnetic Resonance Spectrum (CDCl$_3$) δ ppm: 3.30 (2H, singlet, D); 6.60 (2H, doublet, J=9 Hz); 6.76 (2H, doublet, J=9 Hz).

PREPARATION 26

6-acetoxy-2-[2-(4-aminophenoxy)ethyl]-7-t-butyl-2-methylchroman

Rf value: 0.15 (thin layer chromatography, silica gel, developing solvent: 5:1 by volume mixture of benzene and ethyl acetate).

Mass spectrum (m/e): 397 (M+).

Nuclear Magnetic Resonance Spectrum (CDCl$_3$) δ ppm: 2.97–3.53 (2H, broad singlet, D); 6.63 (2H, doublet, J=9 Hz); 6.77 (2H, doublet, J=9 Hz).

PREPARATION 27

6-acetoxy-2-[2-(4-aminophenoxy)ethyl]-7,8-dimethoxy-2,5-dimethylchroman

Rf value: 0.43 (thin layer chromatography, silica gel, developing solvent: 1:1 by volume mixture of benzene and ethyl acetate).

Mass spectrum (m/e): 415 (M+).

Nuclear Magnetic Resonance Spectrum (CDCl$_3$) δ ppm: 3.23 (2H, broad singlet, D); 6.61 (2H, doublet, J=9 Hz); 6.77 (2H, doublet, J=9 Hz).

PREPARATION 28

6-acetoxy-2-[2-(4-aminophenoxy)ethyl]-2,5,7,8-tetramethylchroman

Rf value: 0.14 (thin layer chromatography, silica gel, developing solvent: 10:1 by volume mixture of benzene and ethyl acetate).

Mass spectrum (m/e): 383 (M+).

Nuclear Magnetic Resonance Spectrum (CDCl$_3$) δ ppm: 3.28 (2H, singlet, D); 6.61 (2H, doublet, J=9 Hz); 6.75 (2H, doublet, J=9 Hz).

PREPARATION 29

6-acetoxy-2-(4-aminophenoxymethyl)-2-ethyl-5,7,8-trimethylchroman

Melting at: 123°–124° C.

Rf value: 0.09 (thin layer chromatography, silica gel, developing solvent: 5:1 by volume mixture of cyclohexane and ethyl acetate).

Mass spectrum (m/e): 383 (M+).

Nuclear Magnetic Resonance Spectrum (CDCl$_3$) δ ppm: 2.8–3.5 (2H, broad singlet, D); 6.59 (2H, doublet, J=9 Hz); 6.76 (2H, doublet, J=9 Hz).

PREPARATION 30

6-acetoxy-2-(4-aminophenoxymethyl)-2-isobutyl-5,7,8-trimethylchroman

Melting at: 137°–138° C.

Rf value: 0.11 (thin layer chromatography, silica gel, developing solvent: 4:1 by volume mixture of cyclohexane and ethyl acetate).

Mass spectrum (m/e): 411 (M+).

Nuclear Magnetic Resonance Spectrum (CDCl$_3$) δ ppm: 2.7–3.4 (2H, broad singlet, D); 6.61 (2H, doublet, J=9 Hz); 6.77 (2H, doublet, J=9 Hz).

PREPARATIONS 31–38

Following the procedure described in Preparation 6, but using the appropriate starting materials prepared as described in Preparations 24–30 and 41, the following compounds were prepared:

PREPARATION 31 ethyl 3-[4-(6-acetoxy-5,7,8-trimethylchroman-2-yl-methoxy)-phenyl]-2-chloropropionate Rf value: 0.70 (thin layer chromatography, silica gel, developing solvent: 9:1 by volume mixture of benzene and ethyl acetate).

Mass spectrum (m/e): 474 (M+).

Nuclear Magnetic Resonance Spectrum (CDCl$_3$) δ ppm: 2.7 (2H, doublet of doublets, J=10 & 5 Hz); 3.13 (1H, doublet of doublets, J=15 & 7.5 Hz); 3.30 (1H, doublet of doublets, J=15 & 7.5 Hz); 4.05–4.46 (6H, multiplet).

PREPARATION 32 ethyl 2-chloro-3-{4-[2-(6-hydroxy-2,5,7,8-tetramethylchroman-2-yl)ethoxy]phenyl}propionate Rf value: 0.42 (thin layer chromatography, silica gel, developing solvent: 20:1 by volume mixture of benzene and ethyl acetate).

Mass spectrum (m/e): 460 (M+).

Nuclear Magnetic Resonance Spectrum (CDCl$_3$) δ ppm: 2.6 (2H, broad triplet, J=6 Hz); 3.11 (1H, doublet of doublets, J=15 & 7.5 Hz); 3.27 (1H, doublet of doublets, J=15 & 7.5 Hz); 4.05–4.5 (6H, multiplet).

PREPARATION 33 ethyl 3-[4-(6-acetoxy-2,7-dimethylchroman-2-ylmethoxy)-phenyl]-2-chloropropionate Rf value: 0.45 (thin layer chromatography, silica gel, developing solvent: 20:1 by volume mixture of benzene and ethyl acetate).

Mass spectrum (m/e): 460 (M+).

Nuclear Magnetic Resonance Spectrum (CDCl$_3$) δ ppm: 2.7 (2H, broad triplet, J=6 Hz); 3.12 (1H, doublet of doublets, J=15 & 7.5 Hz); 3.27 (1H, doublet of doublets, J=15 & 7.5 Hz); 3.8–4.45 (5H, multiplet).

PREPARATION 34 ethyl 3-{4-[2-(6-acetoxy-7-t-butyl-2-methylchroman-2-yl)ethoxy]phenyl}-2-chloropropionate Rf value: 0.53 (thin layer chromatography, silica gel, developing solvent: 10:1 by volume mixture of benzene and ethyl acetate).

Mass spectrum (m/e): 516 (M+).

Nuclear Magnetic Resonance Spectrum (CDCl$_3$) δ ppm: 2.7 (2H, broad triplet, J=6 Hz); 3.11 (1H, doublet of doublets, J=15 & 7.5 Hz); 3.27 (1H, doublet of doublets, J=15 & 7.5 Hz); 4.03–4.50 (5H, multiplet).

PREPARATION 35 ethyl 3-{4-[2-(6-acetoxy-7,8-dimethoxy-2,5-dimethylchroman-2-yl)ethoxy]phenyl}-2-chloropropionate Rf value: 0.45 (thin layer chromatography, silica gel, developing solvent: 9:1 by volume mixture of benzene and ethyl acetate).

Mass spectrum (m/e): 534 (M+).

Nuclear Magnetic Resonance Spectrum (CDCl$_3$) δ ppm: 2.6 (2H, broad triplet, J=6 Hz); 3.10 (1H, doublet of doublets, J=15 & 7.5 Hz); 3.27 (1H, doublet of doublets, J=15 & 7.5 Hz); 4.07–4.46 (5H, multiplet).

PREPARATION 36 ethyl 3-{4-[2-(6-acetoxy-2,5,7,8-tetramethylchroman-2-yl)ethoxy]phenyl}-2-chloropropionate Rf value: 0.39 (thin layer chromatography, silica gel, developing solvent: 20:1 by volume mixture of benzene and ethyl acetate).

Mass spectrum (m/e): 502 (M+).

Nuclear Magnetic Resonance Spectrum (CDCl$_3$) δ ppm: 2.6 (2H, broad triplet, J=6 Hz); 3.06 (1H, doublet of doublets, J=15 & 7.5 Hz); 3.32 (1H, doublet of doublets, J=15 & 7.5 Hz); 4.05–4.45 (5H, multiplet).

PREPARATION 37 ethyl 3-[4-(6-acetoxy-2-ethyl-5,7,8-trimethylchroman-2-ylmethoxy)phenyl]-2-chloropropionate Rf value: 0.33 (thin layer chromatography, silica gel, developing solvent: 100:1 by volume mixture of benzene and ethyl acetate).

Mass spectrum (m/e): 502 (M+).

Nuclear Magnetic Resonance Spectrum (CDCl$_3$) δ ppm: 2.6 (2H, broad triplet, J=6 Hz); 3.05 (1H, doublet of doublets, J=15 & 7.5 Hz); 3.30 (1H, doublet of doublets, J=15 & 7.5 Hz); 3.90–4.45 (5H, multiplet).

PREPARATION 38 ethyl 3-[4-(6-acetoxy-2-isobutyl-5,7,8-trimethylchroman-2-ylmethoxy)phenyl]-2-chloropropionate Rf value: 0.44 (thin layer chromatography, silica gel, developing solvent: 100:1 by volume mixture of benzene and ethyl acetate).

Mass spectrum (m/e): 530 (M+).

Nuclear Magnetic Resonance Spectrum (CDCl$_3$) δ ppm: 2.6 (2H, broad triplet, J=7 Hz); 3.05 (1H, doublet of doublets, J=15 & 7.5 Hz); 3.30 (1H, doublet of doublets, J=15 & 7.5 Hz); 3.90–4.45 (5H, multiplet).

PREPARATION 39

2-(6-Benzyloxy-2,5,7,8-tetramethylchroman-2-yl)ethanol

Following the procedure described in Preparation 1, 2-(6-hydroxy-2,5,7,8-tetramethylchroman-2-yl)ethanol was reacted with benzyl bromide and treated and purified to give the title compound.

Rf value: 0.31 (thin layer chromatography, silica gel, developing solvent: 10:1 by volume mixture of benzene and ethyl acetate).

Mass spectrum (m/e): 340 (M+).

Nuclear Magnetic Resonance Spectrum (CDCl$_3$+D$_2$O) δ ppm: 1.31 (3H, singlet); 1.67–2.37 (4H, multiplet); 2.10 (3H, singlet); 2.17 (3H, singlet); 2.23 (3H, singlet); 2.65 (2H, broad triplet, J=6 Hz); 3.90 (2H, triplet, J=6 Hz); 4.72 (2H, singlet); 7.3–7.65 (5H, multiplet).

PREPARATION 40

6-Benzyloxy-2,5,7,8-tetramethyl-2-[2-(4-nitrophenoxy)ethyl]chroman 2-(6-Benzyloxy-2,5,7,8-tetramethylchroman-2-yl)ethanol (prepared as described in Preparation 39) was reacted with p-chloronitrobenzene and the reaction mixture was treated and purified as described in Preparation 2, to give the title compound.

Rf value: 0.43 (thin layer chromatography, silica gel, developing solvent: benzene).

Mass spectrum (m/e): 461 (M+).

Nuclear Magnetic Resonance Spectrum (CDCl$_3$) δ ppm: 1.37 (3H, singlet); 1.90 (2H, triplet, J=6 Hz); 2.11 (3H, singlet); 2.18 (3H, singlet); 2.24 (3H, singlet); 2.0–2.3 (2H, nd); 2.66 (2H, triplet, J=6 Hz); 4.32 (2H, triplet, J=6 Hz); 4.73 (2H, singlet); 6.94 (2H, doublet, J=9 Hz); 7.3–7.65 (5H, multiplet); 8.20 (2H, doublet, J=9 Hz).

PREPARATION 41

2-[2-(4-Aminophenoxy)ethyl]-6-hydroxy-2,5,7,8-tetramethylchroman

6-Benzyloxy-2,5,7,8-tetramethyl-2-[2-(4-nitrophenoxy)ethyl]chroman (prepared as described in Preparation 40) was catalytically reduced and then the reaction mixture was processed as described in Preparation 5. The resulting crude product was purified by silica gel column chromatography and the title compound was obtained from the fractions eluted with a 4:1 by volume mixture of benzene and ethyl acetate.

Rf value: 0.36 (thin layer chromatography, silica gel, developing solvent: 3:2 by volume mixture of benzene and ethyl acetate).

Mass spectrum (m/e): 341 (M+).

Nuclear Magnetic Resonance Spectrum (CDCl$_3$) δ ppm: 1.32 (3H, singlet); 1.87 (2H, triplet, J=6 Hz); 2.10 (6H, singlet); 2.15 (3H, singlet); 2.0–2.3 (nd); 2.64 (2H, broad triplet, J=6 Hz); 3.2–4.1 (2H, broad singlet); 4.12 (3H, triplet, J=6 Hz); 6.60 (2H, doublet, J=9 Hz); 6.75 (2H, doublet, J=9 Hz).

PREPARATION 42

6-Hydroxy-2,5,7,8-tetramethyl-2-(4-nitrophenoxymethyl)chroman-4-one

A mixture of 3.9 g of 2,5-dihydroxy-3,4,6-trimethylacetophenone, 3.9 g of 4-nitrophenoxyacetone, 2.0 g of pyrrolidine and 15 g of toluene was left standing at room temperature for 2 days. Dilute hydrochloric acid was then added to the reaction mixture and the mixture was extracted with diethyl ether. The remaining aqueous layer was again extracted with ethyl acetate and the ethyl acetate extract was added to the ethereal extract. The resulting mixture was dried over anhydrous sodium sulfate. The solvent was distilled off from the mixture. Hexane was added to the resulting residue, and the crystals thus precipitated were collected by filtration. The crystals were subjected to silica gel column chromatography, eluted with a 5:1 by volume mixture of hexane and ethyl acetate, and then recrystallized from ethyl acetate, to yield 6-hydroxy-2,5,7,8-tetramethyl-2-(4-nitrophenoxymethyl)chroman-4-one. Its melting point was 199°–204° C.

Nuclear Magnetic Resonance Spectrum (hexadeuterated dimethyl sulfoxide) δ ppm: 1.43 (3H, singlet); 2.01 (3H, singlet); 2.14 (3H, singlet); 2.46 (3H, singlet); 2.67 (1H, doublet, J=16 Hz); 3.03 (1H, doublet, J=16 Hz); 4.31 (2H, singlet); 7.19 (2H, doublet, J=9 Hz); 7.92 (1H, singlet); 8.21 (2H, doublet, J=9 Hz).

PREPARATION 43

6-Acetoxy-2,5,7,8-tetramethyl-2-(4-nitrophenoxymethyl)chroman-4-one

A mixture of 17.7 g of 5-acetoxy-2-hydroxy-3,4,6-trimethylacetophenone, 14.6 g of 4-nitrophenoxyacetone, 7.5 g of pyrrolidine and 60 ml of benzene was left standing at room temperature for one day, and then the mixture was refluxed for 7 hours using a water separator. At the end of this time, water and ethyl acetate were added to the reaction mixture and the organic layer was separated. It was then dried over anhydrous sodium sulfate. The solvent was distilled off and the resulting residue was subjected to silica gel column chromatography, eluted with a 2:1 by volume mixture of hexane and ethyl acetate, to yield 6-acetoxy-2,5,7,8-tetramethyl-2-(4-nitrophenoxymethyl)chroman-4-one.

Rf value: 0.17 (thin layer chromatography, silica gel, developing solvent: hexane:ethyl acetate=3:1 by volume).

Nuclear Magnetic Resonance Spectrum (CDCl$_3$) δ ppm: 1.56 (3H, singlet); 2.10 (6H, singlet); 2.36 (3H, singlet); 2.43 (3H, singlet); 2.70 (1H, doublet, J=15 Hz); 3.06 (1H, doublet, J=15 Hz); 4.11 (1H, doublet, J=10 Hz); 4.24 (1H, doublet, J=10 Hz); 6.98 (2H, doublet, J=9 Hz); 8.20 (2H, doublet, J=9 Hz).

PREPARATION 44

6-Acetoxy-2-(4-aminophenoxymethyl)-2,5,7,8-tetramethylchroman-4-one

Hydrogen gas was passed for 2 hours through a mixture of 3.6 g of 6-acetoxy-2,5,7,8-tetramethyl-2-(4-nitrophenoxymethyl)chroman-4-one, 1 g of 10% w/w palladium-on-carbon and 100 ml of methanol at room temperature under atmospheric pressure. The catalyst was then removed by filtration and the filtrate was condensed by evaporation under reduced pressure. The residue was subjected to silica gel column chromatography, eluted with a 2:1 by volume mixture of hexane and ethyl acetate, and the resulting crude product was recrystallized from acetone, to yield 6-acetoxy-2-(4-aminophenoxymethyl)-2,5,7,8-tetramethylchroman-4-one. Its melting point was 177°–178° C.

Nuclear Magnetic Resonance Spectrum (CDCl$_3$) δ ppm: 1.49 (3H, singlet); 2.09 (3H, singlet); 2.12 (3H, singlet); 2.33 (3H, singlet); 2.42 (3H, singlet); 2.65 (1H, doublet, J=15 Hz); 3.07 (1H, doublet, J=15 Hz); 3.2–3.6 (2H, broad singlet); 3.91 (1H, doublet, J=10 Hz); 4.06 (1H, doublet, J=10 Hz); 6.60 (2H, doublet, J=9 Hz); 6.75 (2H, doublet, J=9 Hz).

PREPARATION 45

Ethyl 3-[4-(6-acetoxy-2,5,7,8-tetramethyl-4-oxochroman-2-ylmethoxy)phenyl]-2-chloropropionate 3 ml of concentrated hydrochloric acid and then an aqueous solution of 700 mg of sodium nitrite in 1.1 ml of water were added dropwise to a mixture of 2.1 g of 6-acetoxy-2-(4-aminophenoxymethyl)-2,5,7,8-tetramethylchroman-4-one and 26 ml of acetone, whilst cooling with ice. The mixture was stirred for 30 minutes at the same temperature. 7 g of ethyl acrylate were then added, after which cuprous oxide was added gradually, while keeping the reaction temperature at 30°–35° C. The reaction mixture was then stirred for 1 hour at room temperature. Water and benzene were added to the reaction mixture. The benzene layer was separated, washed with water and dried over anhydrous sodium sulfate. Benzene was distilled off and the residue was subjected to silica gel column chromatography, eluted with a 3:1 by volume mixture of hexane and ethyl acetate, to yield ethyl 3-[4-(6-acetoxy-2,5,7,8-tetramethyl-4-oxochroman-2-ylmethoxy)phenyl]-2-chloropropionate.

Rf value: 0.21 (thin layer chromatography, silica gel, developing solvent: hexane:ethyl acetate=3:1 by volume).

Nuclear Magnetic Resonance Spectrum (CDCl$_3$) δ ppm: 1.24 (3H, triplet, J=7 Hz); 1.51 (3H, singlet); 2.10 (3H, singlet); 2.12 (3H, singlet); 2.34 (3H, singlet); 2.43 (3H, singlet); 2.67 (1H, doublet, J=15 Hz); 3.07 (1H, doublet of doublets, J=7.5 & 15 Hz); 3.10 (1H, doublet, J=15 Hz); 3.32 (1H, doublet of doublets, J=7.5 & 15 Hz); 4.06 (2H, singlet); 4.18 (2H, quartet, J=7 Hz); 3.9–4.5 (1H, nd); 6.84 (2H, doublet, J=9 Hz); 7.15 (2H, doublet, J=9 Hz).

PREPARATION 46

7-t-Butyl-6-hydroxy-2-methyl-2-(4-nitrophenoxymethyl)chroman-4-one

In a similar manner to Preparation 42, a mixture of 2.0 g of 4-t-butyl-2,5-dihydroxyacetophenone, 1.9 g of 4-nitrophenoxyacetone, 1.0 g of pyrrolidine and 10 ml of benzene was allowed to stand at room temperature for 2 days. To the reaction mixture was then added 10% w/w hydrochloric acid, and the crude product was extracted with ethyl acetate. The organic extract was dried over anhydrous sodium sulfate, and the residue obtained by removing the solvent was subjected to silica gel column chromatography, eluted with a 10:1 by volume mixture of benzene and ethyl acetate. The resulting crude crystals were washed with cyclohexane to give the desired 7-t-butyl-6-hydroxy-2-methyl-2-(4-nitrophenoxymethyl)chroman-4-one.

Melting point: 205°–209° C.

Nuclear Magnetic Resonance Spectrum (hexadeuterated acetone) δ ppm: 1.39 (3H, singlet); 1.53 (9H, singlet); 2.70 (1H, doublet, J=16.5 Hz); 3.05 (1H, doublet, J=16.5 Hz); 4.37 (2H, singlet); 6.80 (1H, singlet); 7.18 (2H, doublet, J=10 Hz); 7.22 (1H, singlet); 8.22 (2H, doublet, J=10 Hz); 8.31 (1H, singlet, D).

PREPARATION 47

6-Acetoxy-7-t-butyl-2-methyl-2-(4-nitrophenoxymethyl)chroman-4-one

A mixture of 1.7 g of 7-t-butyl-6-hydroxy-2-methyl-2-(4-nitrophenoxymethyl)chroman-4-one, 1 ml of acetic anhydride and 10 ml of pyridine was allowed to stand at room temperature for 1 day. The reaction mixture was then poured into ice-water and stirred for 2 hours, and the crude substance was extracted with benzene. The organic solution was washed successively with 3N hydrochloric acid, water, a saturated aqueous solution of sodium bicarbonate and water, and dried over anhydrous sodium sulfate. The solvent was evaporated off under reduced pressure, and the crude product thus obtained was recrystallized from a 10:1 by volume mixture of benzene and ethyl acetate, to give the desired 6-acetoxy-7-t-butyl-2-methyl-2-(4-nitrophenoxymethyl)chroman-4-one.

Melting point: 82°–84° C.

Nuclear Magnetic Resonance Spectrum (hexadeuterated acetone) δ ppm: 1.33 (9H, singlet); 1.57 (3H, singlet); 2.33 (3H, singlet); 2.82 (1H, doublet, J=16.5 Hz); 3.13 (1H, doublet, J=16.5 Hz); 4.42 (2H, singlet); 6.93 (1H, singlet); 7.25 (2H, doublet, J=9 Hz); 7.44 (1H, singlet); 8.22 (2H, doublet, J=9 Hz).

PREPARATION 48

6-Acetoxy-2-(4-aminophenoxymethyl)-7-t-butyl-2-methylchroman-4-one

In a similar manner to Preparation 44, 0.9 g of 6-acetoxy-7-t-butyl-2-methyl-2-(4-nitrophenoxymethyl)-chroman-4-one was dissolved in 20 ml of acetic acid, and catalytic hydrogenation was performed for 5.5 hours with a hydrogen pressure of 45–55 lb/sq. inch (3.1–3.8 bars), using Pearl's apparatus, in the presence of 0.4 g of 10% w/w palladium-on-carbon. The palladium-on-carbon was removed by filtration from the reaction mixture and washed with acetic acid. The filtrate and the washings were combined, and the mixture was poured into ice-water, neutralized with sodium carbonate, and extracted with benzene. The benzene extract was washed with water and dried over anhydrous sodium sulfate. The solvent was distilled off, and the residue was subjected to silica gel column chromatography, eluted with a 5:1 by volume mixture of benzene and ethyl acetate, to give the desired 6-acetoxy-2-(4-aminophenoxymethyl)-7-t-butyl-2-methylchroman-4-one.

Rf value: 0.24 (thin layer chromatography, silica gel, developing solvent: benzene:ethyl acetate=5:1 by volume).

Nuclear Magnetic Resonance Spectrum (CDCl$_3$) δ ppm: 1.35 (9H, singlet); 1.52 (3H, singlet); 2.30 (3H, singlet); 2.67 (1H, doublet, J=16.5 Hz); 3.07 (1H, doublet, J=16.5 Hz); 3.20–3.60 (2H, broad, D); 3.92 (1H, doublet, J=10.5 Hz); 4.07 (1H, doublet, J=10.5 Hz); 6.58 (2H, doublet, J=10 Hz); 6.75 (2H, doublet, J=10 Hz); 6.98 (1H, singlet); 7.49 (1H, singlet).

PREPARATION 49

Ethyl 3-[4-(6-acetoxy-7-t-butyl-2-methyl-4-oxochroman-2-ylmethoxy)phenyl]-2-chloropropionate In a similar manner to Preparation 45, to a mixture of 0.42 g of 6-acetoxy-2-(4-aminophenoxymethyl)-7-t-butyl-2-methylchroman-4-one and 5 ml of acetone were added dropwise, whilst cooling with ice, 0.2 ml of concentrated hydrochloric acid and then a solution of 0.09 g of sodium nitrite in 0.5 ml of water. 1.1 g of ethyl acrylate were then added dropwise, after which 16 mg of cuprous oxide were added gradually to the mixture, whilst keeping its temperature at 40°–43° C. Evolution of nitrogen ceased after about 30 minutes. Benzene was added to the reaction mixture, and the organic layer was separated. The resulting benzene extract was washed with water and dried over anhydrous sodium sulfate. The residue after evaporation of the benzene was subjected to silica gel column chromatography, eluted with a 20:1 by volume mixture of benzene and ethyl acetate, to give the desired ethyl 3-[4-(6-acetoxy-7-t-butyl-2-methyl-4-oxochroman-2-ylmethoxy)-phenyl]-2-chloropropionate.

Rf value: 0.61 (thin layer chromatography, silica gel, developing solvent: benzene:ethyl acetate=5:1 by volume).

Nuclear Magnetic Resonance Spectrum (CDCl$_3$) δ ppm: 1.25 (3H, triplet, J=7 Hz); 1.35 (9H, singlet); 1.55 (3H, singlet); 2.32 (3H, singlet); 2.70 (1H, doublet, J=16.5 Hz); 2.95–3.50 (3H, multiplet); 3.90–4.50 (5H, multiplet); 6.87 (2H, doublet, J=9 Hz); 7.00 (1H, singlet); 7.17 (2H, doublet, J=9 Hz); 7.50 (1H, singlet).

We claim:

1. Compounds of formula (I):

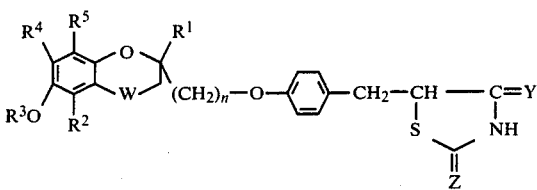

in which:
R$^1$ and R$^2$ are the same or different and each represents hydrogen or a C$_1$–C$_5$ alkyl group;
R$^3$ represents hydrogen; C$_1$–C$_6$ aliphatic acyl; (C$_5$–C$_7$ cycloalkane)carbonyl; benzoyl, benzoyl substituted with one to three substituents selected from the group of C$_1$–C$_4$ alkyl, C$_1$–C$_4$ alkoxy, hydroxy, halogen, nitro, amino and di(C$_1$–C$_4$ alkyl)amino; naphthoyl; 4–7 membered heterocyclic acyl wherein heterocyclic moiety has O, S or N hetero atoms; phenyl(C$_2$–C$_3$)aliphatic acyl; cinnamoyl; (C$_1$–C$_6$ alkoxy)carbonyl; or benzoyloxycarbonyl;
R$^4$ and R$^5$ are the same or different and each represents hydrogen, a C$_1$–C$_5$ alkyl group or a C$_1$–C$_5$ alkoxy group, or R$^4$ and R$^5$ together represent a C$_1$–C$_4$ alkylenedioxy group;
n is 1, 2 or 3;
W represents the —CH$_2$—, >CO or >CH—OR$^6$ group (in which R$^6$ represents any one of the atoms or groups defined for R$^3$ and may be the same as or different from R$^3$); and
Y and Z are the same or different and each represents the oxygen atom or the imino group; and pharmaceutically acceptable salts thereof.

2. Compounds as claimed in claim 1, in which; R$^3$ represents hydrogen, a C$_1$–C$_6$ aliphatic acyl group, one of said aromatic acyl groups or one of said heterocyclic acyl groups.

3. Compounds as claimed in claim 1, in which: Y represents an oxygen atom; R$^1$ and R$^2$ are the same or different and each represents hydrogen or a C$_1$–C$_5$ alkyl group; R$^3$ represents hydrogen, a C$_1$–C$_6$ aliphatic acyl group, one of said aromatic acyl groups or a pyridinecarbonyl group; and R$^4$ and R$^5$ are the same or different and each represents hydrogen, a C$_1$–C$_5$ alkyl group or a C$_1$ or C$_2$ alkoxy group.

4. Compounds as claimed in claim 3, in which: R$^1$, R$^2$, R$^4$ and R$^5$ are the same or different and each represents hydrogen or a C$_1$–C$_5$ alkyl group; n is 1 or 2; and W represents the —CH$_2$— or >CO group.

5. Compounds as claimed in claim 4, in which R$^3$ represents a hydrogen atom, a C$_1$–C$_5$ aliphatic acyl group, or the benzoyl or nicotinoyl group.

6. Compounds as claimed in claim 5, in which: R$^1$ and R$^4$ are the same or different and each represents a C$_1$–C$_5$ alkyl group; R$^2$ and R$^5$ are the same or different and each represents the hydrogen atom or the methyl group; and R$^3$ represents hydrogen or a C$_1$–C$_4$ aliphatic acyl group.

7. Compounds as claimed in claim 1, in which: W represents the —CH$_2$— or >CO group; Y and Z both represent oxygen atoms; n is 1 or 2; R$^1$ and R$^4$ are the same or different and each represents a C$_1$–C$_4$ alkyl group; R$^2$ and R$^5$ are the same or different and each represents the hydrogen atom or the methyl group; and R$^3$ represents hydrogen or a C$_1$–C$_4$ aliphatic acyl group.

8. Compounds as claimed in claim 7, in which n is 1.

9. Compounds as claimed in claim 7 or claim 8, in which W represents the —CH$_2$— group.

10. Compounds as claimed in claim 1, selected from the group consisting of:
5-[4-(6-hydroxy-2,5,7,8-tetramethylchroman-2-ylmethoxy)benzyl]thiazolidine-2,4-dione
5-[4-(2-ethyl-6-hydroxy-5,7,8-trimethylchroman-2-ylmethoxy)benzyl]thiazolidine-2,4-dione
5-[4-(6-hydroxy-5,7,8-trimethylchroman-2-ylmethoxy)benzyl]thiazolidine-2,4-dione
5-{4-[2-(6-hydroxy-2,5,7,8-tetramethylchroman-2-yl)ethoxy]benzyl}thiazolidine-2,4-dione
5-{4-[2-(7-t-butyl-6-hydroxy-2-methylchroman-2-yl)ethoxy]benzyl}thiazolidine-2,4-dione
5-{4-[2-(6-hydroxy-7,8-dimethoxy-2,5-dimethylchroman-2-yl)ethoxy]benzyl}thiazolidine-2,4-dione
5-[4-(6-hydroxy-2,7-dimethylchroman-2-ylmethoxy)benzyl]thiazolidine-2,4-dione
5-[4-(6-hydroxy-2-isobutyl-5,7,8-trimethylchroman-2-ylmethoxy)benzyl]thiazolidine-2,4-dione
5-[4-(6-hydroxy-2,5,7,8-tetramethylchroman-2-ylmethoxy)benzyl]-2-iminothiazolidin-4-one
5-[4-(7-t-butyl-6-hydroxy-2-methylchroman-2-ylmethoxy)benzyl]-2-iminothiazolidin-4-one
5-[4-(2-ethyl-6-hydroxy-5,7,8-trimethylchroman-2-ylmethoxy)benzyl]-2-iminothiazolidin-4-one
5-[4-(6-hydroxy-5,7,8-trimethylchroman-2-ylmethoxy)benzyl]-2-iminothiazolidin-4-one
5-[4-(6-hydroxy-2,7-dimethylchroman-2-ylmethoxy)benzyl]-2-iminothiazolidin-4-one
5-[4-(6-acetoxy-2,5,7,8-tetramethylchroman-2-ylmethoxy)benzyl]thiazolidine-2,4-dione
5-[4-(6-benzoyloxy-2,5,7,8-tetramethylchroman-2-ylmethoxy)benzyl]thiazolidine-2,4-dione
5-[4-(6-butyryloxy-2,5,7,8-tetramethylchroman-2-ylmethoxy)benzyl]thiazolidine-2,4-dione
5-[4-(2,5,7,8-tetramethyl-6-nicotinoyloxychroman-2-ylmethoxy)benzyl]thiazolidine-2,4-dione
5-[4-(6-hydroxy-2,5,7,8-tetramethyl-4-oxochroman-2-ylmethoxy)benzyl]thiazolidine-2,4-dione
5-[4-(7-t-butyl-6-hydroxy-2-methyl-4-oxochroman-2-ylmethoxy)benzyl]thiazolidine-2,4-dione
5-[4-(6-hydroxy-2-isobutyl-5,7,8-trimethyl-4-oxochroman-2-ylmethoxy)benzyl]thiazolidine-2,4-dione
5-[4-(6-hydroxy-2,5,7,8-tetramethyl-4-oxochroman-2-ylmethoxy)benzyl]-2-iminothiazolidin-4-one
5-[4-(7-t-butyl-6-hydroxy-2-methyl-4-oxochroman-2-ylmethoxy)benzyl]-2-iminothiazolidin-4-one
5-[4-(6-hydroxy-2-isobutyl-5,7,8-trimethyl-4-oxochroman-2-ylmethoxy)benzyl]-2-iminothiazolidin-4-one
5-[4-(6-acetoxy-2,5,7,8-tetramethyl-4-oxochroman-2-ylmethoxy)benzyl]thiazolidine-2,4-dione
5-[4-(6-acetoxy-5,7,8-trimethylchroman-2-ylmethoxy)benzyl]-2-iminothiazolidin-4-one
5-{4-[2-(6-acetoxy-7-t-butyl-2-methylchroman-2-yl)ethoxy]benzyl}-2-iminothiazolidin-4-one
5-{4-[2-(6-acetoxy-7,8-dimethoxy-2,5-dimethylchroman-2-yl)ethoxy]benzyl}-2-iminothiazolidin-4-one
and pharmaceutically acceptable salts thereof.

11. The compound as claimed in claim 1, 5-[4-(6-hydroxy-2,5,7,8-tetramethylchroman-2-ylmethoxy)benzyl]thiazolidine-2,4-dione and pharmaceutically acceptable salts thereof.

12. The compound as claimed in claim 1,

5-[4-(2-ethyl-6-hydroxy-5,7,8-trimethylchroman-2-ylmethoxy)benzyl]thiazolidine-2,4-dione and pharmaceutically acceptable salts thereof.

13. The compound as claimed in claim 1,
5-{4-[2-(7-t-butyl-6-hydroxy-2-methylchroman-2-yl)ethoxy]benzyl}thiazolidine-2,4-dione and pharmaceutically salts thereof.

14. The compound as claimed in claim 1,
5-[4-(6-hydroxy-2-isobutyl-5,7,8-trimethylchroman-2-ylmethoxy)benzyl]thiazolidine-2,4-dione and pharmaceutically acceptable salts thereof.

15. The compound as claimed in claim 1,
5-[4-(6-acetoxy-2,5,7,8-tetramethylchroman-2-ylmethoxy)benzyl]thiazolidine-2,4-dione and pharmaceutically acceptable salts thereof.

16. The compound as claimed in claim 1,
5-[4-(6-butyryloxy-2,5,7,8-tetramethylchroman-2-ylmethoxy)benzyl]thiazolidine-2,4-dione and pharmaceutically acceptable salts thereof.

17. The compound as claimed in claim 1,
5-[4-(6-hydroxy-2,5,7,8-tetramethyl-4-oxochroman-2-ylmethoxy)benzyl]thiazolidine-2,4-dione and pharmaceutically acceptable salts thereof.

18. The compound as claimed in claim 1,
5-[4-(7-t-butyl-6-hydroxy-2-methyl-4-oxochroman-2-ylmethoxy)benzyl]thiazolidine-2,4-dione and pharmaceutically acceptable salts thereof.

19. Compounds of formula (Ia):

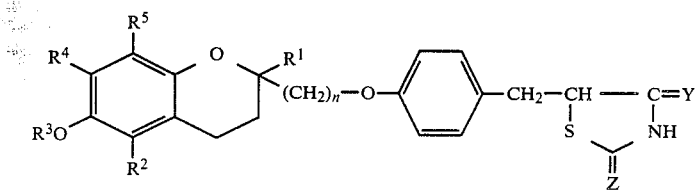

(Ia)

in which:
$R^1$ and $R^2$ are the same or different and each represents hydrogen or a $C_1$–$C_5$ alkyl group;
$R^3$ represents hydrogen; $C_1$–$C_6$ aliphatic acyl; ($C_5$–$C_7$ cycloalkane)carbonyl; benzoyl, benzoyl substituted with one to three substitutents selected from the group of $C_1$–$C_4$ alkyl, $C_1$–$C_4$ alkoxy, hydroxy, halogen, nitro, amino and di($C_1$–$C_4$ alkyl)amino; naphthoyl; 4–7 membered heterocyclic acyl wherein heterocyclic moiety has O, S or N hetero atoms; phenyl($C_2$–$C_3$)aliphatic acyl; cinnamoyl; ($C_1$–$C_6$ alkoxy)carbonyl; or benzoyloxycarbonyl;
$R^4$ and $R^5$ are the same or different and each represents hydrogen, a $C_1$–$C_5$ alkyl group or a $C_1$–$C_5$ alkoxy group, or $R^4$ and $R^5$ together represent a $C_1$–$C_4$ alkylenedioxy group;
n is 1, 2 or 3; and
Y and Z are the same or different and each represents the oxygen atom or the imino group; and pharmaceutically acceptable salts thereof.

20. Compounds of formula (Ib):

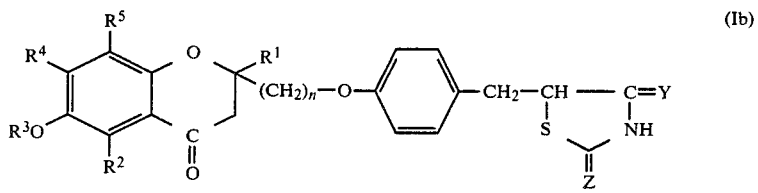

(Ib)

in which:
$R^1$ and $R^2$ are the same or different and each represents hydrogen or a $C_1$–$C_5$ alkyl group;
$R^3$ represents hydrogen; $C_1$–$C_6$ aliphatic acyl; ($C_5$–$C_7$ cycloalkane)carbonyl; benzoyl, benzoyl substituted with one to three substituents selected from the group of $C_1$–$C_4$ alkyl, $C_1$–$C_4$ alkoxy, hydroxy, halogen, nitro, amino and di($C_1$–$C_4$ alkyl)amino; naphthoyl; 4–7 membered heterocyclic acyl wherein heterocyclic moiety has O, S or N hetero atoms; phenyl($C_2$–$C_3$)aliphatic acyl; cinnamoyl; ($C_1$–$C_6$ alkoxy)carbonyl; or benzoyloxycarbonyl;
$R^4$ and $R^5$ are the same or different and each represents hydrogen, a $C_1$–$C_5$ alkyl group or a $C_1$–$C_5$ alkoxy group, or $R^4$ and $R^5$ together represent a $C_1$–$C_4$ alkylenedioxy group;
n is 1, 2 or 3; and
Y and Z are the same or different and each represents the oxygen atom or the imino group; and pharmaceutically acceptable salts thereof.

21. Compounds of formula (Ic):

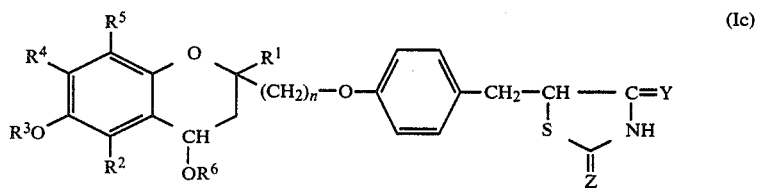

(Ic)

in which:
$R^1$ and $R^2$ are the same or different and each represents hydrogen or a $C_1$–$C_5$ alkyl group;
$R^3$ represents hydrogen; $C_1$–$C_6$ aliphatic acyl; ($C_5$–$C_7$ cycloalkane)carbonyl; benzoyl, benzoyl substituted with one to three substituents selected from the group of $C_1$–$C_4$ alkyl, $C_1$–$C_4$ alkoxy, hydroxy, halogen, nitro, amino and di($C_1$-$C_4$ alkyl)amino; naphthoyl; 4-7 membered heterocyclic acyl wherein heterocyclic moiety has O, S or N hetero atoms; phenyl($C_2$-$C_3$)aliphatic acyl; cinnamoyl; ($C_1$-$C_6$ alkoxy)carbonyl; or benzoyloxycarbonyl;

$R^4$ and $R^5$ are the same or different and each represents hydrogen, a $C_1$-$C_5$ alkyl group or a $C_1$-$C_5$ alkoxy group, or $R^4$ and $R^5$ together represent a $C_1$-$C_4$ alkylenedioxy group;

n is 1, 2 or 3;

$R^6$ represents any one of the atoms or groups defined for $R^3$ and may be the same as or different from $R^3$; and Y and Z are the same or different and each represents the oxygen atom or the imino group; and pharmaceutically acceptable salts thereof.

22. Compounds as claimed in claim 1 or claim 19, which are salts with cations.

23. Compounds as claimed in claim 1 or claim 19, in the form of the sodium salt.

24. A pharmaceutical composition for the treatment of hyperlipaemia or hyperglycaemia, which comprises at least one active compound in admixture with a pharmaceutically acceptable carrier or diluent, wherein said active compound is selected from compounds of formula (I):

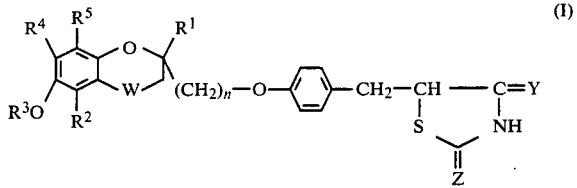

in which:

$R^1$ and $R^2$ are the same or different and each represents hydrogen or a $C_1$-$C_5$ alkyl group;

$R^3$ represents hydrogen; $C_1$-$C_6$ aliphatic acyl; ($C_5$-$C_7$ cycloalkane)carbonyl; benzoyl, benzoyl substituted with one to three substituents selected from the group of $C_1$-$C_4$ alkyl, $C_1$-$C_4$ alkoxy, hydroxy, halogen, nitro, amino and di($C_1$-$C_4$ alkyl)amino; naphthoyl; 4-7 membered heterocyclic acyl wherein heterocyclic moiety has O, S or N hetero atoms; phenyl($C_2$-$C_3$)aliphatic acyl; cinnamoyl; ($C_1$-$C_6$ alkoxy)carbonyl; or benzoyloxycarbonyl;

$R^4$ and $R^5$ are the same or different and each represents hydrogen, a $C_1$-$C_5$ alkyl group or a $C_1$-$C_5$ alkoxy group, or $R^4$ and $R^5$ together represent a $C_1$-$C_4$ alkylenedioxy group;

n is 1, 2 or 3;

W represents the —$CH_2$—, >CO or >CH—$OR^6$ group (in which $R^6$ represents any one of the atoms or groups defined for $R^3$ and may be the same as or different from $R^3$); and Y and Z are the same or different and each represents the oxygen atom or the imino group; and pharmaceutically acceptable salts thereof.

25. Compositions as claimed in claim 24, in which: $R^3$ represents hydrogen, a $C_1$-$C_6$ aliphatic acyl group, one of said aromatic acyl groups or one of said heterocyclic acyl groups.

26. Compositions as claimed in claim 24, in which: Y represents an oxygen atom; $R^1$ and $R^2$ are the same or different and each represents hydrogen or a $C_1$-$C_5$ alkyl group; $R^3$ represents hydrogen, a $C_1$-$C_6$ aliphatic acyl group, one of said aromatic acyl groups or a pyridinecarbonyl group; and $R^4$ and $R^5$ are the same or different and each represents hydrogen, a $C_1$-$C_5$ alkyl group or a $C_1$ or $C_2$ alkoxy group.

27. Compositions as claimed in claim 26, in which: $R^1$, $R^2$, $R^4$ and $R^5$ are the same or different and each represents hydrogen or a $C_1$-$C_5$ alkyl group; n is 1 or 2; and W represents the —$CH_2$— or >CO group.

28. Compositions as claimed in claim 27, in which $R^3$ represents a hydrogen atom, a $C_1$-$C_5$ aliphatic acyl group, or the benzoyl or nicotinoyl group.

29. Compositions as claimed in claim 28, in which: $R^1$ and $R^4$ are the same or different and each represents a $C_1$-$C_5$ alkyl group; $R^2$ and $R^5$ are the same or different and each represents the hydrogen atom or the methyl group; and $R^3$ represents hydrogen or a $C_1$-$C_4$ aliphatic acyl group.

30. Compositions as claimed in claim 24, in which: W represents the —$CH_2$— or >CO group; Y and Z both represent oxygen atoms; n is 1 or 2; $R^1$ and $R^4$ are the same or different and each represents a $C_1$-$C_4$ alkyl group; $R^2$ and $R^5$ are the same or different and each represents the hydrogen atom or the methyl group; and $R^3$ represents hydrogen or a $C_1$-$C_4$ aliphatic acyl group.

31. Compositions as claimed in claim 30, in which n is 1.

32. Compositions as claimed in claim 30 or claim 17, in which W represents the —$CH_2$— group.

33. Compositions as claimed in claim 24, wherein said active compound is selected from the group consisting of:

5-[4-(6-hydroxy-2,5,7,8-tetramethylchroman-2-ylmethoxy)benzyl]thiazolidine-2,4-dione 5-[4-(2-ethyl-6-hydroxy-5,7,8-trimethylchroman-2-ylmethoxy)benzyl]thiazolidine-2,4-dione 5-[4-(6-hydroxy-5,7,8-trimethylchroman-2-ylmethoxy)benzyl]thiazolidine-2,4-dione 5-{4-[2-(6-hydroxy-2,5,7,8-tetramethylchroman-2-yl)ethoxy]benzyl}thiazolidine-2,4-dione 5-{4-[2-(7-t-butyl-6-hydroxy-2-methylchroman-2-yl)ethoxy]benzyl}thiazolidine-2,4-dione 5-{4-[2-(6-hydroxy-7,8-dimethoxy-2,5-dimethylchroman-2-yl)ethoxy]benzyl}thiazolidine-2,4-dione 5-[4-(6-hydroxy-2,7-dimethylchroman-2-ylmethoxy)benzyl]thiazolidine-2,4-dione 5-[4-(6-hydroxy-2-isobutyl-5,7,8-trimethylchroman-2-ylmethoxy)benzyl]thiazolidine-2,4-dione 5-[4-(6-hydroxy-2,5,7,8-tetramethylchroman-2-ylmethoxy)benzyl]-2-iminothiazolidin-4-one 5-[4-(7-t-butyl-6-hydroxy-2-methylchroman-2-ylmethoxy)benzyl]-2-iminothiazolidin-4-one 5-[4-(2-ethyl-6-hydroxy-5,7,8-trimethylchroman-2-ylmethoxy)benzyl]-2-iminothiazolidin-4-one 5-[4-(6-hydroxy-5,7,8-trimethylchroman-2-ylmethoxy)benzyl]-2-iminothiazolidin-4-one 5-[4-(6-hydroxy-2,7-dimethylchroman-2-ylmethoxy)benzyl]-2-iminothiazolidin-4-one 5-[4-(6-acetoxy-2,5,7,8-tetramethylchroman-2-ylmethoxy)benzyl]thiazolidine-2,4-dione 5-[4-(6-benzoyloxy-2,5,7,8-tetramethylchroman-2-ylmethoxy)benzyl]thiazolidine-2,4-dione 5-[4-(6-butyryloxy-2,5,7,8-tetramethylchroman-2-ylmethoxy)benzyl]thiazolidine-2,4-dione 5-[4-(2,5,7,8-tetramethyl-6-nicotinoyloxychroman-2-ylmethoxy)benzyl]thiazolidine-2,4-dione 5-[4-(6-hydroxy-2,5,7,8-tetramethyl-4-oxochroman-2-ylmethoxy)benzyl]thiazolidine-2,4-dione 5-[4-(7-t-butyl-6-hydroxy-2-methyl-4-oxochroman-2-ylmethoxy)benzyl]thiazolidine-2,4-dione 5-[4-(6-hydroxy-2-isobutyl-5,7,8-trimethyl-4-oxochroman-2-ylmethoxy)benzyl]thiazolidine-2,4-dione 5-[4-(6-hydroxy-2,5,7,8-tetramethyl-4-oxochroman-2-ylmethoxy)benzyl]-2-iminothiazolidin-4-one 5-[4-(7-t-butyl-6-hydroxy-2-methyl-4-oxochroman-2-ylmethoxy)benzyl]-2-iminothiazolidin-4-one 5-[4-(6-hydroxy-2-isobutyl-5,7,8-trimethyl-4-oxochroman-2-ylmethoxy)benzyl]-2-iminothiazolidin-4-one 5-[4-(6-acetoxy-2,5,7,8-tetramethyl-4-oxochroman-2-ylmethoxy)benzyl]thiazolidine-2,4-dione 5-[4-(6-acetoxy-5,7,8-trimethylchroman-2-ylmethoxy)benzyl]-2-iminothiazolidin-4-one 5-{4-[2-(6-acetoxy-7-t-butyl-2-methylchroman-2-yl)ethoxy]benzyl}-2-iminothiazolidin-4-one 5-{4-[2-(6-actoxy-7,8-dimethoxy-2,5-dimethylchroman-2-yl)ethoxy]benzyl}-2-iminothiazolidin-4-one and pharmaceutically acceptable salts thereof.

34. Compositions as claimed in claim 24, wherein said active compound is selected from the group consisting of:

5-[4-(6-hydroxy-2,5,7,8-tetramethylchroman-2-ylmethoxy)benzyl]thiazolidine-2,4-dione 5-[4-(2-ethyl-6-hydroxy-5,7,8-trimethylchroman-2-ylmethoxy)benzyl]thiazolidine-2,4-dione 5-{4-[2-(7-t-butyl-6-hydroxy-2-methylchroman-2-yl)ethoxy]benzyl}thiazolidine-2,4-dione 5-[4-(6-hydroxy-2-isobutyl-5,7,8-trimethylchroman-2-ylmethoxy)benzyl]thiazolidine-2,4-dione 5-[4-(6-acetoxy-2,5,7,8-tetramethylchroman-2-ylmethoxy)benzyl]thiazolidine-2,4-dione 5-[4-(6-butyryloxy-2,5,7,8-tetramethylchroman-2-ylmethoxy)benzyl]thiazolidine-2,4-dione 5-[4-(6-hydroxy-2,5,7,8-tetramethyl-4-oxochroman-2-ylmethoxy)benzyl]thiazolidine-2,4-dione 5-[4-(7-t-butyl-6-hydroxy-2-methyl-4-oxochroman-2-ylmethoxy)benzyl]thiazolidine-2,4-dione and pharmaceutically acceptable salts thereof.

35. Compositions as claimed in claim 24, in which said active compound is selected from compounds of formula (Ia):

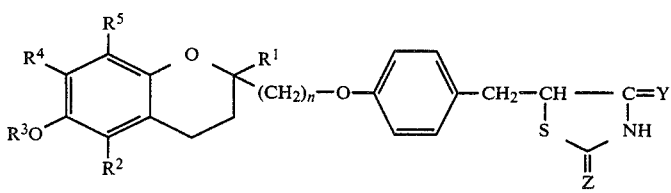

in which:

$R^1$ and $R^2$ are the same or different and each represents hydrogen or a $C_1$-$C_5$ alkyl group;

$R^3$ represents hydrogen; $C_1$-$C_6$ aliphatic acyl; ($C_5$-$C_7$ cycloalkane)carbonyl; benzoyl, benzoyl substituted with one to three substituents selected from the group of $C_1$-$C_4$ alkyl, $C_1$-$C_4$ alkoxy, hydroxy, halogen, nitro, amino and di($C_1$-$C_4$ alkyl)amino; naphthoyl; 4–7 membered heterocyclic acyl wherein heterocyclic moiety has O, S or N hetero atoms; phenyl($C_2$-$C_3$)aliphatic acyl; cinnamoyl; ($C_1$-$C_6$ alkoxy)carbonyl; or benzoyloxycarbonyl;

$R^4$ and $R^5$ are the same or different and each represents hydrogen, a $C_1$-$C_5$ alkyl group or a $C_1$-$C_5$ alkoxy group, or $R^4$ and $R^5$ together represent a $C_1$-$C_4$ alkylenedioxy group;

n is 1, 2 or 3; and

Y and Z are the same or different and each represents the oxygen atom or the imino group; and pharmaceutically acceptable salts thereof.

36. Compositions as claimed in claim 24, in which said active compound is selected from compounds of formula (Ib):

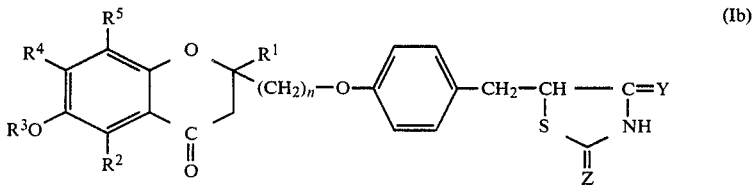

in which:

$R^1$ and $R^2$ are the same or different and each represents hydrogen or a $C_1$-$C_5$ alkyl group;

$R^3$ represents hydrogen; $C_1$-$C_6$ aliphatic acyl; ($C_5$-$C_7$ cycloalkane)carbonyl; benzoyl, benzoyl substituted with one to three substituents selected from the group of $C_1$-$C_4$ alkyl, $C_1$-$C_4$ alkoxy, hydroxy, halogen, nitro, amino and di($C_1$-$C_4$ alkyl)amino; naphthoyl; 4–7 membered heterocyclic acyl wherein heterocyclic moiety has O, S or N hetero atoms; phenyl($C_2$-$C_3$)aliphatic acyl; cinnamoyl; ($C_1$-$C_6$ alkoxy)carbonyl; or benzoyloxycarbonyl;

$R^4$ and $R^5$ are the same or different and each represent hydrogen, a $C_1$-$C_5$ alkyl group or a $C_1$-$C_5$ alkoxy group, or $R^4$ and $R^5$ together represent a $C_1$-$C_4$ alkylenedioxy group;

n is 1, 2 or 3;

and

Y and Z are the same or different and each represents the oxygen atom or the amino group;

and pharmaceutically acceptable salts thereof.

37. Compositions as claimed in claim 24, in which said active compound is selected from compounds of formula (Ic):

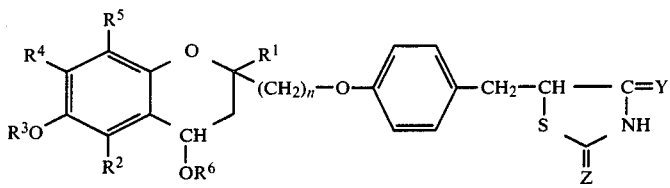

in which:
- R[1] and R[2] are the same or different and each represents hydrogen or a $C_1$–$C_5$ alkyl group;
- R[3] represents hydrogen; $C_1$–$C_6$ aliphatic acyl; ($C_5$–$C_7$ cycloalkane)carbonyl; benzoyl, benzoyl substituted with one to three substituents selected from the group of $C_1$–$C_4$ alkyl, $C_1$–$C_4$ alkoxy, hydroxy, halogen, nitro, amino and di($C_1$–$C_4$ alkyl)amino; naphthoyl; 4–7 membered heterocyclic acyl wherein heterocyclic moiety has O, S or N hetero atoms; phenyl($C_2$–$C_3$)aliphatic acyl; cinnamoyl; ($C_1$–$C_6$ alkoxy)carbonyl; or benzoyloxycarbonyl;
- R[4] and R[5] are the same or different and each represents hydrogen, a $C_1$–$C_5$ alkyl group or a $C_1$–$C_5$ alkoxy group, or R[4] and R[5] together represent a $C_1$–$C_4$ alkylenedioxy group;
- n is 1, 2 or 3;
- R[6] represents any one of the atoms or groups defined for R[3] and may be the same as or different from R[3]; and
- Y and Z are the same or different and each represents the oxygen atom or the imino group; and pharmaceutically acceptable salts thereof.

38. Compositions as claimed in claim 24 or claim 35, wherein said active compound is in the form of a salt with a cation.

39. Compositions as claimed in claim 24 or claim 35, wherein said active compound is in the form of the sodium salt.

* * * * *

UNITED STATES PATENT AND TRADEMARK OFFICE
CERTIFICATE OF CORRECTION

PATENT NO. : 4,572,912
DATED : February 25, 1986
INVENTOR(S) : Takao YOSHIOKA et al It is certified that error appears in the above-identified patent and that said Letters Patent is hereby corrected as shown below:

In the title page of the patent:

Under the heading of "References Cited", change the name of the inventor of the second listed reference to --Kawamatsu--.

Insert a third reference as follows:

--4,287,200    9/1981    Kawamatsu--.

In the Abstract:

The left-hand column, line 8, change "$C_1 14C_4$" to --$C_1-C_4$--.

UNITED STATES PATENT AND TRADEMARK OFFICE
CERTIFICATE OF CORRECTION

PATENT NO. : 4,572,912
DATED : February 25, 1986
INVENTOR(S) : Takao YOSHIOKA et al It is certified that error appears in the above-identified patent and that said Letters Patent is hereby corrected as shown below:

Column 19, equation (Ie), appearing at lines 10 - 15, change the "W" in the second segment of equation to $$-\!-\underset{OR^{61}}{\overset{}{\underset{|}{CH}}}-\!-.$$

Column 62 (Claim 32), line 27, change "claim 30 or claim 17" to --claim 30 or claim 31--.

Signed and Sealed this

Twentieth Day of January, 1987

Attest:

DONALD J. QUIGG

*Attesting Officer*  *Commissioner of Patents and Trademarks*

UNITED STATES PATENT AND TRADEMARK OFFICE

CERTIFICATE EXTENDING PATENT TERM
UNDER 35 U.S.C. § 156

PATENT NO.      :   4,572,912

ISSUED          :   February 25, 1986

INVENTOR(S)     :   Takao Yoshioka et al.

PATENT OWNER    :   Sankyo Company Limited

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,534 days from August 28, 2004, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 2nd day of September 1998.

Bruce A. Lehman
Assistant Secretary of Commerce and
Commissioner of Patents and Trademarks